US006403865B1

(12) United States Patent
Koziel et al.

(10) Patent No.: US 6,403,865 B1
(45) Date of Patent: Jun. 11, 2002

(54) METHOD OF PRODUCING TRANSGENIC MAIZE USING DIRECT TRANSFORMATION OF COMMERCIALLY IMPORTANT GENOTYPES

(75) Inventors: Michael G. Koziel; Nalini M. Desai, both of Cary; Kelly S. Lewis; Vance C. Kramer, both of Hillsborough; Gregory W. Warren, Cary; Stephen V. Evola, Apex; Lyle D. Crossland, Chapel Hill; Martha S. Wright, Cary; Ellis J. Merlin, Raleigh; Karen L. Launis, Franklinton, all of NC (US); Steven J. Rothstein, Guelph (CA); Cindy G. Bowman, Cary, NC (US); John L. Dawson; Erik M. Dunder, both of Chapel Hill, NC (US); Gary M. Pace, Cary, NC (US); Janet L. Suttie, Raleigh, NC (US); Nadine Carozzi, Raleigh, NC (US); Annick De Framond, Durham, NC (US); James O. Linder, Owatonna, MN (US); Robert L. Miller, Cedar Rapids, IA (US); Bruce W. Skillings, Innerkip (CA); Alan W. Mousel, Bluffton, IN (US); Albert R. Hornbrook, Bloomington, IL (US); Christopher P. Clucas, Washington Court House, OH (US); Moez Rajabali Meghji, Bloomington, IL (US); Andreas H. Tanner, Plaisance du Touch (FR); Francis E. Cassagne, Auch (FR); Gilles Pollini, L'Isle en Dodon (FR); Terry Ray Colbert, Troy, TN (US); Francis P. Cammack, Rochelle, IL (US)

(73) Assignee: Syngenta Investment Corp., Wilmington, DE (US)

( * ) Notice: Subject to any disclaimer, the term of this patent is extended or adjusted under 35 U.S.C. 154(b) by 0 days.

(21) Appl. No.: 08/438,666

(22) Filed: May 10, 1995

Related U.S. Application Data

(63) Continuation of application No. 08/008,374, filed on Jan. 25, 1993, now abandoned, which is a continuation-in-part of application No. 07/951,715, filed on Sep. 25, 1992, now Pat. No. 5,625,136, which is a continuation-in-part of application No. 07/772,027, filed on Oct. 4, 1991, now abandoned, application No. 08/008,374, which is a continuation-in-part of application No. 07/659,433, filed on Feb. 25, 1991, now abandoned, which is a continuation-in-part of application No. 07/573,105, filed on Aug. 24, 1990, now abandoned.

(51) Int. Cl.[7] .......................... A01H 5/00; A01H 4/00; A01H 1/20; C12N 5/04

(52) U.S. Cl. ...................... 800/302; 800/268; 800/265; 800/320.1; 536/23.71

(58) Field of Search ................................ 800/200, 205, 800/235, 250, DIG. 56; 435/172.1, 112.3, 240.1, 240.4, 240.45, 240.48, 240.49, 240.5; 47/58.03; 935/18

(56) References Cited

U.S. PATENT DOCUMENTS

| | | | | | |
|---|---|---|---|---|---|
| 4,448,885 | A | | 5/1984 | Schnepf et al. | |
| 4,467,036 | A | | 8/1984 | Schnepf et al. | |
| 4,761,373 | A | | 8/1988 | Anderson et al. | |
| 4,830,966 | A | | 5/1989 | Close | |
| 4,945,050 | A | | 7/1990 | Sanford et al. | |
| 5,023,179 | A | * | 6/1991 | Lan et al. | 435/172.3 |
| 5,100,792 | A | | 3/1992 | Sanford et al. | 435/172.1 |
| 5,350,689 | A | | 9/1994 | Shillito et al. | 435/240.47 |
| 5,371,003 | A | | 12/1994 | Murry et al. | |
| 5,380,831 | A | | 1/1995 | Adang et al. | 536/23.71 |
| 5,436,391 | A | | 7/1995 | Fujimoto et al. | 800/205 |
| 5,484,956 | A | * | 1/1996 | Lundquist et al. | 800/205 |
| 5,489,520 | A | * | 2/1996 | Adams et al. | 435/172.3 |
| 5,500,365 | A | | 3/1996 | Fischoff et al. | 435/240.4 |
| 5,508,468 | A | | 4/1996 | Lundquist et al. | |
| 5,538,877 | A | | 7/1996 | Lundquist et al. | |
| 5,538,880 | A | | 7/1996 | Lundquist et al. | |

(List continued on next page.)

FOREIGN PATENT DOCUMENTS

| | | |
|---|---|---|
| EP | 0160390 | 11/1985 |
| EP | 0290395 | 11/1988 |
| EP | 0292435 | 11/1988 |
| EP | 0431829 | 6/1989 |
| EP | 0348348 | 12/1989 |
| EP | 0353908 | 2/1990 |
| EP | 0359472 | 3/1990 |
| EP | 0374753 | 6/1990 |
| EP | 0385962 | 9/1990 |
| EP | 0408403 | 1/1991 |
| EP | 0431829 | 6/1991 |
| GB | 2140822 | 12/1984 |
| WO | 8402913 | 8/1984 |
| WO | 8601536 | 3/1986 |
| WO | 9010076 | 9/1990 |
| WO | WO9102059 | 2/1991 |
| WO | 9110725 | 7/1991 |
| WO | 9116432 | 10/1991 |
| WO | WO9209696 | 6/1992 |
| WO | WO9220809 | 11/1992 |

OTHER PUBLICATIONS

Ludwig et al. 1990. Science 247:449–450.*
Goff et al. 1990. EMBOJournal. 9(8):2517–2522.*
Wabiko et al. 1986. DNA. 5(4):305–314.*

(List continued on next page.)

*Primary Examiner*—Gary Benzion
(74) *Attorney, Agent, or Firm*—White & Case LLP

(57) ABSTRACT

Methods for transformation of maize with nucleic acid sequences of interest are disclosed. The method involves subjecting immature zygotic embryos or Type I callus to high velocity microprojectile bombardment. The method is capable of producing transformed maize lines of commercial importance and their hybrid combinations.

42 Claims, 7 Drawing Sheets

U.S. PATENT DOCUMENTS

| | | | | |
|---|---|---|---|---|
| 5,550,318 | A | 8/1996 | Adams et al. | |
| 5,554,798 | A | 9/1996 | Lundquist et al. | |
| 5,595,733 | A | 1/1997 | Carswell et al. | |
| 5,625,136 | A | 4/1997 | Koziel et al. | |
| 5,689,052 | A | 11/1997 | Brown et al. | |
| 5,780,708 | A | 7/1998 | Lundquist et al. | |
| 5,859,336 | A | 1/1999 | Koziel et al. | |
| 5,874,265 | A | 2/1999 | Adams et al. | |
| 5,886,244 | A | 3/1999 | Tomes et al. | 800/293 |
| 5,919,675 | A | 7/1999 | Adams et al. | |
| 5,990,387 | A | 11/1999 | Tomes et al. | 800/293 |
| 5,990,390 | A | 11/1999 | Lundquist et al. | |
| 6,013,863 | A | 1/2000 | Lundquist et al. | |
| 6,018,104 | A | 1/2000 | Koziel et al. | |
| 6,051,760 | A | 4/2000 | Koziel et al. | |
| 6,075,185 | A | 6/2000 | Koziel et al. | |
| 6,121,014 | A | 9/2000 | Koziel et al. | |
| 6,160,208 | A | 12/2000 | Lundquist et al. | |

OTHER PUBLICATIONS

Shimizu et al. 1988. Agric. Biol. Chem. 52(6):1565–1573.*
Perlak et al. 1991. Proc. Natl. Acad. Sci, USA. (Biochem.) 88: 3324–3328.*
Barton et al. 1987. Plant Physiol. 85: 1103–1109.*
Hodges et al. 1986. Bio/Technology. 4: 219–223.*
Tomes et al. 1985. Theor. Appl. Genet. 70: 505–509.*
Klein et al. 1989. Proc. Natl. Acad. Sci. USA (Genetics). 86: 6681–6685.*
Fromm et al. 1990. Bio/Technology. 8: 833–839.*
Gordon–Kamm et al. 1990. The Plant Cell. 2: 603–618.*
Gordon–Kamm et al. 1991. In Vitro Cell. Dev. Biol. 27P:21–27.*
Topping et al. 1991. Development. 112: 1009–1019.*
Brunke et al. 1991. TIBTECH. 9: 197–200.*
Murray et al. 1988. Nucleic Acids Research 17: 477–498.*
Russel et al., In Vitro Cell. Dev. Biol. 28P: 97–105, 1992.
Klein et al., Bio/Technology 6: 559–563, 1988.
Christou et al., TIBTECH 10: 239–246, 1992.
Christou et al., Bio/Technology 9: 957–962, 1991.
Fitch et al., Plant Cell Reports 9:189–194, 1990.
Taylor et al., Plant Cell Reports 10: 120–125, 1991.
Daniell et al., Plant Cell Reports 9: 615–619, 1991.
Reggiardo et al., Plant Science, 75: 237–243, 1991.
Duncan, D.R., et al., Planta 165:322–332 (1985).
Green, C.E., et al., Crop Science, 15:417–421 (1975).
Kamo, et al., Planta 172:245–251 (1987).
Mackey, C.J., Transgenic Plants, 2:21–33 (1993).
Rhodes, C.A., Bio/Technology 6:56–60 (1988).
Declaration of Steven v. Evola dated Sep. 3, 1992.
Testimony of Michael E. Fromm, Oct. 30, 1998, pp. 1175–1207, *Novartis v Monsanto Co. & DeKalb Genetics Corp.*, U.S. District Court for the District of Delaware, Civ. Act. No. 97–39; 97–40 (RRM).
Testimony of Thomas B. Klevorn, dated Jun. 16, 1998, pp. 48–145, *Monsanto Co.*, v *Mycogen Plant Sciences Inc., Agrigenetics, Inc. and Novartis Corp.*, U.S. District Court for the District of Del., Civ. Act. No. 96–133 (RRM).
Testimony of Michael A. Stephens, dated Feb. 19, 2001, pp. 1078–1079; 1098–1296, *DeKalb Genetics Co.* v *Pioneer Hi–Bred Int'l*, U.S. District Court for the Northern District of Del., Civ. Act. No. 96C50112 (PGR).
Ohta et al., Mol Gen Genet, 225:369–378 (1991).
Vaeck et al., Nature, 328:33–37 (1987).
Barton et al., Plant Physiol, 85:1103–1109 (1987).
Fischhoff et al., Bio/Technology, 5:807–813 (1987).
Geiser et al., Gene, 48:109–118 (1986).
Perlak et al., Proc. Natl. Acad, Sci., PNAS USA, 88:3324–3328 (1991).
Murray et al., Nucleic Acids Research, 17:477–498 (1989).
Conger et al., Plant Cell Reports, vol. 6, 345–347 (1987).
Murashige and Skoog, Physiol. Plant, 15:473–497 (1962).
Chih–ching et al., Scientia Sinica, 18:659–668 (1975).
Schenck and Hidebrandt, Can. J. Botany, 50:199–204 (1972).
Gamborg et al., Experimental Cell Research, 50:151–158 (1968).
Tomes et al., Theor. Appl. Genet., 70:505–509 (1985).
Armstrong et al., Planta, 164:207–214 (1985).
Tomes et al., in Cereal Tissue and Cell Culture, pp. 175–203 (Bright, ed.) (1985).
Hodges et al., Biotechnology, 4:219–223 (1986).
Gordon–Kramm et al., The Plant Cell 2:603–618 (1990).
Close, Plant Science, 52:81–89 (1987).
Sanford et al., Particulate Science and Technology, 5:27–37 (1987).
Christou et al., Plant Physiology, 87:671–674 (1988).
McCabe et al., Bio/Technology, 6:923–926 (1988).
Potrykus, Bio/Technology, 8:535–542 (1990).
Potrykus, Trends in Biotechnology, 7:269–273 (1989).
Klein et al., PNAS USA, 85:4305–4309 (1988).
Klein et al., Bio/Technology, 6:559–563 (1988).
Klein et al., Plant Physiology, 91:440–444 (1989).
Gard et al., Plant Physiology, 92:334–339 (1990).
Green et al., Crop Science, 15:417–421 (1975).
Green et al., Somatic Cell Genetic Systems in Corn in Advances in Gene Technology, (Academic Press, 1983).
Duncan et al., Plants, 165:322–332 (1985).
Horsch et al., Science, 225:1229 (1985).
Marton, In Cell Culture and Somatic Cell Genetics of Plants vol. 1, (Vasil, ed, Academic Press, Inc. 1984) pp. 514–521.
Paszkowski et al., EMBO J., 3:2717 (1984).
Shillito et al., Bio/Technology, 3:1099 (1985).
Loerz et al., Mol. Gen. Genet., 199:178 (1985).
Negrutiu et al., Plant Mol. Biol., 8:363 (1987).
Reich et al., Bio/Technology, 4:1001–1004 (1986).
Klein et al., Nature, 327:70 (1987).
Bevan et al., Nature, 304:184–187 (1983).
Pierce et al., Plant Gene Systems and Their Biology, (Alan R. Liss, Inc., (1987) pp. 301–310.
Velten et al., EMBO J., 3:2723–2730 (1984).
Hofte et al., Microbiol. Rev., 53:242–255 (1989).
Sekar et al., PNAS USA, 84:7036–7040 (1987).
Adang et al., Gene, 36:289–300 (1985).
Hofte et al., Nucleic Acids Research, 15:7183 (1987).
Oeda et al., Gene, 53:113–119 (1987).
Widner et al., J. Bacteriology, 171:965–974 (1989).
Hohn et al., in Current Topics in Microbiology and Immunology, 96:194–220.

* cited by examiner

METHOD OF PRODUCING TRANSGENIC MAIZE USING DIRECT TRANSFORMATION OF COMMERCIALLY IMPORTANT GENOTYPES

This application is a continuation of Ser. No. 08/008,374, filed Jan. 25, 1993, now abandoned, which is a continuation-in-part of both: (a) Ser. No. 07/951,715 filed Sep. 25, 1992, now U.S. Pat. No. 5,625,136 issued Apr. 29, 1997, which is a continuation-in-part of Ser. No. 07/772,027 filed Oct. 4, 1991, and (b) Ser No. 07/659,433 filed Feb. 25, 1991, now abandoned, which is a continuation-in-part of Ser. No. 07/573,105, filed on Aug. 24, 1990, now abandoned. application Ser. No. 07/951,715 (now U.S. Pat. No. 5,625,136) and application Ser. No. 07/772,027 are incorporated herein in their entirety.

FIELD OF THE INVENTION

The present invention relates to the transformation of maize genotypes by microprojectile bombardment.

BACKGROUND OF THE INVENTION

The use of genetic engineering to introduce new agronomically important traits into maize such as insect resistance will have many commercial benefits. In order to accomplish this in the most expedient fashion it is necessary to have a method of transformation that can be used with maize genotypes that are commercially valuable.

The majority of instances of maize transformation have used a genotype known as A188, or derivatives of A188. This is because these lines are easily established in vitro as an embryogenic line that forms Type II, or friable, embryogenic callus and suspension cultures. Such Type II cultures have been exclusively preferred as a recipient of introduced genes in transformation methods. Unfortunately, A188 is an inferior inbred for the development of commercially important hybrids. (Hodges et al., *Biotechnology*, 4:219, 1986). Working with such "model" maize lines as A188 is disadvantageous in that extensive breeding is usually required in order to develop maize lines with a desirable genetic composition. What is needed is a method that can be used with commercially valuable maize lines without the need for reliance on such "model" systems based on Type II or suspension cultures.

Microprojectile bombardment has been advanced as an effective transformation technique for cells, including cells of plants. In Sanford et al., *Particulate Science and Technology*, 5: 27–37 (1987) it was reported that microprojectile bombardment was effective to deliver nucleic acid into the cytoplasm of plant cells of *Allium cepa* (onion). Christou et al., *Plant Physiology* 87: 671–674 (1988) reported the stable transformation of soybean callus with a kanamycin resistance gene via microprojectile bombardment. Christou et al. reported penetration at approximately 0.1 to 5% of cells. Christou further reported observable levels of NPTII enzyme activity and resistance in the transformed calli of up to 400 mg/L of kanamycin. McCabe et al., *Bio/Technology* 6: 923–926 (1988) report the stable transformation of *Glycine max* (soybean) using microprojectile bombardment. McCabe et al. further report the recovery of a transformed $R_1$ plant from an $R_0$ chimeric plant.

Transformation of monocots and, in particular, commercially valuable maize lines, has been problematic. Although there have been several reports of stable plant transformation utilizing the microprojectile bombardment technique, such transformation has not resulted in the production of fertile, regenerated transgenic maize plants of a commercially valuable genotype —each report used the genotype A188 or its derivatives (Fromm et al, *BioTechnology*, 8:833, 1990; Walters et al., *Pl. Mol. Biol.* 18:189, 1992, Gordon-Kamm et al., *Plant Cell*, 2:603, 1990). There are two reports of maize transformation using commercially valuable lines but both rely on the availability of Type II, friable embryogenic callus as a recipient for gene delivery (Jayne et al., 1991 Meeting of the International Society for Plant Molecular Biology, Abstract #338; Aves et al., 1992 World Congress on Cell and Tissue Culture, In Vitro 28:124A, Abstract #P-1134). Prior to the present invention, successful direct transformation of commercially valuable maize lines has not been achieved using microprojectile bombardment of immature zygotic embryos or Type I embryogenic callus.

SUMMARY OF THE INVENTION

Figure 1:
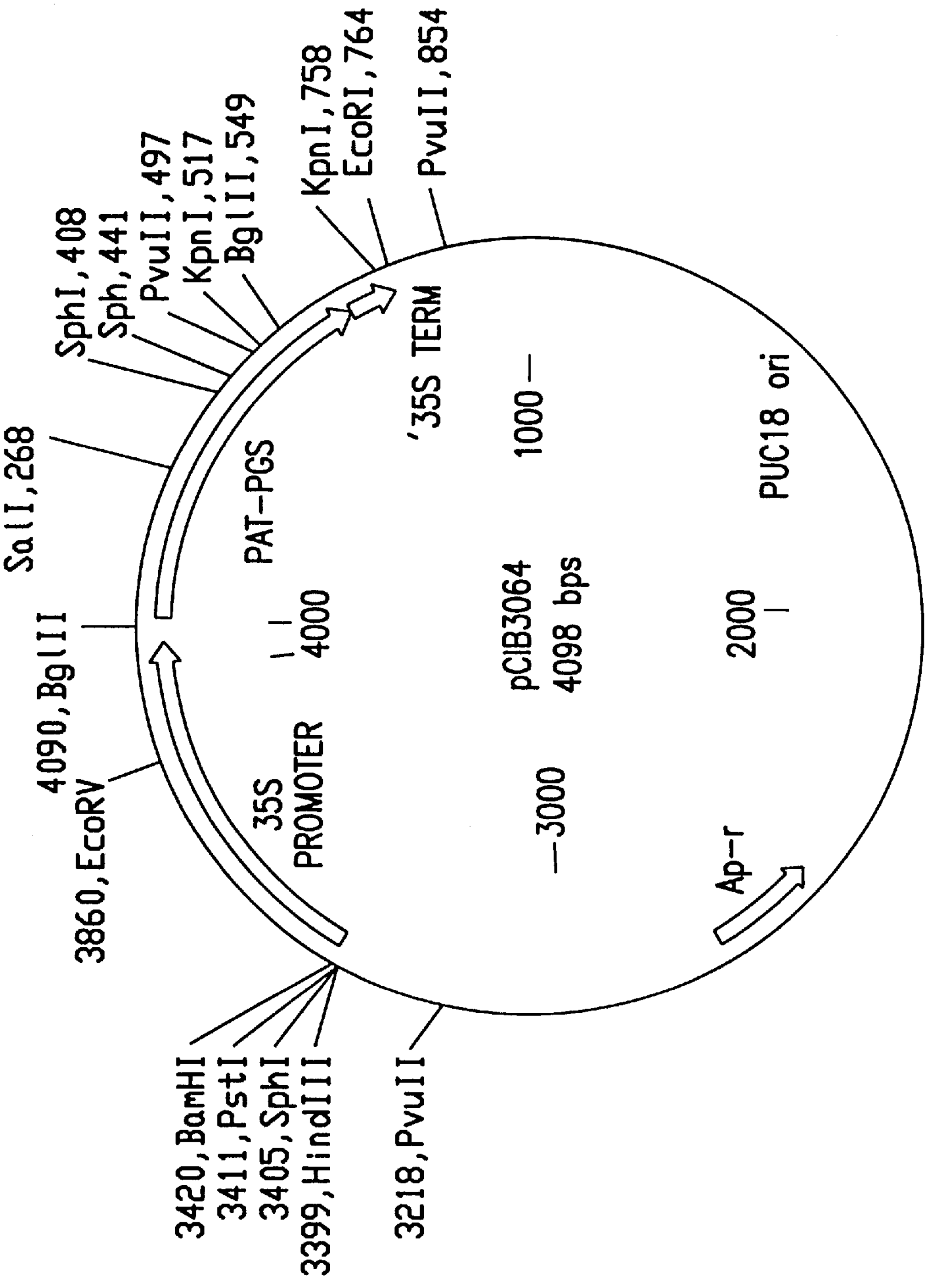
FIG. 1 shows the plasmid map of the vector pCIB3064 containing the 35S/bar chimeric gene.

The present invention is drawn to the stable transformation of maize with nucleic acid sequences of interest, the regeneration of fertile transgenic maize plants and their subsequent use for the creation of commercially valuable lines and hybrids created with those lines. In the invention, immature zygotic embryos are subjected to high velocity microprojectile bombardment as a means of gene delivery within about 14 days after excision from the plant. After initiation of embryogenic callus and selection for transformed cells, stably transformed plants may be regenerated which express the foreign genes of interest. Alternatively, callus derived from immature zygotic embryos having the Type I character may also be employed as a recipient for gene delivery. The method is applicable to any genotype of maize, especially commercially important ones. In this manner, the method produces transformed maize lines of commercial importance and their hybrid combinations.

DETAILED DESCRIPTION OF THE INVENTION

A method for the transformation of any maize line and the regeneration of transgenic maize plants is provided. The method involves the delivery of nucleic acids, or particularly, genes of interest, directly to immature zygotic embryos. Alternatively, said nucleic acids or genes of interest may be delivered to serially-propagated Type I embryogenic callus obtained from immature zygotic embryos. Stably transformed cells are obtained and are regenerated into whole, fertile plants that express the foreign gene(s). Furthermore, the fertile transformed plants are capable of producing transformed progeny that express the foreign gene(s). The method provides for the direct transformation of commercially important maize genotypes, for obtaining transformed inbreds and for their hybrid combinations.

Embryogenic callus of maize is obtained by the process of somatic embryogenesis. Somatic embryogenesis is a process by which fully or partially-formed embryos arise from somatic tissue. This is in contrast to zygotic embryogenesis whereby embryos form from gametic tissue. Somatic embryogenesis may be induced from several viable tissues of maize, including leaf bases (Conger et al., *Pl. Cell Rep.* 6:345, 1987), tassel primordia (Rhodes et al., *Pl. Sci.* 46:225, 1986) and immature embryos (Green et al., *Crop Science* 15:417, 1975). In the present invention, immature embryos are the preferred source of embryogenic callus.

Immature zygotic embryos of maize can be obtained by pollinating an ear with viable pollen then removing the ear from the plant at some later time. Typically, immature embryos for use as sources of embryogenic callus are in the size range of about 0.5 mm to about 3.0 mm, more particularly about 1.0 to about 2.5, especially preferred from 1.5 to 2.0. The immature embryos may, for example, be removed from the ear individually by dissection or in bulk by "creaming" the kernels. Isolated immature embryos are placed with the zygotic embryo axis side in contact with an appropriate nutrient medium (Green et al., supra, 1975). Embryogenic callus is typically observed on the immature embryo within about 14 days of placement on the medium. This initial period is called the "initiation" step. After the initiation step, the embryogenic callus is generally transferred to a different medium for establishment and maintenance of serially-propagatable embryogenic callus (called the "maintenance" medium), although the same medium as that for "initiation" may also be used. Incubation of cultures typically takes place at 25 C in the dark or under low light. Embryogenic callus can be obtained in this way from a wide variety of maize genotypes.

Two main types of embryogenic callus have been described in the scientific literature. Type I embryogenic callus has been defined as "translucent, convoluted and compact callus" (Tomes et al., *Theor. Appl. Genet.* 70:505–509, 1985) or as "compact, morphologically complex" (Armstrong et al., *Planta*, 164:207–214 (1985)). Type II embryogenic callus has been defined as "friable and fast growing [callus] with well defined somatic embryos with suspensor-like structures" (Tomes et al., supra, 1985) or as "friable, embryogenic" (Armstrong et al., supra, 1985). It is within the scope of this invention that either or both types of embryogenic callus may be obtained from the immature zygotic embryos, or other viable tissue such as tassel primordia, leaf bases or meristems which may also be used as a source of embryogenic callus.

In order to obtain embryogenic callus the isolated immature maize embryos must be cultured on an appropriate medium. Many types of medium have been shown to be useful for the establishment of embryogenic callus from a variety of genotypes, including some commercially important ones (Hodges et al., *Bio/Technology* 4:219, 1986; Duncan et al., *Planta* 165:322, 1985). In practice, a preferred medium must be found experimentally for each genotype. Typically in such an experimental procedure a selection of basal media, sucrose concentrations, and growth regulator types and concentrations are combined in a factorial arrangement. Immature embryos from each genotype to be tested are placed onto medium representing each factorial combination. Initiation frequencies are scored for each medium and the ones producing the highest scores are used in a second round of experimentation. In this second round, the selected media combinations are further optimized for the individual genotypes by fine-tuning the growth-regulator type and concentration, and sucrose concentration. For example, Table I below indicates the preferred medium for the initiation of embryogenic callus for several of the genotypes disclosed in this invention.

TABLE I

| Genotype | Initiation Medium |
|---|---|
| LH51 | MS basal medium, G10 amendments, 6% sucrose, 5 mg/L dicamba |
| CG00716 | JMS basal medium, G5 amendments, 9% sucrose, 5 mg/L dicamba |
| CG00526 | D basal medium, G8 amendments, 2% sucrose, 5 mg/L chloramben |
| CG00642 | JMS basal medium, G5 amendments, 10% sucrose, 4 mg/L dicamba |
| LH82 | LM basal medium, G6 amendments, 4% sucrose, 0.2 mg/L 2,4-D |
| CG00689 | MS basal medium, G1 amendments, 6% sucrose, 0.5 mg/L 2,4-D |
| CGNC4206 | MS basal medium, G1 amendments, 6% sucrose, 0.5 2,4-D |
| CG00629 | D basal medium, G8 amendments, 2% sucrose, 5 mg/L chloramben |
| (H99xFR16)xPa91 | JMS basal medium, G5 amendments, 2% sucrose, 1 mg/1 dicamba |
| Hi II | JMS basal medium, G5 amendments, 2% sucrose, 10 mg/L silver nitrate, 5 mg/L dicamba |

The basal media formulas used for the initiation of embryogenic callus of the genotypes in Table I may be found in the following citations and is herein incorporated by reference: "D", (Duncan et al., *Planta* 165:322, 1985); "KM", (Kao et al., *Planta* 126:105, 1975); "LM", (Litvay et al., *Plant Cell Reports* 4:325, 1985); "MS", (Murashige et al, *Physiologia Plantarum* 15:473, 1962). The basal medium "JMS" is the medium known as "SH" (Schenk et al., *Can. J. Bot.* 50:199, 1972) modified by replacing the inorganic nitrogen compounds with those found in "MS" (Murashige et al., supra, 1962).

The formulas of the amendments used for the initiation of embryogenic callus of the genotypes in Table I are found in the following table. The amendments used with the "KM" basal medium were as described in Kao et al., supra.

TABLE II

| | Amendment Formulas, per Liter of Medium mg | | | | |
|---|---|---|---|---|---|
| Component | G1 | G5 | G6 | G8 | G10 |
| Nicotinic Acid | 0.5 | 5.0 | 0.5 | 0.2 | 0.5 |
| Pyridoxine-HCl | 0.5 | 0.5 | 0.1 | 0.2 | 0.5 |
| Thiamine-HCl | 0.1 | 5.0 | 0.1 | 0.5 | 0.1 |
| Glycine | 2.0 | — | — | — | 2.0 |
| myo-Inositol | 100 | 100 | 100 | — | 100 |
| Choline HCl | — | — | — | 0.1 | — |
| Riboflavin | — | — | — | 0.1 | — |
| Biotin | — | — | — | 0.1 | — |
| Folic Acid | — | — | — | 0.5 | — |
| CaPantothenate | — | — | — | 0.1 | — |
| Cyanocobalamin | — | — | — | 0.014 | — |
| Casein hydrolysate | 100 | 100 | 100 | — | — |
| Proline | 2800 | 2800 | 2800 | — | — |

Often, the preferred "maintenance" medium must be determined experimentally, as is done for "initiation". Table III describes the "maintenance" medium found to be useful for several of the genotypes disclosed in the present invention.

TABLE III

| Genotype | Maintenance Medium |
|---|---|
| LH51 | MS basal medium, G10 amendments, 3% sucrose, 0.25 mg/L 2,4-D |
| CG00716 | N6 basal medium, 25 mM proline, 100 mg casein hydrolysate, 2% sucrose, 1.5 mg/L 2,4-D |
| CG00526 | D basal medium, G8 amendments, 2% sucrose, 0.5 mg/L Z,4-D |
| LH82 | LM basal medium, G6 amendments, 3% sucrose, 3 mg/L chloramben |
| CG00689 | MS basal medium, G10 amendments, 2% sucrose, 1.5 mg/L 2,4-D |
| CGNC4206 | D basal medium, G8 amendments, 2% sucrose, 1.2 2,4-D |
| (H99xFR16)xPa91 | D basal medium, G4 amendments, 2% sucrose, 0.5 mg/1 2,4-D |
| Hi II | N6 basal medium, G5 amendments, 2% sucrose, 1 mg/L 2,4-D |

In Table III, "N6" basal medium refers to that described in Chu et al. Scientia Sinica, XVIII:659, 1975. The formulas for the amendments used in "maintenance" medium may be found in Table II.

According to the present invention, nucleic acid sequences or genes of interest are delivered to the immature embryos within the "initiation" step of the development of an embryogenic callus, i.e., within about 14 days of the placement of the immature embryos on a nutrient medium capable of supporting the initiation and development of embryogenic callus. After gene delivery and initiation of embryogenic callus, the embryogenic callus is transferred to a "maintenance" medium for subculture in either the presence or absence of a selection agent. In another embodiment of the invention, Type I callus developed using the methods above may also be used as a recipient of the nucleic acid sequences or genes of interest. In this instance, after delivery of the nucleic acid of interest, the Type I embryogenic callus is normally transferred to fresh "maintenance" medium, with or without a selection agent.

There are available many types of microprojectile bombardment devices, all working on essentially the same principle of accelerating micrometer size particles sufficient to cause penetration into the target tissues and cells. Since it is known that bombardment devices based on gunpowder do not work for the present invention, the preferred devices are those that use some form of gas expansion for the accelerating force for the microprojectiles such as air, carbon dioxide, nitrogen, water vapor or helium. The most preferred device for use in the claimed method is one based on compressed helium such as the DuPont PDS-1000/He.

For the bombardment of Type I embryogenic callus, the callus must be subdivided into smaller pieces. This can be achieved by chopping, maceration, dissection or other mechanical means. It is also possible to subdivide the callus through enzymatic means. Enzymes that digest the cell wall or cell-wall components may be used to reduce the integrity of the callus mass. Such enzymes include cellulases, macerases, pectinases, hemi-cellulases and others well known in the art. After the callus is subdivided, it is rinsed several times with liquid culture medium.

In preparation for gene delivery by microprojectile bombardment, either the immature embryos or Type I embryogenic callus may optionally be pre-treated with an osmotically-active agent to plasmolyze the cells for a period from about 1 to about 24 hours, preferably from about 1 to about 12 hours, most preferably from about 1 to about 6 hours. Typically, the recipient material is treated with a concentration of sucrose that produces an osmotic pressure in the medium that is greater than that in the recipient material. The concentration of sucrose may range from about 2 to about 18%, preferably from about 6 to about 12%. It is also within the scope of this invention that other osmotically-active agents may be used in concentrations sufficient to cause the plasmolysis of the cells of the recipient material, such as sorbitol, glucose, mannitol and various molecular weight ranges of polyethylene glycol. The recipient material is kept in the presence of the osmotically-active agent after gene delivery for a period of about 1 to about 24 hours, preferably from about 3 to about 18 hours, most preferably from about 10 to about 18 hours.

In a preferred embodiment of the invention, the set-up and use of the microprojectile bombardment device, as well as the targeting of the recipient material, is described below. Other arrangements are also possible.

The DNA is prepared for microprojectile bombardment by chemical precipitation in the presence of micrometer size gold, essentially according to the published procedure of DuPont. In addition to gold, other dense particles of micrometer size may be used, such as tungsten or platinum. In one modification of the DuPont procedure, the particles themselves are first prepared by suspending them in water and sonicating. The sonicated particles are then pelleted by centrifugation and resuspended in an aqueous solution of 50% glycerol. Particles prepared in this way are then aliquoted into individual tubes containing approximately 3 mg of gold particles per tube in a volume of 50 ul. DNA is added to each tube in varying amounts, depending upon the number of plasmids to be used, their sizes and the final concentration of DNA desired. For example, in a typical preparation to include four plasmids for use in the present invention, 2 ug of pCIB3089, 2 ug pCIB4436, 3 ug pCIB4433 and 4 ug pCIB4430 are added to each tube of aliquoted gold particles. Next, about 50 ul of 2.5 M $CaCl_2$ and about 20 ul of 1M spermidine are added, in that order, to each tube while vortexing for about 3 minutes. The DNA/gold complex is then gently centrifuged. The supernatant is removed, the particles are washed once with 250 ul of absolute ethanol, pelleted again and then resuspended in about 75 ul of fresh absolute ethanol. Each tube prepared in this way is enough of the DNA/gold complex for six "shots" with the PDS-1000/He. Ten ul of the well-suspended DNA/gold complex is pipetted onto the macrocarrier sheet in a vibration-free environment.

In the PDS-1000/He device, a burst of helium is released by rupture of a plastic disk which is available in different pressure grades. For example, single disks, or combinations of disks, can be obtained which rupture at 200, 450, 650, 900, 1100 1350, 1550, 1800, 2000 and 2200 pounds per square inch of helium. This burst of gas propels the macrocarrier sheet, which is stopped by a stainless steel screen. The screen may be of different mesh sizes, such as 10×10, 16×16, 24×24, etc. Other settings are the macrocarrier flight distances, gap distance, and particle flight distance. These settings are described in detail in the manufacturer's user's manual. Typically, a gap distance of about 5.5 mm, a macrocarrier flight distance of about 10 mm and a particle flight distance of about 6 to 9 cm is used. In addition, a screen or baffle may be inserted within the particle flight distance between the stopping screen and the target plate. Such a screen or baffle disturbs the shock wave from the expanding gas thereby reducing damage to the target. In one example, stainless steel screens with an opening of about 100 um is used. Other opening sizes and material composition may be used.

The immature embryos or Type I embryogenic callus may be arranged on the target plate in different patterns. Through a series of experiments, optimized patterns were developed for immature embryos. In one optimized pattern, the immature embryos are arranged in a circular pattern, the circle being about 2 cm in diameter. The immature embryos are placed on the periphery of the circle. Approximately 36 immature embryos are placed onto each target plate. Furthermore, the target plate may be angled relative to the microcarrier launch assembly. This ensures maximum saturation of the basipetal portion of the immature embryo by the particle spread. It is the basipetal portion of the immature embryo that gives rise to the embryogenic response.

In one example of the bombardment of Type I embryogenic callus, the callus is placed on the periphery of a circle about 1 cm diameter on a nutrient medium. The mechanical settings of the bombardment device may be placed at positions similar or identical to the settings recited above for the bombardment of immature embryos.

It should be noted that the target pattern and gun settings are interrelated. In other words, the use of other mechanical settings on the microprojectile bombardment device can produce other optimal arrangements of the recipient tissue on the target plate. Other combinations of mechanical settings and target patterns are within the scope of the invention.

The recombinant DNA molecules of the invention also can include a marker gene to facilitate selection in recombinant plant cells. Examples of markers include resistance to a biocide such as an antibiotic, e.g. kanamycin, hygromycin, chloramphenicol, paramomycin, methotrexate and bleomycin, or a herbicide such as imidazolinones, sulfonylureas, glyphosate, phosphinothricin (PPT), glufosinate, or bialaphos. Marker genes are well known in the art. In one embodiment of the invention the selection agent phosphinothricin is used in conjunction with the selectable marker gene known as bar, which encodes for the enzyme phosphinothricin acetyltransferase. This enzyme acetylates the phosphinothricin molecule, thereby rendering it non-toxic to plant cells. The bar gene may be operably linked to a constitutive promoter such as the CaMV 35S promoter; the CaMV 19S promoter; *A. tumefaciens* promoters such as octopine synthase promoters, mannopine synthase promoters, nopaline synthase promoters, or other opine synthase promoters; ubiquitin promoters, actin promoters, histone promoters and tubulin promoters. Other promoters may also be used. In one embodiment of the present invention, the bar coding sequence is operably linked to the CaMV 35S promoter.

Selection of transformed cells in vitro is accomplished by including the selection agent of interest in the medium used to induce and support the establishment of embryogenic callus. Only cells in which the selectable marker is integrated into the chromosome and is expressed, i.e., are transformed, will survive the selection agent. Over time, the cells will grow into an embryogenic callus in the presence of the selection agent eventually reaching a mass sufficient for regeneration of whole, fertile plants. Typically, such embryogenic callus can be maintained for long periods of time in the presence of selection agent and still retain its ability to produce whole, fertile plants. The minimum time required to obtain an embryogenic callus of sufficient mass under selection pressure can range from about 2 weeks to about 24 weeks, more preferably about 4 weeks to about 20 weeks, most preferably about 8 weeks to about 12 weeks.

Transformed cells may also be selected in vitro through visual means. In order to accomplish this, a scorable marker is generally used. Examples of scorable markers would be the regulatory or structural genes controlling anthocyanin biosynthesis, GUS (beta-glucuronidase), luciferase, opine synthetases, thaumatin, beta-galactosidase, unique synthetic epitopes designed for easy detection by ELISA, phycobiliproteins and various fluorigenic substances. In a particular embodiment of the present invention the use is made of coding sequences for the anthocyanin regulatory genes known in the art as C1 and B-Peru (Goff et al., *EMBO Journal*, 9: 2517, 1990). Such coding sequences, operably linked to one or more of the several constitutive promoters listed above, can be used to isolate transformants on the basis of the red pigmentation of cells transformed with such genes.

Fertile transformed plants may be regenerated from isolated transformed embryogenic callus by several means. In general, the transformed embryogenic callus is transferred to a nutrient medium devoid of an auxin-type phytohormone, or is passaged through a series of nutrient media with diminishing concentrations of phytohormone. Other phytohormones may be used during the regeneration step, such as cytokinins (both natural and synthetic) and gibberellins. In some instances, inhibitors of phytohormone action may also be used, such as silver nitrate, ancymidol or TIBA. Other amendments to the nutrient medium for regeneration such as activated charcoal and various gelling agents are also known in the art.

In one example of the present invention, embryogenic callus was removed from maintenance medium containing PPT after 12 weeks and placed on regeneration medium containing MS basal medium, 3% sucrose, 0.25 mg/L 2,4-D and 5 mg/L benzyladenine. After 2 weeks the embryogenic callus began to regenerate and was transferred to MS basal medium with 3% sucrose. Plantlets are obtained during incubation under light. Such plants may be transferred to a greenhouse environment after sufficient root mass has developed.

In another embodiment of the invention, transformed embryogenic callus is transferred from maintenance medium containing phosphinothricin to regeneration medium consisting of MS medium, 3% sucrose and also containing phosphinothricin. Regeneration under such selective conditions also produces plantlets during incubation under light, which again may be transferred to a greenhouse environment after sufficient root mass has developed.

As will be evident to one of skill in the art, now that a method has been provided for the stable transformation of maize according to the claimed method, any gene of interest can be used in the methods of the invention. For example, a maize plant can be engineered to express disease and insect resistance genes, genes conferring nutritional value, genes to confer male and/or female sterility, antifungal, antibacterial or antiviral genes, and the like. Likewise, the method can be used to transfer any nucleic acid to control gene expression. For example, the DNA to be transferred could encode antisense RNA.

The present invention also encompasses the production by the disclosed method of transformed maize plants and progeny containing a gene or genes which encode for and express insecticidal proteins. Such genes may be derived from the genus Bacillus, for example *Bacillus thuringiensis*. In a particular embodiment of the present invention is the use of the claimed method to produce transformed maize plants containing a gene or genes whose nucleic acid sequence has been altered so as to be optimized for expression in maize. Examples of such genes are found in Table 5

(SEQ ID NO:1), Table 6 (SEQ ID NO:3), Table 7 (SEQ ID NO:5), Table 8 (SEQ ID NO:6), Table 9 (SEQ ID NO:7), Table 10 (SEQ ID NO:9) and Table 11 (SEQ ID NO:11). A complete description of the creation of said gene or genes may be found in U.S. Ser. No. 951,715 which is herein incorporated by reference. A summary of that disclosure is given below.

A nucleic acid sequence of interest in the present invention includes one which encodes the production of an insecticidal toxin, preferably a polypeptide sharing substantially the amino acid sequence of an insecticidal crystal protein toxin normally produced by *Bacillus thuringiensis* (BT). The synthetic gene may encode a truncated or full-length insecticidal protein (IP). Especially preferred are synthetic nucleic sequences which encode a polypeptide effective against insects of the order Lepidoptera and Coleoptera, and synthetic nucleic acid sequences which encode a polypeptide having an amino acid sequence essentially the same as one of the crystal protein toxins of *Bacillus thuringiensis* variety kurstaki, HD-1.

The present invention provides the use of synthetic nucleic acid sequences to yield high level expression of active insecticidal proteins in maize plants. The synthetic nucleic acid sequences of the present invention have been modified to resemble a maize gene in terms of codon usage and G+C content. As a result of these modifications, the synthetic nucleic acid sequences of the present invention do not contain the potential processing sites which are present in the native gene. The resulting synthetic nucleic acid sequences (synthetic BT IP coding sequences) and plant transformation vectors containing this synthetic nucleic acid sequence (synthetic BT IP genes) result in surprisingly increased expression of the synthetic BT IP gene, compared to the native BT IP gene, in terms of insecticidal protein production in plants, particularly maize. The high level of expression results in maize cells and plants that exhibit resistance to lepidopteran insects, preferably European Corn Borer and *Diatrea saccharalis*, the Sugarcane Borer.

For example, the maize codon usage table described in Murray et al., *Nucleic Acids Research*, 17:477 1989, the disclosure of which is incorporated herein by reference, was used to reverse translate the amino acid sequence of the toxin produced by the *Bacillus thuringiensis* subsp. kurstaki HD-1 cryIA(b) gene, using only the most preferred maize codons. This sequence was subsequently modified to eliminate unwanted restriction endonuclease sites, and to create desired restriction endonuclease sites. These modifications were designed to facilitate cloning of the gene without appreciably altering the codon usage or the maize optimized sequence. During the cloning procedure, in order to facilitate cloning of the gene, other modifications were made in a region that appears especially susceptible to errors induced during cloning by the polymerase chain reaction (PCR).

In a preferred embodiment of the present invention, the protein produced by the synthetic nucleic acid sequence of interest is effective against insects of the order Lepidoptera or Coleoptera. In a more preferred embodiment, the polypeptide encoded by the synthetic nucleic acid sequence of interest consists essentially of the full-length (SEQ ID NOS: 1,3,6,7,9 and 11) or a truncated (SEQ ID NO:5) amino acid sequence of an insecticidal protein normally produced by *Bacillus thuringiensis* var. kurstaki HD-1. In a particular embodiment, the synthetic DNA sequence (SEQ ID NO:5) encodes a polypeptide consisting essentially of a truncated amino acid sequence of the BT CryIA(b) protein.

The present invention also encompasses the use of maize optimized coding sequences encoding other polypeptides, including those of other *Bacillus thuringiensis* insecticidal polypeptides or insecticidal proteins from other sources. For example, cryIB genes from *Bacillus thuringiensis* can be maize optimized, and then stably introduced into maize plants. It is also within the scope of this invention that the nucleic acid sequences of interest which encode insecticidal proteins may be either in the native or synthetic forms, optimized for expression in maize, and derived from any species of the genus Bacillus.

The insecticidal proteins produced by the nucleic acid sequences of interest in the present invention are expressed in a maize plant in an amount sufficient to control insect pests, i.e. insect controlling amounts. It is recognized that the amount of expression of insecticidal protein in a plant necessary to control insects may vary depending upon species of plant, type of insect, environmental factors and the like. Generally, the insect population will be kept below the economic threshold which varies from plant to plant. For example, to control European corn borer in maize, the economic threshold is 0.5 eggmass/plant which translates to about 10 larvae/plant.

In the present invention, the coding sequence of the nucleic acids of interest is a synthetic maize-optimized gene under the control of regulatory elements such as promoters which direct expression of the coding sequence. Such regulatory elements, for example, include monocot or maize and other monocot functional promoters to provide expression of the gene in various parts of the maize plant.

The regulatory element may be constitutive. That is, it may promote continuous and stable expression of the gene. Such promoters include but are not limited to the CaMV 35S promoter; the CaMV 19S promoter; *A. tumefaciens* promoters such as octopine synthase promoters, mannopine synthase promoters, nopaline synthase promoters, or other opine synthase promoters; ubiquitin promoters, actin promoters, histone promoters and tubulin promoters.

The regulatory element may also be a tissue-preferential or tissue-specific promoter. The term "tissue-preferred promoter" is used to indicate that a given regulatory DNA sequence will promote a higher level of transcription of an associated structural gene or DNA coding sequence, or of expression of the product of the associated gene as indicated by any conventional RNA or protein assay, or that a given DNA sequence will demonstrate some differential effect; i.e., that the transcription of the associated DNA sequences or the expression of a gene product is greater in some tissue than in all other tissues of the plant. Preferably, the tissue-preferential promoter may direct higher expression of the synthetic gene in leaves, stems, roots and/or pollen than in seed. "Tissue-specific promoter" is used to indicate that a given regulatory DNA sequence will promote transcription of an associated coding DNA sequence essentially entirely in one or more tissues of a plant, or in one type of tissue, e.g. green tissue, while essentially no transcription of that associated coding DNA sequence will occur in all other tissues or types of tissues of the plant. Numerous promoters whose expression are known to vary in a tissue specific manner are known in the art. One such example is the maize phosphoenol pyruvate carboxylase (PEPC), which is green tissue-specific. See, for example, Hudspeth, R. L. and Grula, J. W., Plant Molecular Biology 12:579–589, 1989. Other green tissue-specific promoters include chlorophyll a/b binding protein promoters and RubisCO small subunit promoters.

The regulatory element may also be inducible, such as by heat stress, water stress, insect feeding or chemical induction, or may be developmentally regulated.

In one preferred nucleic acid of interest, the regulatory element is a pith-preferred promoter isolated from a maize TrpA gene.

That is, the promoter in its native state is operatively associated with a maize tryptophan synthase-alpha subunit gene (hereinafter "TrpA"). The encoded protein has a molecular mass of about 38kD. Together with another alpha subnit and two beta subunits, TrpA forms a multimeric enzyme, tryptophan synthase.

Each subunit can operate separately, but they function more efficiently together.

The nucleic acids of interest in the present invention also include purified pollen-specific promoters obtainable from a plant calcium-dependent phosphate kinase (CDPK) gene. That is, in its native state, the promoter is operably linked to a plant CDPK gene. In a preferred embodiment, the promoter is isolated from a maize CDPK gene. By "pollen-specific," it is meant that the expression of an operatively associated structural gene of interest is substantially exclusively (i.e. essentially entirely) in the pollen of a plant, and is negligible in all other plant parts. By "CDPK," it is meant a plant protein kinase which has a high affinity for calcium, but not calmodulin, and requires calcium, but not calmodulin, for its catalytic activity.

In another nucleic acid of interest, the regulatory element is a root-preferential promoter. A complete description of such a root promoter and the methods for finding one may be found in U.S. Ser. No. 508,207 filed Apr. 12, 1990, the relevant parts of which are herein incorporated by reference. Briefly, a root-preferential promoter was isolated from a gene whose cDNA was found by differential screening of a cDNA library from maize. A cDNA clone so obtained was used to isolate a homologous genomic clone from maize. The protein encoded by the isolated clone was identified as a metallothionein-like protein.

Maize is easily hybridized because of the physical distance between the tassel (male part) and the ear (female part). The method of hybridization first involves the development of inbred lines. Inbred lines are maize plants that are essentially the same genetically from generation to generation. Inbreds are produced by taking the pollen from one maize plant and transferring the pollen to the silk of a receptive maize ear of that same plant. Selections for uniformity and agronomic performance are made and the process is repeated until the seeds from the ears of the plants produce genetically the same plants and the line is pure. A hybrid maize plant is produced by crossing one elite inbred maize plant with one or more other, genetically different and diverse, inbred maize plant. The crossing consists of taking the pollen from one inbred elite maize plant and transferring the pollen to the silk of a receptive ear of the other elite inbred maize plant. The seed from crossing of two inbreds is a first generation hybrid and is called a F1. The F1 of commercially valuable inbreds have better yields, standability, and improvement in other important characteristics than either of the parents. This phenomenon is called hybrid vigor.

In the present invention, commercially-valuable inbred lines of maize are directly transformed through the disclosed methods of delivering nucleic acid sequences of interest to either immature zygotic embryos obtained from such lines or Type I embryogenic callus derived from immature zygotic embryos of such lines. The ability to directly transform maize lines of commercial value is a distinct advantage of the claimed invention in that the generations of backcrossing required when the starting material is not commercially valuable can be avoided, thereby reducing the time and cost of commercialization. Alternatively, the present invention also discloses the direct transformation of hybrids of inbred lines using the claimed methods.

Many hybrid crosses have been successfully made using the transformed, commercially-valuable plants of the claimed invention. For example, the transformed genotype CG00526 of Example 2, below, has been crossed to genotypes CG00689, CG00716, CG00661, CG00642, and LH82 thereby creating hybrids possessing insecticidal activity.

Using the methods of the present invention any hybrid expressing a gene of interest can be created by transforming an inbred line with the gene of interest and using such transformed line to create the hybrid. A transformed hybrid may also be obtained according t o the present invention by directly transforming either immature zygotic embryos obtained from said hybrid plant or by transforming Type I embryogenic callus derived from immature zygotic embryos obtained from said hybrid plant.

In another embodiment of the claimed invention, it is also possible to produce maize plants that have an altered phenotype of anthocyanin pigmentation. This can be accomplished through the use of the disclosed chimeric genes for the constitutive promotion of the genes known as C1 and B-Peru. That activation of the biosynthetic pathway for anthocyanin can be achieved in this way in embryogenic callus was reported by Goff et al., *EMBO Journal*, 9: 2517–2522, 1990. In the present invention, the above said genes were used to produce plants and progeny according to the claimed method whose color phenotype was altered.

Commercially-valuable maize genotypes having altered color phenotype may have benefit to the process of plant breeding. For example, the use of the monoploid inducing gene known as ig (Kermicle, *Science* 166:1422–1424, 1969) can be used to create a haploid having a paternal nuclear constitution. Monoploid inducers creating a haploid having a maternal nuclear constitution are also known (for example, Coe, *The American Naturalist*, XCIII: 381–382, 1959). Because of the low frequency of such an event, it would be advantageous to have an easily screened color phenotype which would allow the identification of the haploids. By using the claimed method and genes of interest, it is possible to obtain a transformed maize line having pigmented seeds, which can be used with a monoploid inducing line. Haploid seed can then be identified by either the presence or absence of seed pigmentation, depending upon the genotypes and crossing methods used.

Since a variety of altered color phenotypes can be produced by the present invention, examples of which are described below, it is further envisioned that other uses in plant breeding may be found for the claimed plants. As another example of such utility, it is possible to link operably, molecularly, biochemically or genetically, or any combination thereof, the expression of the altered color phenotype with the expression of the insecticidal activity produced by transformation of maize according to the claimed methods. Such a link would allow rapid, visual identification of plants within a segregating population of plants and possessing the gene or gene products. Linkages of the altered color phenotype and genotype to other traits of agronomic interest are also envisioned. The ability to perform such identification would translate into reduced costs and time for the plant breeder.

EXAMPLES

The following examples further describe the materials and methods used in carrying out the invention and the subsequent results.

They are offered by way of illustration, and their recitation should not be considered as a limitation of the claimed invention.

Example 1

Bioassay of Transformed Maize for Insecticidal Activity and Quantitation of an Insecticidal Protein Transformed plants were assayed for insecticidal activity and the presence of a BT protein resulting from the expression of the maize-optimized coding sequence of a synthetic BT gene. The procedure is similar for any maize plant transformed with a BT gene but is described here using as an example a cryIA(b) gene, its expressed product, and resistance to European corn borer.

Insecticidal activity was determined by insect bioassay. One to four 4 cm sections are cut from an extended leaf of a transformed maize plant. Each leaf piece is placed on a moistened filter disc in a 50×9 mm petri dish. Five neonate European corn borer larvae are placed on each leaf piece. Since each plant is sampled multiple times this makes a total of 5–20 larvae per plant. The petri dishes are incubated at 29.5° C. and leaf feeding damage and mortality data are scored at 24, 48, and 72 hours.

Quantitative determination of a cryIA(b) IP in the leaves of transgenic plants is performed using enzyme-linked immunosorbant assays (ELISA) as disclosed in Clark M F, Lister R M, Bar-Joseph M: ELISA Techniques. In: Weissbach A, Weissbach H (eds) Methods in Enzymology 118:742–766, Academic Press, Florida (1986). Immunoaffinity purified polyclonal rabbit and goat antibodies specific for the *B. thuringiensis* subsp. kurstaki IP were used to determine ng IP per mg soluble protein from crude extracts of leaf samples. The sensitivity of the double sandwich ELISA is 1–5 ng IP per mg soluble protein using 50 ug of total protein per ELISA microtiter dish well. Corn extracts were made by grinding leaf tissue in gauze lined plastic bags using a hand held ball-bearing homogenizer (AGDIA, Elkart Ind.) in the presence of extraction buffer (50 mM Na2CO3 pH 9.5, 100 mM NaCl, 0.05% Triton, 0.05% Tween, 1 mM PMSF and 1 $\mu$M leupeptin). Protein determination was performed using the Bio-Rad (Richmond, Calif.) protein assay.

Example 2

Transformation of the CG00526 Genotype of Maize by Direct Bombarding of Immature Zygotic Embryos and Isolation of Transformed Callus with the Use of Phosphinothricin as a Selection Agent Immature embryos for experiment KC-65 were obtained approximately 14 days after self-pollination. The immature zygotic embryos were divided among different target plates containing medium capable of inducing and supporting embryogenic callus formation at 36 immature embryos per plate. The immature zygotic embryos were bombarded with a mixture of the plasmids pCIB3064 and pCIB4431 using the PDS-1000/He device from DuPont. The plasmids were precipitated onto 1 um gold particles essentially according to the published procedure from DuPont, as described above. Each target plate was shot one time with the plasmid and gold preparation. Since the plasmid pCIB3064 contained a chimeric gene coding for resistance to phosphinothricin this substance was used to select transformed cells in vitro. This selection was applied at 3 mg/L one day after bombardment and maintained for a total of 12 weeks. The embryogenic callus so obtained was regenerated in the absence of the selection agent phosphinothricin. Plants were obtained from one isolated line of embryogenic callus and given the Event Number 176. All plants were tested by the chlorophenol red (CR) test for resistance to PPT as described in U.S. patent application Ser. No. 759,243, filed Sep. 13, 1991, the relevant portions of which are hereby incorporated herein by reference. This assay utilizes a pH sensitive indicator dye to show which cells are growing in the presence of PPT. Cells which grow produce a pH change in the media and turn the indicator yellow (from red). Plants expressing the resistance gene to PPT are easily seen in this test. Of the 38 plants regenerated for Event Number 176, eight were positive in this test and 30 were negative. Plants positive by the CR test were assayed by PCR for the presence of the synthetic BT gene. Of the eight positive plants from the CR test, 5 were positive for the presence of the synthetic BT gene, 2 were negative and 1 died during propagation. These five remaining plants were bioassayed and found to be resistant to European Corn Borer. DNA was isolated from plant #11 using standard techniques and analysed by Southern blot analysis. It was found to contain sequences which hybridize with probes generated from the synthetic cryIA(b) gene and with a probe generated from the PAT gene. These results showed integration of these genes into the genome of maize. Plant #11 was shown by ELISA to contain 2,195 ng BT protein per mg soluble protein in the leaf tissue, consistent with the use of the leaf-specific promoter from PEPC operably linked to a synthetic BT gene. Plants resistant to European Corn Borer and expressing the introduced BT gene are transformed.

Example 3

Transformation of the Hi II genotype of Maize by Direct Bombarding of Immature Zygotic Embryos and Isolation of Transformed Callus without the Use of a Selection Agent Ear number ED42 was self-pollinated and immature zygotic embryos were obtained approximately 10 days later. Two hundred and eighty eight immature zygotic embryos were divided among 7 different target plates containing a medium capable of inducing and supporting the formation of embryogenic callus. After two days, the immature zygotic embryos were transferred to the same medium but containing 12% sucrose. After 5 hours, the immature zygotic embryos were bombarded with a mixture of the plasmids pCIB3089, pCIB4430, pCIB4433, pCIB4436 using the PDS-1000/He device from DuPont. The plasmids were precipitated onto 1 um gold particles essentially according to the published procedure from DuPont, as described above. The particles were delivered using burst pressures of 450, 650 and 900 psi of helium. Each target plate was shot twice with the plasmid and gold particle preparation. After overnight incubation, the immature embryos were transferred to fresh maintenance medium containing 2% sucrose. Since the plasmids pCIB3089 and pCIB4436 contain the C1 and B-Peru genes which regulate anthocyanin production, the appearance of red, multicellular sectors on the developing embryogenic callus was used to select and isolate transformed cells, eventually obtaining a homogeneous callus line. Embryogenic callus was regenerated in both the absence and presence of the selection agent phosphinothricin, resistance to which was conferred by a chimeric gene present in plasmid pCIB4433. Plants were obtained from a total of nine isolated embryogenic callus lines and were given the Event Numbers 197, 198, 208, 211, 219, 255, 261, 281 and 284. Leaf tissue from plants from each event were assayed for resistance to European Corn Borer. Plants from Event Numbers 208 and 211 were susceptible to European Corn Borer whereas plants from Event Numbers 197, 198, 219, 255, and 261 were resistant. All the plants that were resistant to European Corn Borer also expressed the introduced, leaf-specific PEPC-promoted synthetic BT gene as evidenced by the detection of BT protein using an ELISA assay. Plants resistant to European Corn Borer and expressing the introduced BT gene are transformed.

Example 4

Transformation of the Hi II Genotype of Maize by Direct Bombarding of Immature Zygotic Embryos and Isolation of Transformed Callus with the Use of Phosphinothricin as a Selection Agent.

Ear number ED47 was self-pollinated and immature zygotic embryos were obtained approximately 10 days later. Approximately two hundred and sixty immature zygotic embryos were divided among 8 different target plates containing a medium capable of inducing and supporting the formation of embryogenic callus. After two days, the immature zygotic embryos were transferred to the same medium but containing 12% sucrose. After 5 hours, the immature zygotic embryos were bombarded with a mixture of the plasmids pCIB3089, pCIB4430, pCIB4433, pCIB4436 using the PDS-1000/He device from DuPont. The plasmids were precipitated onto 1 um gold particles essentially according to the published procedure from DuPont, as described above. The particles were delivered using a burst pressure of 900 psi of helium. Each target plate was shot twice with the plasmid and gold particle preparation. After overnight incubation, the immature embryos were transferred to fresh maintenance medium containing 2% sucrose. Since the plasmid pCIB4433 contained a chimeric gene coding for resistance to phosphinothricin this substance was used to select transformed cells in vitro. The selection agent was applied at 10 mg/L 14 days after gene delivery and increased to 20–40 mg/L after approximately one month. The embryogenic callus so obtained was regenerated in the presence of the selection agent phosphinothricin. Plants were obtained from a total of eleven isolated embryogenic callus lines and were given the Event Numbers 220, 221, 222, 223, 225, 230, 231, 232, 233, 269, 274. Plants from each event were assayed for resistance to European Corn Borer. Leaf tissue of plants from Event Numbers 220, 221, 222, 223, 225, 231 and 233 were resistant. All the plants that were resistant to European Corn Borer also expressed the introduced, leaf-specific PEPC-promoted synthetic BT gene as evidenced by the detection of BT protein using an ELISA assay. Plants resistant to European Corn Borer and expressing the introduced BT gene are transformed. Plants from Event Numbers 230, 232, 269 and 274 were not completely tested.

Example 5

Transformation of the CG00526 Genotype of Maize by Bombarding of Type I Callus Derived from Immature Zygotic Embryos and Isolation of Transformed Callus with the Use of Phosphinothricin as a Selection Agent Type I callus was obtained from immature zygotic embryos using standard culture techniques. For gene delivery, approximately 300 mg of the Type I callus was prepared by chopping with a scalpel blade, rinsing 3 times with standard culture media containing 18% sucrose and immediately placed onto semi-solid culture medium again containing 18% sucrose. After approximately 4 hours, the tissue was bombarded using the PDS-1000/He Biolistic device from DuPont. The plasmids pCIB4430 and pCIB4433 were precipitated onto 1 um gold particles using the standard protocol from DuPont. Approximately 16 hours after gene delivery the callus was transferred to standard culture medium containing 2% sucrose and 10 mg/L phosphinothricin as Basta. The callus was subcultured on selection for 8 weeks, after which surviving and growing callus was transferred to standard regeneration medium for the production of plants.

Example 6

Transformation of the LH51 Genotype of Maize by Bombarding of Type I Callus Derived from Immature zygotic embryos and Isolation of Transformed Callus with the Use of Phosphinothricin as a Selection Agent Type I callus was obtained from immature zygotic embryos using standard culture techniques. For gene delivery, approximately 300 mg of the Type I callus was prepared by chopping with a scalpel blade, rinsing 3 times with standard culture media containing 12% sucrose and immediately placed onto semi-solid culture medium again containing 12% sucrose. After approximately 4 hours, the tissue was bombarded using the PDS-1000/He Biolistic device from DuPont. The plasmids pCIB4430 and pCIB4433 were precipitated onto 1 um gold particles using essentially the standard protocol from DuPont as described above. Approximately 16 hours after gene delivery the callus was transferred to standard culture medium containing 2% sucrose and 1 mg/L phosphinothricin as Basta. The callus was subcultured on selection for 8 weeks, after which surviving and growing callus was transferred to standard regeneration medium for the production of plants.

Example 7

Transformation of the CG00526 Genotype of Maize by Direct Bombarding of Immature Zygotic Embryos and Isolation of Transformed Callus with the Use of Phosphinothricin as a Selection Agent Ear numbers JS21, JS22, JS23, JS24 and JS25 were self-pollinated and immature zygotic embryos were obtained approximately 10 days later. Approximately eight hundred and forty immature zygotic embryos were divided among 14 different target plates containing a medium capable of inducing and supporting the formation of embryogenic callus. The immature zygotic embryos were transferred immediately to the same medium but containing 12% sucrose. After 5 hours, the immature zygotic embryos were bombarded with a mixture of the plasmids pCIB3089, pCIB4433, pCIB4436 using the PDS-1000/He device from DuPont. The plasmids were precipitated onto 1 um gold particles essentially according to the published procedure from DuPont, as described above. The particles were delivered using a burst pressure of 1550 psi of helium. Each target plate was shot twice with the plasmid and gold particle preparation. Since the plasmid pCIB4433 contained a chimeric gene coding for resistance to phosphinothricin this substance was used to select transformed cells in vitro. The selection agent was applied at 10 mg/L on the day of gene delivery and increased to 40 mg/L after approximately one month. The embryogenic callus so obtained was regenerated in the presence of the selection agent phosphinothricin. Plants were obtained from a total of eight isolated embryogenic callus lines and were given the Event Numbers 187, 188, 191, 192, 193, 196, 228 and 229. Plants from each event were assayed for resistance to European Corn Borer. Plants from Event Numbers 191 and 193 exhibited insect resistance in the pith in accordance with the use of the pith-preferred synthetic BT construct. All the plants that were resistant to European Corn Borer also expressed the introduced chimeric BT gene as evidenced by the detection of BT protein in the pith using an ELISA assay. Plants resistant to European Corn Borer and expressing the introduced BT gene are transformed.

Example 8

Transformation of the (H99xFR16)xPa91 Genotype of Maize by Direct Bombarding of Immature Zygotic Embryos and Isolation of Transformed Callus with the Use of Phosphinothricin as a Selection Agent Ear numbers GP5 and JS26 were self-pollinated and immature zygotic embryos were obtained approximately 10 days later. Approximately three hundred and thirty immature zygotic embryos were divided among 5 different target plates containing a medium capable of inducing and supporting the formation of embryogenic callus. After two days the immature zygotic embryos were transferred to the same medium but containing 12% sucrose. After approximately 5 hours, the immature zygotic embryos were bombarded with a mixture of the plasmids pCIB3089, pCIB4430, pCIB4433, pCIB4436 using the PDS-1000/He device from DuPont. The plasmids were precipitated onto 1 um gold particles essentially according to the published procedure from DuPont, as described above. The particles were delivered using a burst pressure of 1300 psi of helium. Each target plate was shot twice with the plasmid and gold particle preparation. Since the plasmid pCIB4433 contained a chimeric gene coding for resistance to phosphinothricin this substance was used to select transformed cells in vitro. The selection agent was applied at 10 mg/L 3 weeks after the day of gene delivery. The embryogenic callus so obtained was regenerated. Plants were obtained from three isolated embryogenic callus lines and were given the Event Numbers 242, 247 and 260. Plants from each event were assayed for resistance to European Corn Borer. Plants from Event Numbers 247 and 260 exhibited insect resistance indicating that they were transformed.

Example 9

Transformation of the CG00526 Genotype of Maize by Direct Bombarding of Immature zygotic embryos and Isolation of Transformed Callus with the Use of Phosphinothricin as a Selection Agent Immature zygotic embryos for the experiment KM-124 were obtained approximately 14 days after self-pollination. Approximately one hundred and five immature zygotic embryos were divided among 4 different target plates containing a medium capable of inducing and supporting the formation of embryogenic callus. The immature zygotic embryos were bombarded with a mixture of the plasmids pCIB4421 and pCIB4433 using the PDS-1000/He device from DuPont.

The plasmids were precipitated onto 1 um gold particles essentially according to the published procedure from DuPont, as described above. The particles were delivered using a burst pressure of 1550 psi of helium. Each target plate was shot once with the plasmid and gold particle preparation. Since the plasmid pCIB4433 contained a chimeric gene coding for resistance to phosphinothricin this substance was used, as Basta, to select transformed cells in vitro. The selection agent was applied at 5 mg/L one day after gene delivery and maintained for a total of 12 weeks. The embryogenic callus so obtained was regenerated in the absence of the selection agent phosphinothricin. Plants were obtained from one isolated embryogenic callus line and was given the Event Number 268. Plants were assayed for resistance to European Corn Borer. One of the 5 plants obtained is resistant to European Corn Borer and is transformed.

Example 10

Figure 2:
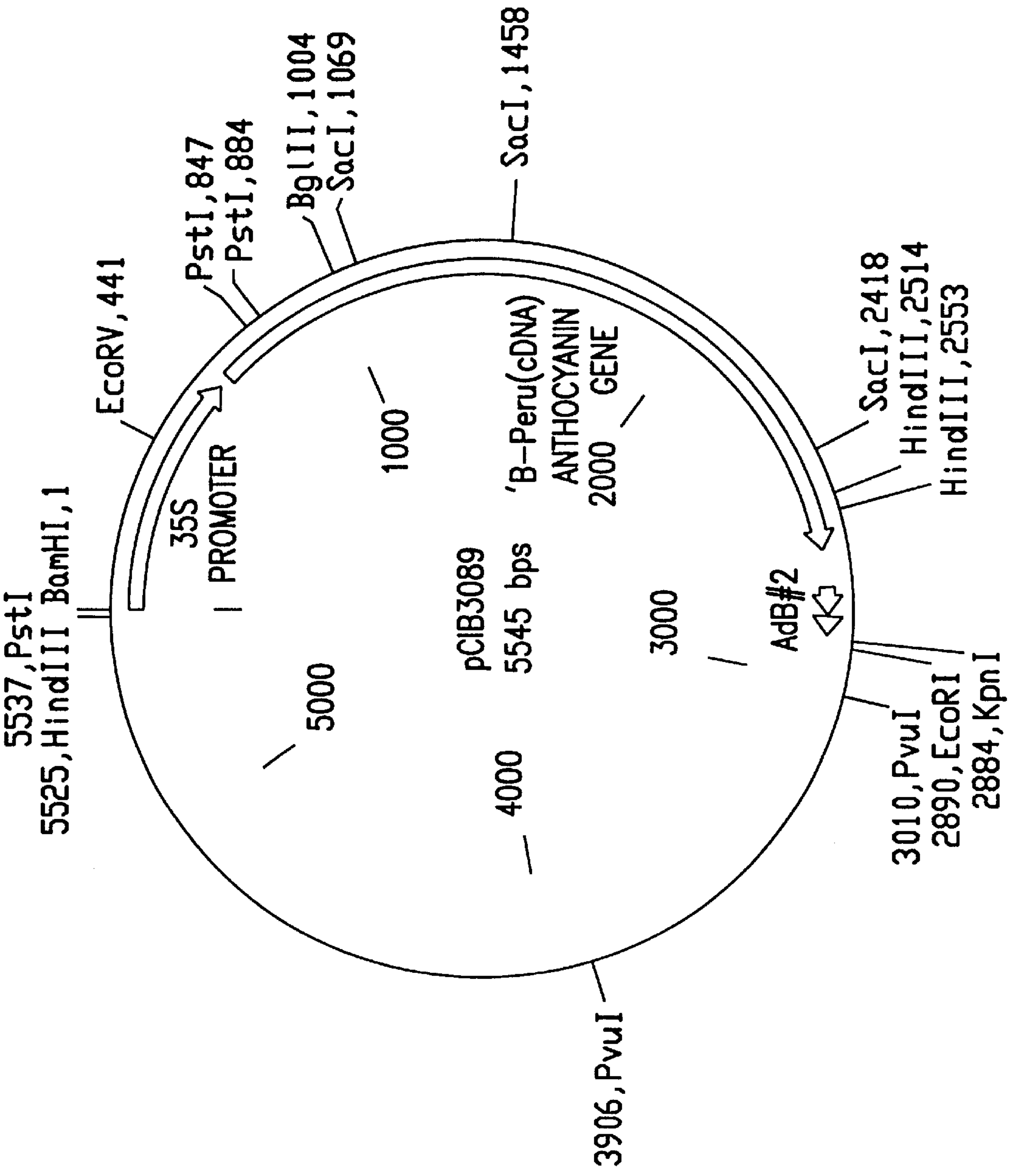
FIG. 2 shows the plasmid map of the vector pCIB3089 containing the 35S/B-Peru chimeric gene.
Figure 3:
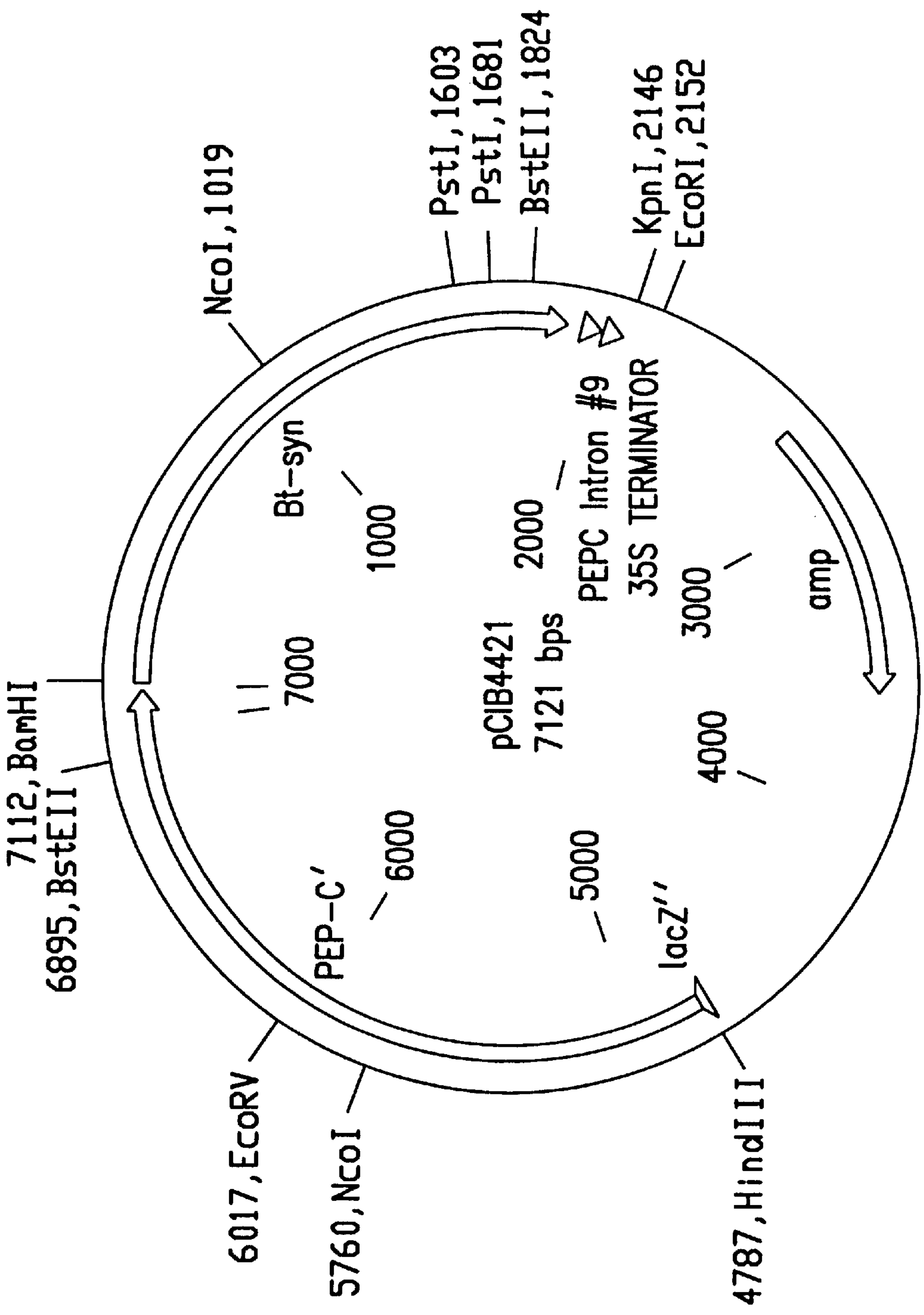
FIG. 3 shows the plasmid map of the vector pCIB4421 containing the PEP Carboxylase promoter fused to the synthetic BT coding sequence (SEQ ID NO: 5).
Figure 4:
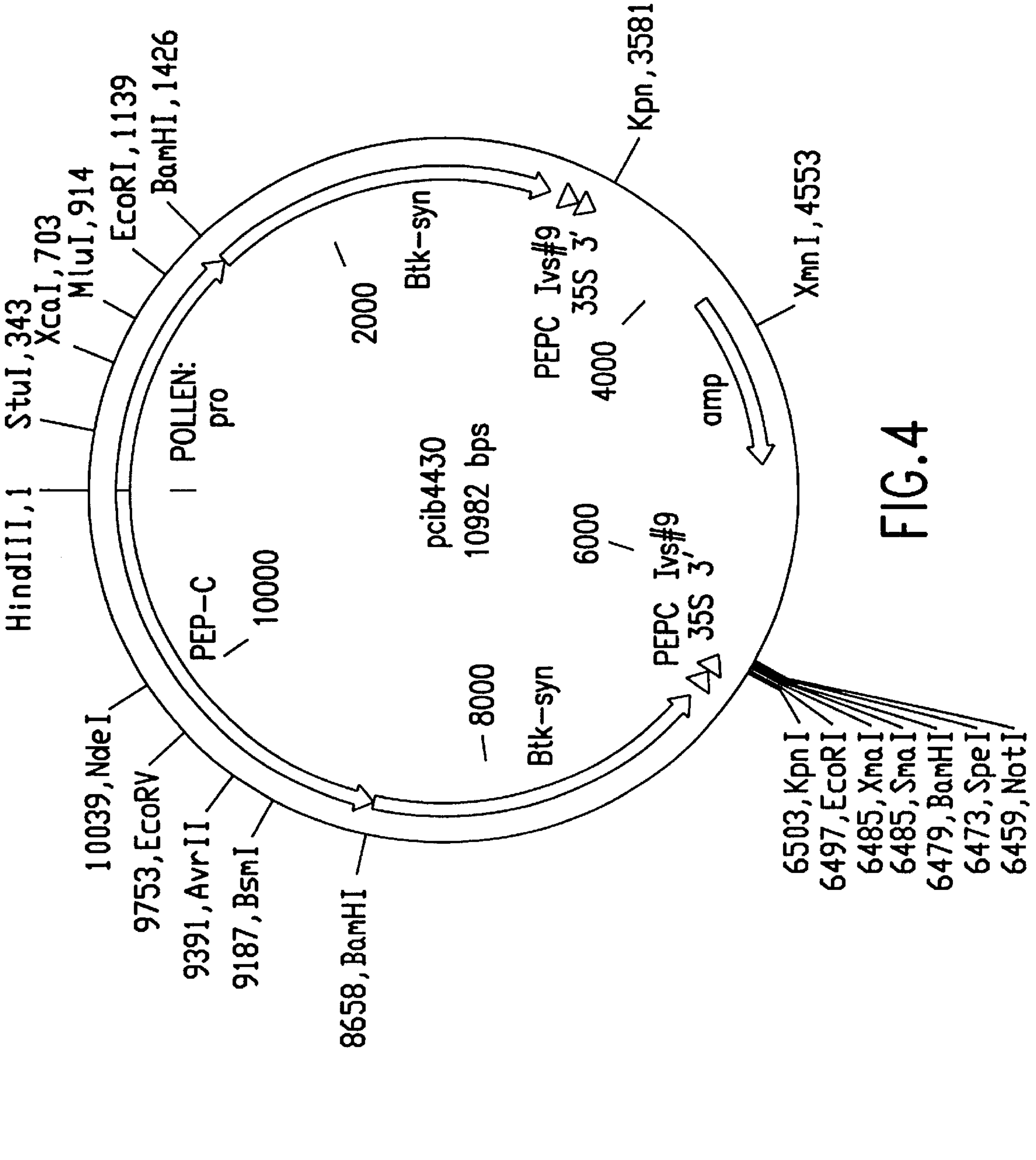
FIG. 4 shows the plasmid map of the vector pCIB4430 containing the pollen-specific promoter fused to the synthetic BT coding sequence (SEQ ID NO: 5).
Figure 5:
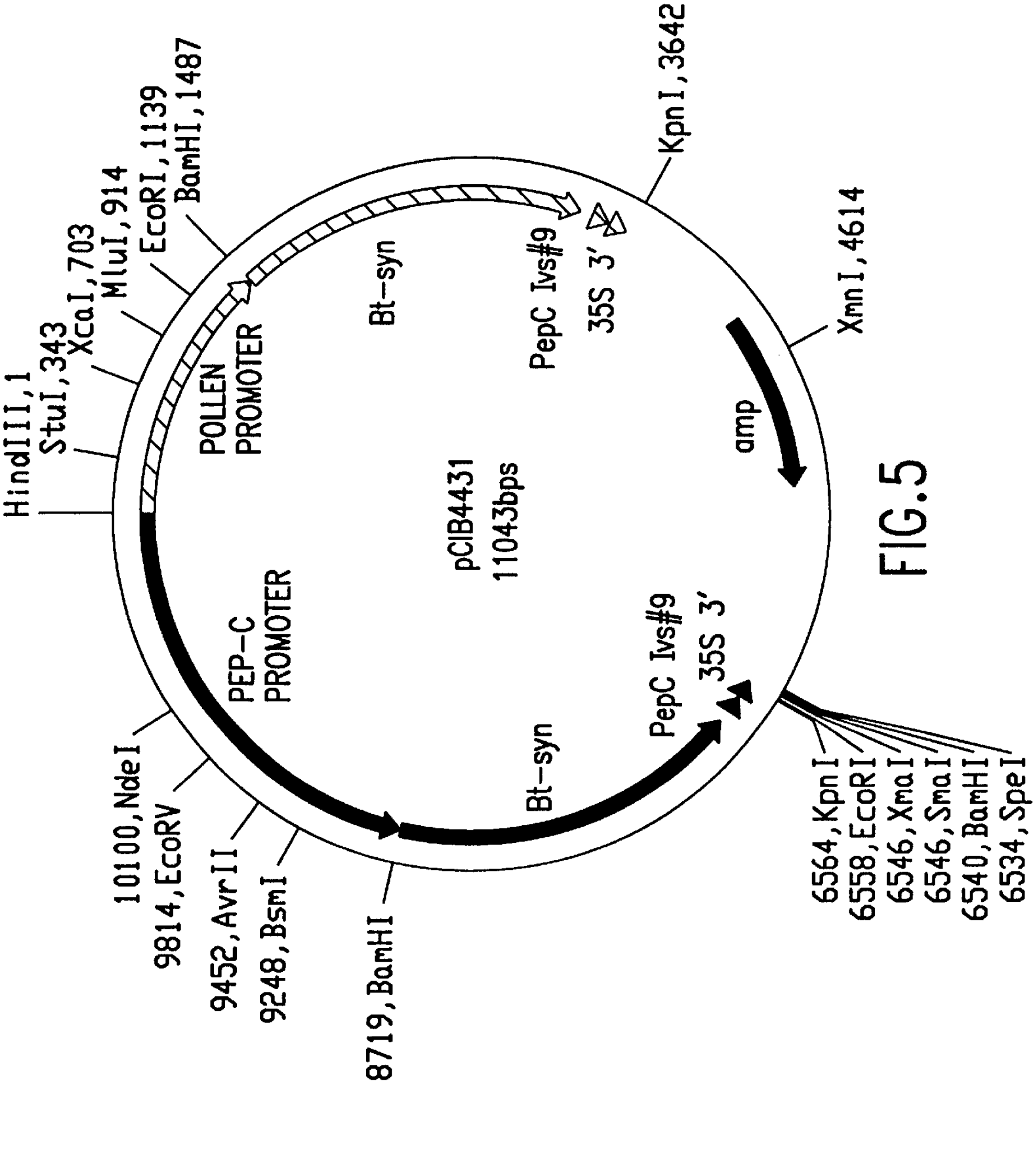
FIG. 5 shows the plasmid map of the vector pCIB4431 containing the pollen-specific promoter fused to the synthetic BT coding sequence (SEQ ID NO: 5) and the PEP Carboxylase promoter fused to the synthetic BT coding sequence (SEQ ID NO: 5).
Figure 6:
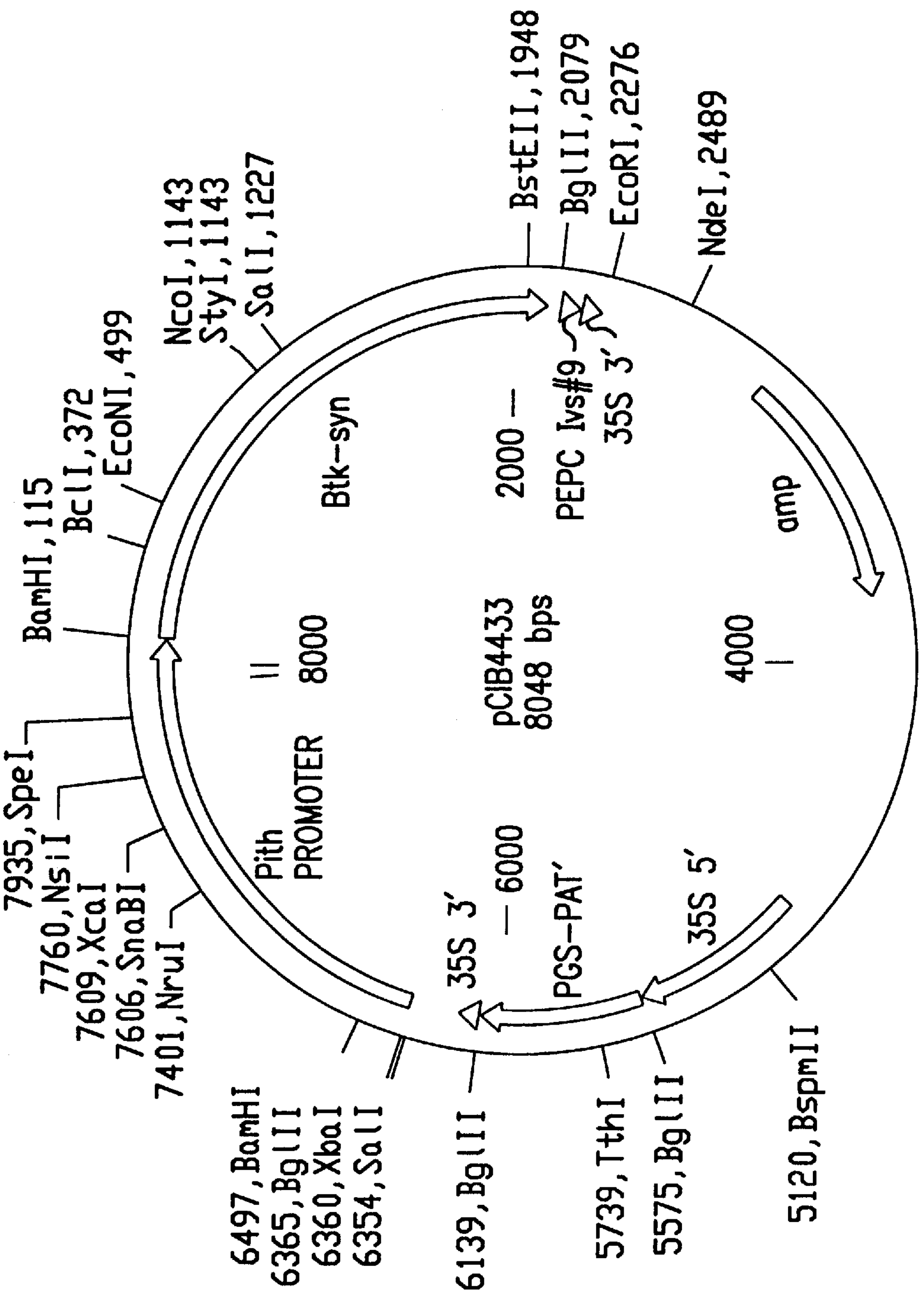
FIG. 6 shows the plasmid map of the vector pCIB4433 containing the pith-preferred promoter fused to the synthetic BT coding sequence (SEQ ID NO: 5) and the 35S/bar chimeric gene.
Figure 7:
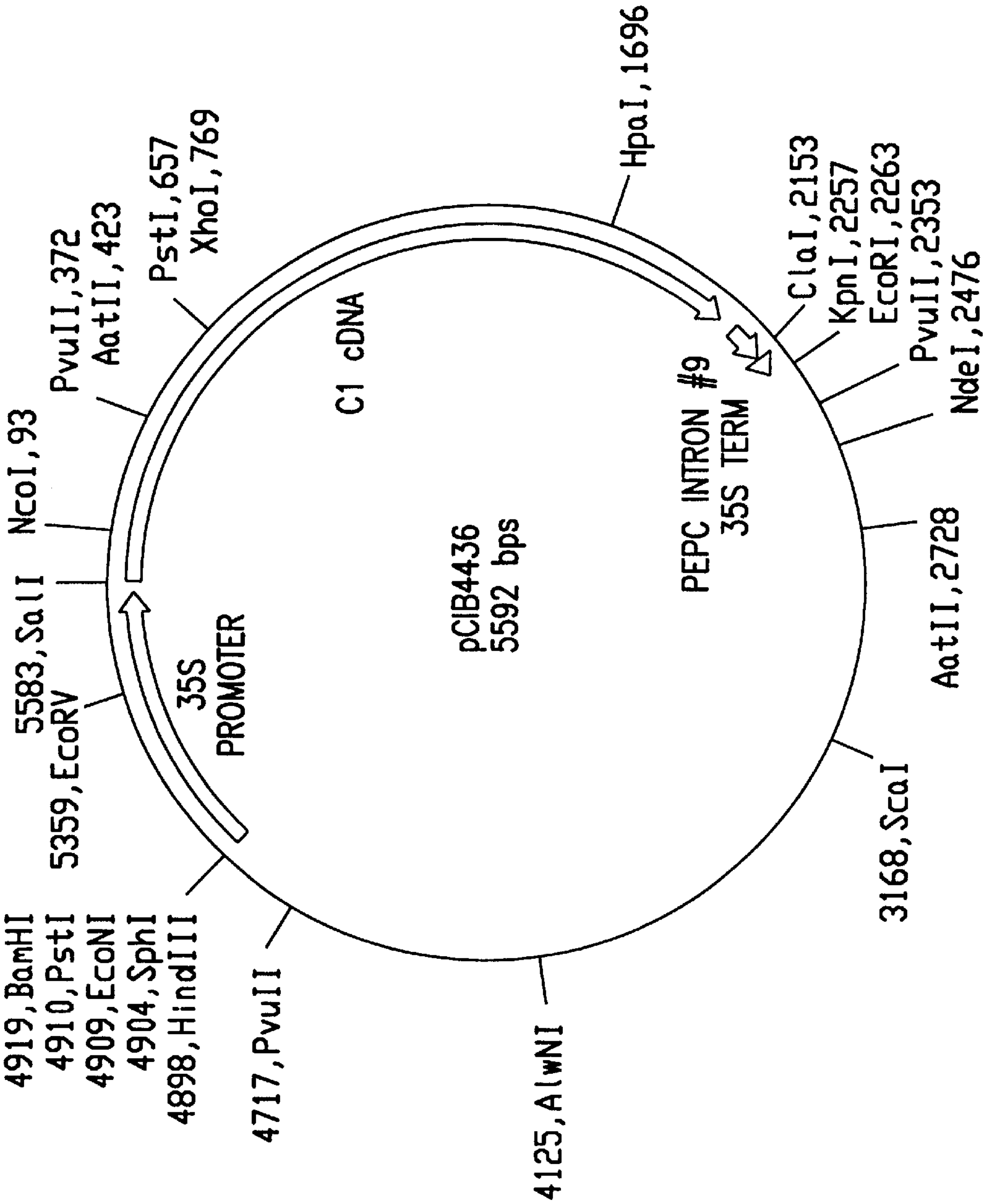
FIG. 7 shows the plasmid map of the vector pCIB4436 containing the 35S/C1 chimeric gene.

Color Phenotypes Exhibited by Plants Transformed with the C1 and B-Peru Coding Sequences According to the Claimed Methods Both genotypes Hi II and CG00526 were transformed with the C1 and B-Peru chimeric genes recited above in FIGS. 2 and 7. A variety of stably expressed altered color phenotypes were obtained, a partial listing of which appears in Table IV, below.

TABLE IV

| BT Event Number | Color Phenotype |
|---|---|
| 197 | Red roots, red anthers |
| 208 | Red roots |
| 211 | Red roots |
| 213 | Red stripe shoot |
| 204 | Red anthers, pink silks |
| 210 | Red stripe shoot, red root, red anther, red silk, red embryo |
| 239 | Red shoot, red root, red silk, normal embryo |
| 207 | Red anthers, red silks |

All publications and patent applications mentioned in this specification are indicative of the level of skill of those skilled in the art to which this invention pertains. All publications and patent applications are herein incorporated by reference to the same extent as if each individual publication or patent plication was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A fertile transgenic maize plant comprising:

a foreign DNA sequence encoding a *Bacillus thuringiensis* insecticidal protein toxic to European corn borer stably incorporated into the plant's genome, the foreign DNA comprising a nucleic acid coding sequence modified from the nucleic acid coding sequence of the native *Bacillus thuringiensis* gene encoding the insecticidal protein to increase expression of the insecticidal protein in the transgenic plant;

wherein the transgenic plant expresses the insecticidal protein in plant leaf tissue at greater than about 1–5 ng insecticidal protein per mg soluble leaf protein, and the leaf tissue causes mortality to European corn borer.

2. The fertile transgenic maize plant according to claim 1, wherein the transgenic plant expresses the insecticidal protein in plant leaf tissue at greater than about 1 ng insecticidal protein per mg soluble leaf protein.

3. The fertile transgenic maize plant according to claim 1, wherein the transgenic plant leaf tissue causes 100% mortality to European corn borer in insect bioassays.

4. The fertile transgenic maize plant according to claim 1, wherein the transgenic plant leaf tissue causes 95% mortality to European corn borer in insect bioassays.

5. The fertile transgenic maize plant according to claim 1, wherein the transgenic plant leaf tissue causes 90% mortality to Europe an corn borer in insect biossays.

6. The fertile transgenic maine plant according to claim 1, wherein the transgenic plant leaf tissue causes 85% mortality to European corn borer in insect bioassays.

7. The fertile transgenic maize plant according to claim 1, wherein the transgenic plant leaf tissue causes 80% mortality to European corn borer in insect bioassays.

8. The fertile transgenic maize plant according to claim 1, wherein the transgenic plant leaf tissue causes 75% mortality to European corn borer in insect bioassays.

9. The fertile transgenic maize plant according to claim 1, wherein the transgenic plant leaf tissue causes 70% mortality to European corn borer in insect bioassays.

10. The fertile transgenic maize plant according to claim 1, wherein the transgenic plant leaf tissue causes 65% mortality to European corn borer in insect bioassays.

11. The fertile transgenic maize plant according to claim 1, wherein the foreign DNA nucleic acid coding sequence has a G+C content of at least about 60% percent.

12. The fertile transgenic maize plant according to claim 1, wherein the foreign DNA nucleic acid coding sequence has a G+C content of at least about 64% percent.

13. The fertile transgenic maize plant according to claim 1, wherein the foreign DNA sequence encodes a CryIA(b) protein.

14. The fertile transgenic maize plant according to claim 1, wherein the foreign DNA sequence encodes a CryIB protein.

15. The fertile transgenic maize plant according to claim 1, wherein the transgenic plant expresses the insecticidal protein at a level sufficient to control a field population of European corn borer below a level of 0.5 eggmass/maize plant.

16. The fertile transgenic maize plant according to claim 1, wherein the transgenic plant expresses the insecticidal protein at a level sufficient to control a field population of European corn borer below a level of about 10 larvae/plant.

17. The fertile transgenic maize plant according to claim 1, wherein the foreign DNA nucleic acid coding sequence has at least about 90% homology with a nucleic acid coding sequence of a native *Bacillus thuringiensis* insecticidal protein that has been modified to contain 100% maize preferred cordons.

18. The fertile transgenic maize plant according to claim 1, wherein the foreign DNA nucleic acid coding sequence has at least about 90% homology with a nucleic acid coding sequence of an active toxin portion of a native *Bacillus thuringiensis* insecticidal protein, which active portion has been modified to contain 100% maize preferred codons.

19. The fertile transgenic maize plant according to any one of claims 1–18, which is an inbred plant.

20. The fertile transgenic maize plant according to any one of claims 1–18, which is a hybrid plant.

21. A method of controlling infestation of maize plants by European corn borer, the method comprising:

providing a transgenic maize plant according to claim 1; and contacting said European corn borer with the plant.

22. A fertile transgenic maize plant comprising:

a foreign DNA sequence encoding a *Bacillus thuringiensis* insecticidal protein toxic to sugarcane borer stably incorporated into the plant's genome the foreign DNA comprising a nucleic acid coding sequence modified from the nucleic acid coding sequence of the native *Bacillus thuringiensis* gene encoding the insecticidal protein to increase expression of the insecticidal protein;

wherein the transgenic plant expresses the insecticidal protein in plant leaf tissue at greater than about 1–5 ng insecticidal protein per mg soluble leaf protein, and the leaf tissue causes mortality to sugarcane borer.

23. The fertile transgenic maize plant according to claim 22, wherein the transgenic plant leaf tissue causes 100% mortality to sugarcane borer in insect bioassays.

24. The fertile transgenic maize plant according to claim 22, wherein the transgenic plant leaf tissue causes 80% mortality to sugarcane borer in insect bioassays.

25. The fertile transgenic maize plant according to claim 22, wherein the transgenic plant expresses the insecticidal protein in plant leaf tissue at greater than about 1 ng insecticidal protein per mg soluble leaf protein.

26. The fertile transgenic maize plant according to claims 22, which is an inbred plant.

27. The fertile transgenic maize plant according to claims 22, which is a hybrid plant.

28. A method of controlling infestation of maize plants by sugarcane borer, the method comprising:

providing a transgenic maize plant according to claims 22; and contacting said sugarcane borer with the plant.

29. A method for producing a stably transformed fertile maize plant, said method comprising:

contacting a maize immature zygotic embryo with a nutrient medium which initiates and supports the formation of embryogenic calli on said immature zygotic embryo;

delivering a nucleic acid sequence by microprojectile bombardment to said immature zygotic embryo within 14 days after said contacting step, wherein said nucleic acid comprises the sequence of SEQ ID NO: 1, 3, 5, 6, 7, 9, or 11;

culturing said immature zygotic embryo in a maintenance medium that supports the growth of embryogenic callus on said zygotic embryo;

selecting a transformed callus from said embryogenic callus; and, regenerating from said transformed callus said fertile stably transformed maize plant, wherein said nucleic acid sequence is inherited by a progeny plant thereof.

30. The method of claim 29 wherein before delivering said nucleic acid said immature zygotic embryo is plasmolyzed by pretreatment with an osmotically-active substance while in the presence of said nutrient medium.

31. The method of claim 30 wherein said osmotically-active substance is sucrose, sorbitol, polyethylene glycol, glucose or mannitol.

32. The method of claim 29 wherein said coding sequence is operably linked to a promoter selected from a pith-preferred promoter, a pollen-specific promoter, a PEP Carboxylase promoter or a root-preferred promoter.

33. The method of claim 29 wherein said nucleic acid sequence comprises a coding sequence for the regulatory proteins known as C1 and B-Peru which control anthocyanin expression.

34. The method of claim 29 wherein the transformed callus is selected visually using the expression of anthocyanin controlled by the introduced genes.

35. The method of claim 29 wherein said immature zygotic embryo is from a maize plant of the genotype CG00716, CG00637, CG00642, CG00623, CG00675, CG00678, CG00653, CG00683, CG00685, CG00686, CG00656, CG00657, CG00661, CG00632, CG00662, CG00712 or CG00684.

36. A method for producing a stably transformed fertile maize plant, said method comprising:

delivering a nucleic acid sequence by microprojectile bombardment to a maize Type I embryogenic callus wherein said nucleic acid comprises the sequence of SEQ ID NO: 1 , 3, 5, 6, 7, 9, or 11;

selecting a transformed callus from said Type I embryogenic callus; and, regenerating from said transformed callus said fertile stably transformed maize plant, wherein said nucleic acid sequence is inherited by a progeny plant thereof.

37. The method of claim 36 wherein before delivering said nucleic acid said maize Type I embryogenic callus is plasmolyzed by pretreatment with an osmotically-active substance while in the presence of a nutrient medium.

38. The method of claim 37 wherein said osmotically-active substance is sucrose, sorbitol, polyethylene glycol, glucose, or mannitol.

39. The method of claim 36 wherein said coding sequence is operably linked to a promoter selected from a pith-preferred promoter, a pollen-specific promoter, a PEP Carboxylase promoter or a root-preferred promoter.

40. The method of claim 36 wherein said nucleic acid sequence comprises a coding sequence for the regulatory proteins known as C1 and B-Peru which control anthocyanin expression.

41. The method of claim 29 wherein said maize Type I embryogenic callus is derived from a maize plant of the genotype CG00716, CG00637, CG00642, CG00623, CG00675, CG00678, CG00653, CG00683, CG00685, CG00686, CG00656, CG00657, CG00661, CG00632, CG00662, CG00712 or CG00684.

42. The method of claim 40 wherein the transformed callus is selected visually using the expression of anthocyanin controlled by the introduced genes.

* * * * *

UNITED STATES PATENT AND TRADEMARK OFFICE

CERTIFICATE OF CORRECTION

PATENT NO. : 6,403,865 B1
DATED : June 11, 2002
INVENTOR(S) : Koziel et al.

It is certified that error appears in the above-identified patent and that said Letters Patent is hereby corrected as shown below:

Title page,
Item [75], Inventors, the inventors' addresses should appear as follows:

| | |
|---|---|
| Michael G. Koziel: | Raleigh, NC |
| Nalini M.Desai | Chapel Hill, NC |
| Kelly S. Lewis | Cary, NC |
| Vance C. Kramer | Hillsborough, NC |
| Gregory W. Warren | Apex, NC |
| Stephen V. Evola | Cary, NC |
| Lyle D. Crossland | Chesterfield, MO |
| Martha S. Wright | Overland Park, KS |
| Ellis J. Merlin | Raleigh, NC |
| Karen L. Launis | Franklinton, NC |
| Steven J. Rothstein | Clive, IA |
| Cindy G. Bowman | Raleigh, NC |
| John L. Dawson | Greensboro, NC |
| Erik M. Dunder | Hillsborough, NC |
| Gary M. Pace | Cary, NC |
| Janet L. Suttie | Raleigh, NC |
| Nadine Carozzi | Raleigh, NC |
| Annick De Framond | Research Triangle Park, NC |
| James O. Linder | Owatonna, MN |
| Robert L. Miller | Iowa City, IA |
| Bruce W. Skillings | Ontario, Canada |
| Alan W. Mousel | Northfield, MN |
| Albert R. Hornbrook | Normal, IL |
| Christopher P. Clucas | Rochelle, IL |
| Moez Rajabali Meghji | Bloomington, IL |
| Andreas H. Tanner | Plaisance Du Touch, France |
| Francis E. Cassagne | Auch, France |
| Gilles Pollini | L'Isle En Dodon, France |
| Terry Ray Colbert | Fort Branch, IN |
| Francis P. Cammack | Rochelle, IL |

Item [56], References Cited, U.S. PATENT DOCUMENTS, delete "Lan" and substitute therefor -- Lam --

UNITED STATES PATENT AND TRADEMARK OFFICE

CERTIFICATE OF CORRECTION

PATENT NO. : 6,403,865 B1
DATED : June 11, 2002
INVENTOR(S) : Koziel et al.

It is certified that error appears in the above-identified patent and that said Letters Patent is hereby corrected as shown below:

Column 1,
Lines 13-15, delete “application” and substitute therefor -- Application -- (2 instances).

Column 3,
Insert the following paragraph between lines 9 and 10:

Examples of commercially important genotypes include the following CG00716; CG00637; CG00642; CG00623; CG00675; CG00678; CG00653; CG00683; CG00685; CG00686; CG00656; CG00657; CG00661; CG00632; CG00662; CG00712; and CG00684. As set forth in the chart below, deposits for each of these genotypes have been made with American Type Culture Collection (ATCC), 12301 Parklawn Drive, Rockville, Maryland 20852, USA, and Intellectual Depository Authority (IDA). The charts shows the Genotype, the ATCC Deposit No., and the Deposit Date:

| Genotype | ATCC Deposit No. | Deposit Date |
|---|---|---|
| CG00716 | 75402 | 01/21/1993 |
| CG00637 | 75166 | 01/27/1991 |
| CG00642 | 75380 | 12/16/1992 |
| CG00623 | 75163 | 11/27/1991 |
| CG00675 | 75381 | 12/16/1992 |
| CG00678 | 75382 | 12/16/1992 |
| CG00653 | 75161 | 11/27/1991 |
| CG00683 | 75383 | 12/16/1992 |
| CG00685 | 75384 | 12/16/1992 |
| CG00686 | 75385 | 12/16/1992 |
| CG00656 | 75160 | 11/27/1991 |
| CG00657 | 75164 | 11/27/1991 |
| CG00661 | 75234 | 04/30/1992 |
| CG00632 | 75162 | 11/27/1991 |
| CG00662 | 75386 | 12/16/1992 |
| CG00712 | 75400 | 01/22/1993 |
| CG00684 | 75401 | 01/22/1993 |

UNITED STATES PATENT AND TRADEMARK OFFICE

CERTIFICATE OF CORRECTION

PATENT NO. : 6,403,865 B1
DATED : June 11, 2002
INVENTOR(S) : Koziel et al.

It is certified that error appears in the above-identified patent and that said Letters Patent is hereby corrected as shown below:

Column 5,
Table III, line 6, delete "Z,4-D" and substitute therefor -- 2,4-D --.

Column 11,
Line 8, delete "subnit" and substitute therefor -- subunit --.

Column 12,
Line 15, delete "t o" and substitute therefor -- to --.

Column 95,
Line 13, delete "Europe an" and substitute therefor -- European --.
Line 55, delete "cordons" and substitute therefor -- codons --.

Column 96,
Line 6, insert a comma after "genome".
Line 25, delete "claims" and substitute therefor -- claim --;
Line 27, delete "claims" and substitute therefor -- claim --; and
Line 31, delete "claims" and substitute therefor -- claim --.

Column 98,
Line 13, delete "claim 29" and substitute therefor -- claim 36 --.

Signed and Sealed this

Tenth Day of June, 2003

JAMES E. ROGAN
*Director of the United States Patent and Trademark Office*

Disclaimer

6,403,865 — Michael G. Koziel; Nalini M. Desai, both of Cary ; Kelly S. Lewis; Vance C. Kramer, both of Hillsborough; Gregory W. Warren, Cary; Stephen V. Evola, Apex; Lyle D. Crossland, Chapel Hill; Martha S. Wright, Cary; Ellis J. Merlin, Raleigh; Karen L. Launis, Franklinton, All of NC (US); Steven J. Rothstein; Guelph (CA); Cindy G. Bowman, Cary, NC (US); John L. Dawson; Erik M. Dunder, both of Chapel Hill, NC (US); Gary M. Pace, Cary, NC (US); Janet Suttie, Raleigh NC (US); Nadine Carozzi, Raleigh, NC (US); Annick De Framond, Durham, NC (US); James O. Linder, Owatonna, MN (US); Robert L. Miller, Cedar Rapids, IA (US); Bruce W. Skillings, Innerkip (CA); Alan W. Mousel, Bluffton, IN (US); Albert R. Hornbrook, Bloomington, IL (US); Christopher P. Clucas, Washington Court House, OH (US); Moez Rajabali Meghji, Bloomington, IL, (US); Andreas H. Tanner, Pleasance du Touch (FR); Francis E. Cassagne, Auch (FR); Gilles Pollini, L'Isle en Dodon (FR); Terry R. Colbert, Troy, TN (US); Francis P. Cammack, Rochelle, IL (US); METHOD OF PRODUCING TRANSGENIC MAIZE USING DIRECT TRANFORMATION OF COMMERICALLY IMPORTANT GENOTYPES. Patent dated Jun. 11, 2002. Disclaimer filed Dec. 13, 2004 by the Assignee, Syngenta Investment Corp.

The term of this patent, subsequent to patent number 08/008,374, filed Jan. 25, 1993, 08/438,666 filed May 10, 1995 and 6,403,865 issued on June 11, 2002 has been disclaimed.

*(Official Gazette May 10, 2005)*

SEQUENCE LISTING

```
(1) GENERAL INFORMATION:

   (iii) NUMBER OF SEQUENCES: 12


(2) INFORMATION FOR SEQ ID NO:1:

     (i) SEQUENCE CHARACTERISTICS:
          (A) LENGTH: 3468 base pairs
          (B) TYPE: nucleic acid
          (C) STRANDEDNESS: single
          (D) TOPOLOGY: linear

    (ii) MOLECULE TYPE: Other nucleic acid
          (A) DESCRIPTION:  Full-length hybrid of synthetic
               maize-optimized DNA sequence and native DNA sequence
               encoding a heat stable cryIA(b) protein as contained in
               pCIB4434.

   (iii) HYPOTHETICAL: YES

    (iv) ANTI-SENSE: NO

    (ix) FEATURE:
          (A) NAME/KEY: CDS
          (B) LOCATION: 1..3465

    (xi) SEQUENCE DESCRIPTION: SEQ ID NO:1:

ATG GAC AAC AAC CCC AAC ATC AAC GAG TGC ATC CCC TAC AAC TGC CTG       48
Met Asp Asn Asn Pro Asn Ile Asn Glu Cys Ile Pro Tyr Asn Cys Leu
  1               5                  10                  15

AGC AAC CCC GAG GTG GAG GTG CTG GGC GGC GAG CGC ATC GAG ACC GGC       96
Ser Asn Pro Glu Val Glu Val Leu Gly Gly Glu Arg Ile Glu Thr Gly
             20                  25                  30

TAC ACC CCC ATC GAC ATC AGC CTG AGC CTG ACC CAG TTC CTG CTG AGC      144
Tyr Thr Pro Ile Asp Ile Ser Leu Ser Leu Thr Gln Phe Leu Leu Ser
         35                  40                  45

GAG TTC GTG CCC GGC GCC GGC TTC GTG CTG GGC CTG GTG GAC ATC ATC      192
Glu Phe Val Pro Gly Ala Gly Phe Val Leu Gly Leu Val Asp Ile Ile
     50                  55                  60

TGG GGC ATC TTC GGC CCC AGC CAG TGG GAC GCC TTC CTG GTG CAG ATC      240
Trp Gly Ile Phe Gly Pro Ser Gln Trp Asp Ala Phe Leu Val Gln Ile
 65                  70                  75                  80

GAG CAG CTG ATC AAC CAG CGC ATC GAG GAG TTC GCC CGC AAC CAG GCC      288
Glu Gln Leu Ile Asn Gln Arg Ile Glu Glu Phe Ala Arg Asn Gln Ala
                 85                  90                  95

ATC AGC CGC CTG GAG GGC CTG AGC AAC CTG TAC CAA ATC TAC GCC GAG      336
Ile Ser Arg Leu Glu Gly Leu Ser Asn Leu Tyr Gln Ile Tyr Ala Glu
            100                 105                 110

AGC TTC CGC GAG TGG GAG GCC GAC CCC ACC AAC CCC GCC CTG CGC GAG      384
Ser Phe Arg Glu Trp Glu Ala Asp Pro Thr Asn Pro Ala Leu Arg Glu
        115                 120                 125

GAG ATG CGC ATC CAG TTC AAC GAC ATG AAC AGC GCC CTG ACC ACC GCC      432
Glu Met Arg Ile Gln Phe Asn Asp Met Asn Ser Ala Leu Thr Thr Ala
    130                 135                 140

ATC CCC CTG TTC GCC GTG CAG AAC TAC CAG GTG CCC CTG CTG AGC GTG      480
Ile Pro Leu Phe Ala Val Gln Asn Tyr Gln Val Pro Leu Leu Ser Val
145                 150                 155                 160

TAC GTG CAG GCC GCC AAC CTG CAC CTG AGC GTG CTG CGC GAC GTC AGC      528
Tyr Val Gln Ala Ala Asn Leu His Leu Ser Val Leu Arg Asp Val Ser
                165                 170                 175

GTG TTC GGC CAG CGC TGG GGC TTC GAC GCC GCC ACC ATC AAC AGC CGC      576
Val Phe Gly Gln Arg Trp Gly Phe Asp Ala Ala Thr Ile Asn Ser Arg
            180                 185                 190
```

-continued

```
TAC AAC GAC CTG ACC CGC CTG ATC GGC AAC TAC ACC GAC CAC GCC GTG      624
Tyr Asn Asp Leu Thr Arg Leu Ile Gly Asn Tyr Thr Asp His Ala Val
        195                 200                 205

CGC TGG TAC AAC ACC GGC CTG GAG CGC GTG TGG GGT CCC GAC AGC CGC      672
Arg Trp Tyr Asn Thr Gly Leu Glu Arg Val Trp Gly Pro Asp Ser Arg
    210                 215                 220

GAC TGG ATC AGG TAC AAC CAG TTC CGC CGC GAG CTG ACC CTG ACC GTG      720
Asp Trp Ile Arg Tyr Asn Gln Phe Arg Arg Glu Leu Thr Leu Thr Val
225                 230                 235                 240

CTG GAC ATC GTG AGC CTG TTC CCC AAC TAC GAC AGC CGC ACC TAC CCC      768
Leu Asp Ile Val Ser Leu Phe Pro Asn Tyr Asp Ser Arg Thr Tyr Pro
                245                 250                 255

ATC CGC ACC GTG AGC CAG CTG ACC CGC GAG ATT TAC ACC AAC CCC GTG      816
Ile Arg Thr Val Ser Gln Leu Thr Arg Glu Ile Tyr Thr Asn Pro Val
            260                 265                 270

CTG GAG AAC TTC GAC GGC AGC TTC CGC GGC AGC GCC CAG GGC ATC GAG      864
Leu Glu Asn Phe Asp Gly Ser Phe Arg Gly Ser Ala Gln Gly Ile Glu
        275                 280                 285

GGC AGC ATC CGC AGC CCC CAC CTG ATG GAC ATC CTG AAC AGC ATC ACC      912
Gly Ser Ile Arg Ser Pro His Leu Met Asp Ile Leu Asn Ser Ile Thr
    290                 295                 300

ATC TAC ACC GAC GCC CAC CGC GGC GAG TAC TAC TGG AGC GGC CAC CAG      960
Ile Tyr Thr Asp Ala His Arg Gly Glu Tyr Tyr Trp Ser Gly His Gln
305                 310                 315                 320

ATC ATG GCC AGC CCC GTC GGC TTC AGC GGC CCC GAG TTC ACC TTC CCC     1008
Ile Met Ala Ser Pro Val Gly Phe Ser Gly Pro Glu Phe Thr Phe Pro
                325                 330                 335

CTG TAC GGC ACC ATG GGC AAC GCT GCA CCT CAG CAG CGC ATC GTG GCA     1056
Leu Tyr Gly Thr Met Gly Asn Ala Ala Pro Gln Gln Arg Ile Val Ala
            340                 345                 350

CAG CTG GGC CAG GGA GTG TAC CGC ACC CTG AGC AGC ACC CTG TAC CGT     1104
Gln Leu Gly Gln Gly Val Tyr Arg Thr Leu Ser Ser Thr Leu Tyr Arg
        355                 360                 365

CGA CCT TTC AAC ATC GGC ATC AAC AAC CAG CAG CTG AGC GTG CTG GAC     1152
Arg Pro Phe Asn Ile Gly Ile Asn Asn Gln Gln Leu Ser Val Leu Asp
    370                 375                 380

GGC ACC GAG TTC GCC TAC GGC ACC AGC AGC AAC CTG CCC AGC GCC GTG     1200
Gly Thr Glu Phe Ala Tyr Gly Thr Ser Ser Asn Leu Pro Ser Ala Val
385                 390                 395                 400

TAC CGC AAG AGC GGC ACC GTG GAC AGC CTG GAC GAG ATC CCC CCT CAG     1248
Tyr Arg Lys Ser Gly Thr Val Asp Ser Leu Asp Glu Ile Pro Pro Gln
                405                 410                 415

AAC AAC AAC GTG CCA CCT CGA CAG GGC TTC AGC CAC CGT CTG AGC CAC     1296
Asn Asn Asn Val Pro Pro Arg Gln Gly Phe Ser His Arg Leu Ser His
            420                 425                 430

GTG AGC ATG TTC CGC AGT GGC TTC AGC AAC AGC AGC GTG AGC ATC ATC     1344
Val Ser Met Phe Arg Ser Gly Phe Ser Asn Ser Ser Val Ser Ile Ile
        435                 440                 445

CGT GCA CCT ATG TTC AGC TGG ATT CAC CGC AGT GCC GAG TTC AAC AAC     1392
Arg Ala Pro Met Phe Ser Trp Ile His Arg Ser Ala Glu Phe Asn Asn
    450                 455                 460

ATC ATC CCC AGC AGC CAG ATC ACC CAG ATC CCC CTG ACC AAG AGC ACC     1440
Ile Ile Pro Ser Ser Gln Ile Thr Gln Ile Pro Leu Thr Lys Ser Thr
465                 470                 475                 480

AAC CTG GGC AGC GGC ACC AGC GTG GTG AAG GGC CCC GGC TTC ACC GGC     1488
Asn Leu Gly Ser Gly Thr Ser Val Val Lys Gly Pro Gly Phe Thr Gly
                485                 490                 495

GGC GAC ATC CTG CGC CGC ACC AGC CCC GGC CAG ATC AGC ACC CTG CGC     1536
Gly Asp Ile Leu Arg Arg Thr Ser Pro Gly Gln Ile Ser Thr Leu Arg
```

-continued

```
            500                 505                 510

GTG AAC ATC ACC GCC CCC CTG AGC CAG CGC TAC CGC GTC CGC ATC CGC      1584
Val Asn Ile Thr Ala Pro Leu Ser Gln Arg Tyr Arg Val Arg Ile Arg
        515                 520                 525

TAC GCC AGC ACC ACC AAC CTG CAG TTC CAC ACC AGC ATC GAC GGC CGC      1632
Tyr Ala Ser Thr Thr Asn Leu Gln Phe His Thr Ser Ile Asp Gly Arg
    530                 535                 540

CCC ATC AAC CAG GGC AAC TTC AGC GCC ACC ATG AGC AGC GGC AGC AAC      1680
Pro Ile Asn Gln Gly Asn Phe Ser Ala Thr Met Ser Ser Gly Ser Asn
545                 550                 555                 560

CTG CAG AGC GGC AGC TTC CGC ACC GTG GGC TTC ACC ACC CCC TTC AAC      1728
Leu Gln Ser Gly Ser Phe Arg Thr Val Gly Phe Thr Thr Pro Phe Asn
                565                 570                 575

TTC AGC AAC GGC AGC AGC GTG TTC ACC CTG AGC GCC CAC GTG TTC AAC      1776
Phe Ser Asn Gly Ser Ser Val Phe Thr Leu Ser Ala His Val Phe Asn
            580                 585                 590

AGC GGC AAC GAG GTG TAC ATC GAC CGC ATC GAG TTC GTG CCC GCC GAG      1824
Ser Gly Asn Glu Val Tyr Ile Asp Arg Ile Glu Phe Val Pro Ala Glu
        595                 600                 605

GTG ACC TTC GAG GCC GAG TAC GAC CTG GAG AGG GCT CAG AAG GCC GTG      1872
Val Thr Phe Glu Ala Glu Tyr Asp Leu Glu Arg Ala Gln Lys Ala Val
    610                 615                 620

AAC GAG CTG TTC ACC AGC AGC AAC CAG ATC GGC CTG AAG ACC GAC GTG      1920
Asn Glu Leu Phe Thr Ser Ser Asn Gln Ile Gly Leu Lys Thr Asp Val
625                 630                 635                 640

ACC GAC TAC CAC ATC GAT CAA GTA TCC AAT TTA GTT GAG TGT TTA TCT      1968
Thr Asp Tyr His Ile Asp Gln Val Ser Asn Leu Val Glu Cys Leu Ser
                645                 650                 655

GAT GAA TTT TGT CTG GAT GAA AAA AAA GAA TTG TCC GAG AAA GTC AAA      2016
Asp Glu Phe Cys Leu Asp Glu Lys Lys Glu Leu Ser Glu Lys Val Lys
            660                 665                 670

CAT GCG AAG CGA CTT AGT GAT GAG CGG AAT TTA CTT CAA GAT CCA AAC      2064
His Ala Lys Arg Leu Ser Asp Glu Arg Asn Leu Leu Gln Asp Pro Asn
        675                 680                 685

TTT AGA GGG ATC AAT AGA CAA CTA GAC CGT GGC TGG AGA GGA AGT ACG      2112
Phe Arg Gly Ile Asn Arg Gln Leu Asp Arg Gly Trp Arg Gly Ser Thr
    690                 695                 700

GAT ATT ACC ATC CAA GGA GGC GAT GAC GTA TTC AAA GAG AAT TAC GTT      2160
Asp Ile Thr Ile Gln Gly Gly Asp Asp Val Phe Lys Glu Asn Tyr Val
705                 710                 715                 720

ACG CTA TTG GGT ACC TTT GAT GAG TGC TAT CCA ACG TAT TTA TAT CAA      2208
Thr Leu Leu Gly Thr Phe Asp Glu Cys Tyr Pro Thr Tyr Leu Tyr Gln
                725                 730                 735

AAA ATA GAT GAG TCG AAA TTA AAA GCC TAT ACC CGT TAC CAA TTA AGA      2256
Lys Ile Asp Glu Ser Lys Leu Lys Ala Tyr Thr Arg Tyr Gln Leu Arg
            740                 745                 750

GGG TAT ATC GAA GAT AGT CAA GAC TTA GAA ATC TAT TTA ATT CGC TAC      2304
Gly Tyr Ile Glu Asp Ser Gln Asp Leu Glu Ile Tyr Leu Ile Arg Tyr
        755                 760                 765

AAT GCC AAA CAC GAA ACA GTA AAT GTG CCA GGT ACG GGT TCC TTA TGG      2352
Asn Ala Lys His Glu Thr Val Asn Val Pro Gly Thr Gly Ser Leu Trp
    770                 775                 780

CCG CTT TCA GCC CCA AGT CCA ATC GGA AAA TGT GCC CAT CAT TCC CAT      2400
Pro Leu Ser Ala Pro Ser Pro Ile Gly Lys Cys Ala His His Ser His
785                 790                 795                 800

CAT TTC TCC TTG GAC ATT GAT GTT GGA TGT ACA GAC TTA AAT GAG GAC      2448
His Phe Ser Leu Asp Ile Asp Val Gly Cys Thr Asp Leu Asn Glu Asp
                805                 810                 815

TTA GGT GTA TGG GTG ATA TTC AAG ATT AAG ACG CAA GAT GGC CAT GCA      2496
```

-continued

```
Leu Gly Val Trp Val Ile Phe Lys Ile Lys Thr Gln Asp Gly His Ala
            820                 825                 830

AGA CTA GGA AAT CTA GAA TTT CTC GAA GAG AAA CCA TTA GTA GGA GAA     2544
Arg Leu Gly Asn Leu Glu Phe Leu Glu Glu Lys Pro Leu Val Gly Glu
        835                 840                 845

GCA CTA GCT CGT GTG AAA AGA GCG GAG AAA AAA TGG AGA GAC AAA CGT     2592
Ala Leu Ala Arg Val Lys Arg Ala Glu Lys Lys Trp Arg Asp Lys Arg
    850                 855                 860

GAA AAA TTG GAA TGG GAA ACA AAT ATT GTT TAT AAA GAG GCA AAA GAA     2640
Glu Lys Leu Glu Trp Glu Thr Asn Ile Val Tyr Lys Glu Ala Lys Glu
865                 870                 875                 880

TCT GTA GAT GCT TTA TTT GTA AAC TCT CAA TAT GAT AGA TTA CAA GCG     2688
Ser Val Asp Ala Leu Phe Val Asn Ser Gln Tyr Asp Arg Leu Gln Ala
                885                 890                 895

GAT ACC AAC ATC GCG ATG ATT CAT GCG GCA GAT AAA CGC GTT CAT AGC     2736
Asp Thr Asn Ile Ala Met Ile His Ala Ala Asp Lys Arg Val His Ser
            900                 905                 910

ATT CGA GAA GCT TAT CTG CCT GAG CTG TCT GTG ATT CCG GGT GTC AAT     2784
Ile Arg Glu Ala Tyr Leu Pro Glu Leu Ser Val Ile Pro Gly Val Asn
        915                 920                 925

GCG GCT ATT TTT GAA GAA TTA GAA GGG CGT ATT TTC ACT GCA TTC TCC     2832
Ala Ala Ile Phe Glu Glu Leu Glu Gly Arg Ile Phe Thr Ala Phe Ser
    930                 935                 940

CTA TAT GAT GCG AGA AAT GTC ATT AAA AAT GGT GAT TTT AAT AAT GGC     2880
Leu Tyr Asp Ala Arg Asn Val Ile Lys Asn Gly Asp Phe Asn Asn Gly
945                 950                 955                 960

TTA TCC TGC TGG AAC GTG AAA GGG CAT GTA GAT GTA GAA GAA CAA AAC     2928
Leu Ser Cys Trp Asn Val Lys Gly His Val Asp Val Glu Glu Gln Asn
                965                 970                 975

AAC CAC CGT TCG GTC CTT GTT GTT CCG GAA TGG GAA GCA GAA GTG TCA     2976
Asn His Arg Ser Val Leu Val Val Pro Glu Trp Glu Ala Glu Val Ser
            980                 985                 990

CAA GAA GTT CGT GTC TGT CCG GGT CGT GGC TAT ATC CTT CGT GTC ACA     3024
Gln Glu Val Arg Val Cys Pro Gly Arg Gly Tyr Ile Leu Arg Val Thr
        995                 1000                1005

GCG TAC AAG GAG GGA TAT GGA GAA GGT TGC GTA ACC ATT CAT GAG ATC     3072
Ala Tyr Lys Glu Gly Tyr Gly Glu Gly Cys Val Thr Ile His Glu Ile
    1010                1015                1020

GAG AAC AAT ACA GAC GAA CTG AAG TTT AGC AAC TGT GTA GAA GAG GAA     3120
Glu Asn Asn Thr Asp Glu Leu Lys Phe Ser Asn Cys Val Glu Glu Glu
1025                1030                1035                1040

GTA TAT CCA AAC AAC ACG GTA ACG TGT AAT GAT TAT ACT GCG ACT CAA     3168
Val Tyr Pro Asn Asn Thr Val Thr Cys Asn Asp Tyr Thr Ala Thr Gln
                1045                1050                1055

GAA GAA TAT GAG GGT ACG TAC ACT TCT CGT AAT CGA GGA TAT GAC GGA     3216
Glu Glu Tyr Glu Gly Thr Tyr Thr Ser Arg Asn Arg Gly Tyr Asp Gly
            1060                1065                1070

GCC TAT GAA AGC AAT TCT TCT GTA CCA GCT GAT TAT GCA TCA GCC TAT     3264
Ala Tyr Glu Ser Asn Ser Ser Val Pro Ala Asp Tyr Ala Ser Ala Tyr
        1075                1080                1085

GAA GAA AAA GCA TAT ACA GAT GGA CGA AGA GAC AAT CCT TGT GAA TCT     3312
Glu Glu Lys Ala Tyr Thr Asp Gly Arg Arg Asp Asn Pro Cys Glu Ser
    1090                1095                1100

AAC AGA GGA TAT GGG GAT TAC ACA CCA CTA CCA GCT GGC TAT GTG ACA     3360
Asn Arg Gly Tyr Gly Asp Tyr Thr Pro Leu Pro Ala Gly Tyr Val Thr
1105                1110                1115                1120

AAA GAA TTA GAG TAC TTC CCA GAA ACC GAT AAG GTA TGG ATT GAG ATC     3408
Lys Glu Leu Glu Tyr Phe Pro Glu Thr Asp Lys Val Trp Ile Glu Ile
                1125                1130                1135
```

-continued

```
GGA GAA ACG GAA GGA ACA TTC ATC GTG GAC AGC GTG GAA TTA CTT CTT      3456
Gly Glu Thr Glu Gly Thr Phe Ile Val Asp Ser Val Glu Leu Leu Leu
            1140                1145                1150

ATG GAG GAA TAA                                                      3468
Met Glu Glu
        1155
```

(2) INFORMATION FOR SEQ ID NO:2:

(i) SEQUENCE CHARACTERISTICS:
(A) LENGTH: 1155 amino acids
(B) TYPE: amino acid
(D) TOPOLOGY: linear (ii) MOLECULE TYPE: protein (xi) SEQUENCE DESCRIPTION: SEQ ID NO:2:

```
Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320
```

-continued

```
Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735
```

-continued

```
Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
                805                 810                 815

Leu Gly Val Trp Val Ile Phe Lys Ile Lys Thr Gln Asp Gly His Ala
            820                 825                 830

Arg Leu Gly Asn Leu Glu Phe Leu Glu Glu Lys Pro Leu Val Gly Glu
        835                 840                 845

Ala Leu Ala Arg Val Lys Arg Ala Glu Lys Lys Trp Arg Asp Lys Arg
    850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
                885                 890                 895

Asp Thr Asn Ile Ala Met Ile His Ala Ala Asp Lys Arg Val His Ser
            900                 905                 910

Ile Arg Glu Ala Tyr Leu Pro Glu Leu Ser Val Ile Pro Gly Val Asn
        915                 920                 925

Ala Ala Ile Phe Glu Glu Leu Glu Gly Arg Ile Phe Thr Ala Phe Ser
    930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Glu Gln Asn
                965                 970                 975

Asn His Arg Ser Val Leu Val Val Pro Glu Trp Glu Ala Glu Val Ser
            980                 985                 990

Gln Glu Val Arg Val Cys Pro Gly Arg Gly Tyr Ile Leu Arg Val Thr
        995                 1000                1005

Ala Tyr Lys Glu Gly Tyr Gly Glu Gly Cys Val Thr Ile His Glu Ile
    1010                1015                1020

Glu Asn Asn Thr Asp Glu Leu Lys Phe Ser Asn Cys Val Glu Glu Glu
1025                1030                1035                1040

Val Tyr Pro Asn Asn Thr Val Thr Cys Asn Asp Tyr Thr Ala Thr Gln
                1045                1050                1055

Glu Glu Tyr Glu Gly Thr Tyr Thr Ser Arg Asn Arg Gly Tyr Asp Gly
            1060                1065                1070

Ala Tyr Glu Ser Asn Ser Ser Val Pro Ala Asp Tyr Ala Ser Ala Tyr
        1075                1080                1085

Glu Glu Lys Ala Tyr Thr Asp Gly Arg Arg Asp Asn Pro Cys Glu Ser
    1090                1095                1100

Asn Arg Gly Tyr Gly Asp Tyr Thr Pro Leu Pro Ala Gly Tyr Val Thr
1105                1110                1115                1120

Lys Glu Leu Glu Tyr Phe Pro Glu Thr Asp Lys Val Trp Ile Glu Ile
                1125                1130                1135

Gly Glu Thr Glu Gly Thr Phe Ile Val Asp Ser Val Glu Leu Leu Leu
            1140                1145                1150

Met Glu Glu
```

-continued

1155

(2) INFORMATION FOR SEQ ID NO:3:

(i) SEQUENCE CHARACTERISTICS:
(A) LENGTH: 3546 base pairs
(B) TYPE: nucleic acid
(C) STRANDEDNESS: single
(D) TOPOLOGY: linear (ii) MOLECULE TYPE: Other nucleic acid
(A) DESCRIPTION: Full-length hybrid maize-optimized DNA sequence encoding a heat stable cryIA(b) protein as contained in pCIB5511

(iii) HYPOTHETICAL: YES (iv) ANTI-SENSE: NO (ix) FEATURE:
(A) NAME/KEY: CDS
(B) LOCATION: 1..3543

(xi) SEQUENCE DESCRIPTION: SEQ ID NO:3:

```
ATG GAC AAC AAC CCC AAC ATC AAC GAG TGC ATC CCC TAC AAC TGC CTG       48
Met Asp Asn Asn Pro Asn Ile Asn Glu Cys Ile Pro Tyr Asn Cys Leu
  1               5                  10                  15

AGC AAC CCC GAG GTG GAG GTG CTG GGC GGC GAG CGC ATC GAG ACC GGC       96
Ser Asn Pro Glu Val Glu Val Leu Gly Gly Glu Arg Ile Glu Thr Gly
             20                  25                  30

TAC ACC CCC ATC GAC ATC AGC CTG AGC CTG ACC CAG TTC CTG CTG AGC      144
Tyr Thr Pro Ile Asp Ile Ser Leu Ser Leu Thr Gln Phe Leu Leu Ser
         35                  40                  45

GAG TTC GTG CCC GGC GCC GGC TTC GTG CTG GGC CTG GTG GAC ATC ATC      192
Glu Phe Val Pro Gly Ala Gly Phe Val Leu Gly Leu Val Asp Ile Ile
     50                  55                  60

TGG GGC ATC TTC GGC CCC AGC CAG TGG GAC GCC TTC CTG GTG CAG ATC      240
Trp Gly Ile Phe Gly Pro Ser Gln Trp Asp Ala Phe Leu Val Gln Ile
 65                  70                  75                  80

GAG CAG CTG ATC AAC CAG CGC ATC GAG GAG TTC GCC CGC AAC CAG GCC      288
Glu Gln Leu Ile Asn Gln Arg Ile Glu Glu Phe Ala Arg Asn Gln Ala
                 85                  90                  95

ATC AGC CGC CTG GAG GGC CTG AGC AAC CTG TAC CAA ATC TAC GCC GAG      336
Ile Ser Arg Leu Glu Gly Leu Ser Asn Leu Tyr Gln Ile Tyr Ala Glu
            100                 105                 110

AGC TTC CGC GAG TGG GAG GCC GAC CCC ACC AAC CCC GCC CTG CGC GAG      384
Ser Phe Arg Glu Trp Glu Ala Asp Pro Thr Asn Pro Ala Leu Arg Glu
        115                 120                 125

GAG ATG CGC ATC CAG TTC AAC GAC ATG AAC AGC GCC CTG ACC ACC GCC      432
Glu Met Arg Ile Gln Phe Asn Asp Met Asn Ser Ala Leu Thr Thr Ala
    130                 135                 140

ATC CCC CTG TTC GCC GTG CAG AAC TAC CAG GTG CCC CTG CTG AGC GTG      480
Ile Pro Leu Phe Ala Val Gln Asn Tyr Gln Val Pro Leu Leu Ser Val
145                 150                 155                 160

TAC GTG CAG GCC GCC AAC CTG CAC CTG AGC GTG CTG CGC GAC GTC AGC      528
Tyr Val Gln Ala Ala Asn Leu His Leu Ser Val Leu Arg Asp Val Ser
                165                 170                 175

GTG TTC GGC CAG CGC TGG GGC TTC GAC GCC GCC ACC ATC AAC AGC CGC      576
Val Phe Gly Gln Arg Trp Gly Phe Asp Ala Ala Thr Ile Asn Ser Arg
            180                 185                 190

TAC AAC GAC CTG ACC CGC CTG ATC GGC AAC TAC ACC GAC CAC GCC GTG      624
Tyr Asn Asp Leu Thr Arg Leu Ile Gly Asn Tyr Thr Asp His Ala Val
        195                 200                 205

CGC TGG TAC AAC ACC GGC CTG GAG CGC GTG TGG GGT CCC GAC AGC CGC      672
```

-continued

```
Arg Trp Tyr Asn Thr Gly Leu Glu Arg Val Trp Gly Pro Asp Ser Arg
    210                 215                 220

GAC TGG ATC AGG TAC AAC CAG TTC CGC CGC GAG CTG ACC CTG ACC GTG      720
Asp Trp Ile Arg Tyr Asn Gln Phe Arg Arg Glu Leu Thr Leu Thr Val
225                 230                 235                 240

CTG GAC ATC GTG AGC CTG TTC CCC AAC TAC GAC AGC CGC ACC TAC CCC      768
Leu Asp Ile Val Ser Leu Phe Pro Asn Tyr Asp Ser Arg Thr Tyr Pro
                245                 250                 255

ATC CGC ACC GTG AGC CAG CTG ACC CGC GAG ATT TAC ACC AAC CCC GTG      816
Ile Arg Thr Val Ser Gln Leu Thr Arg Glu Ile Tyr Thr Asn Pro Val
            260                 265                 270

CTG GAG AAC TTC GAC GGC AGC TTC CGC GGC AGC GCC CAG GGC ATC GAG      864
Leu Glu Asn Phe Asp Gly Ser Phe Arg Gly Ser Ala Gln Gly Ile Glu
        275                 280                 285

GGC AGC ATC CGC AGC CCC CAC CTG ATG GAC ATC CTG AAC AGC ATC ACC      912
Gly Ser Ile Arg Ser Pro His Leu Met Asp Ile Leu Asn Ser Ile Thr
    290                 295                 300

ATC TAC ACC GAC GCC CAC CGC GGC GAG TAC TAC TGG AGC GGC CAC CAG      960
Ile Tyr Thr Asp Ala His Arg Gly Glu Tyr Tyr Trp Ser Gly His Gln
305                 310                 315                 320

ATC ATG GCC AGC CCC GTC GGC TTC AGC GGC CCC GAG TTC ACC TTC CCC     1008
Ile Met Ala Ser Pro Val Gly Phe Ser Gly Pro Glu Phe Thr Phe Pro
                325                 330                 335

CTG TAC GGC ACC ATG GGC AAC GCT GCA CCT CAG CAG CGC ATC GTG GCA     1056
Leu Tyr Gly Thr Met Gly Asn Ala Ala Pro Gln Gln Arg Ile Val Ala
            340                 345                 350

CAG CTG GGC CAG GGA GTG TAC CGC ACC CTG AGC AGC ACC CTG TAC CGT     1104
Gln Leu Gly Gln Gly Val Tyr Arg Thr Leu Ser Ser Thr Leu Tyr Arg
        355                 360                 365

CGA CCT TTC AAC ATC GGC ATC AAC AAC CAG CAG CTG AGC GTG CTG GAC     1152
Arg Pro Phe Asn Ile Gly Ile Asn Asn Gln Gln Leu Ser Val Leu Asp
    370                 375                 380

GGC ACC GAG TTC GCC TAC GGC ACC AGC AGC AAC CTG CCC AGC GCC GTG     1200
Gly Thr Glu Phe Ala Tyr Gly Thr Ser Ser Asn Leu Pro Ser Ala Val
385                 390                 395                 400

TAC CGC AAG AGC GGC ACC GTG GAC AGC CTG GAC GAG ATC CCC CCT CAG     1248
Tyr Arg Lys Ser Gly Thr Val Asp Ser Leu Asp Glu Ile Pro Pro Gln
                405                 410                 415

AAC AAC AAC GTG CCA CCT CGA CAG GGC TTC AGC CAC CGT CTG AGC CAC     1296
Asn Asn Asn Val Pro Pro Arg Gln Gly Phe Ser His Arg Leu Ser His
            420                 425                 430

GTG AGC ATG TTC CGC AGT GGC TTC AGC AAC AGC AGC GTG AGC ATC ATC     1344
Val Ser Met Phe Arg Ser Gly Phe Ser Asn Ser Ser Val Ser Ile Ile
        435                 440                 445

CGT GCA CCT ATG TTC AGC TGG ATT CAC CGC AGT GCC GAG TTC AAC AAC     1392
Arg Ala Pro Met Phe Ser Trp Ile His Arg Ser Ala Glu Phe Asn Asn
    450                 455                 460

ATC ATC CCC AGC AGC CAG ATC ACC CAG ATC CCC CTG ACC AAG AGC ACC     1440
Ile Ile Pro Ser Ser Gln Ile Thr Gln Ile Pro Leu Thr Lys Ser Thr
465                 470                 475                 480

AAC CTG GGC AGC GGC ACC AGC GTG GTG AAG GGC CCC GGC TTC ACC GGC     1488
Asn Leu Gly Ser Gly Thr Ser Val Val Lys Gly Pro Gly Phe Thr Gly
                485                 490                 495

GGC GAC ATC CTG CGC CGC ACC AGC CCC GGC CAG ATC AGC ACC CTG CGC     1536
Gly Asp Ile Leu Arg Arg Thr Ser Pro Gly Gln Ile Ser Thr Leu Arg
            500                 505                 510

GTG AAC ATC ACC GCC CCC CTG AGC CAG CGC TAC CGC GTC CGC ATC CGC     1584
Val Asn Ile Thr Ala Pro Leu Ser Gln Arg Tyr Arg Val Arg Ile Arg
        515                 520                 525
```

-continued

```
TAC GCC AGC ACC ACC AAC CTG CAG TTC CAC ACC AGC ATC GAC GGC CGC      1632
Tyr Ala Ser Thr Thr Asn Leu Gln Phe His Thr Ser Ile Asp Gly Arg
    530                 535                 540

CCC ATC AAC CAG GGC AAC TTC AGC GCC ACC ATG AGC AGC GGC AGC AAC      1680
Pro Ile Asn Gln Gly Asn Phe Ser Ala Thr Met Ser Ser Gly Ser Asn
545                 550                 555                 560

CTG CAG AGC GGC AGC TTC CGC ACC GTG GGC TTC ACC ACC CCC TTC AAC      1728
Leu Gln Ser Gly Ser Phe Arg Thr Val Gly Phe Thr Thr Pro Phe Asn
                565                 570                 575

TTC AGC AAC GGC AGC AGC GTG TTC ACC CTG AGC GCC CAC GTG TTC AAC      1776
Phe Ser Asn Gly Ser Ser Val Phe Thr Leu Ser Ala His Val Phe Asn
            580                 585                 590

AGC GGC AAC GAG GTG TAC ATC GAC CGC ATC GAG TTC GTG CCC GCC GAG      1824
Ser Gly Asn Glu Val Tyr Ile Asp Arg Ile Glu Phe Val Pro Ala Glu
        595                 600                 605

GTG ACC TTC GAG GCC GAG TAC GAC CTG GAG AGG GCT CAG AAG GCC GTG      1872
Val Thr Phe Glu Ala Glu Tyr Asp Leu Glu Arg Ala Gln Lys Ala Val
    610                 615                 620

AAC GAG CTG TTC ACC AGC AGC AAC CAG ATC GGC CTG AAG ACC GAC GTG      1920
Asn Glu Leu Phe Thr Ser Ser Asn Gln Ile Gly Leu Lys Thr Asp Val
625                 630                 635                 640

ACC GAC TAC CAC ATC GAT CAA GTA TCC AAT TTA GTT GAG TGT TTA TCT      1968
Thr Asp Tyr His Ile Asp Gln Val Ser Asn Leu Val Glu Cys Leu Ser
                645                 650                 655

GAT GAA TTT TGT CTG GAT GAA AAA AAA GAA TTG TCC GAG AAA GTC AAA      2016
Asp Glu Phe Cys Leu Asp Glu Lys Lys Glu Leu Ser Glu Lys Val Lys
            660                 665                 670

CAT GCG AAG CGA CTT AGT GAT GAG CGG AAT TTA CTT CAA GAT CCA AAC      2064
His Ala Lys Arg Leu Ser Asp Glu Arg Asn Leu Leu Gln Asp Pro Asn
        675                 680                 685

TTT AGA GGG ATC AAT AGA CAA CTA GAC CGT GGC TGG AGA GGA AGT ACG      2112
Phe Arg Gly Ile Asn Arg Gln Leu Asp Arg Gly Trp Arg Gly Ser Thr
    690                 695                 700

GAT ATT ACC ATC CAA GGA GGC GAT GAC GTA TTC AAA GAG AAT TAC GTT      2160
Asp Ile Thr Ile Gln Gly Gly Asp Asp Val Phe Lys Glu Asn Tyr Val
705                 710                 715                 720

ACG CTA TTG GGT ACC TTC GAC GAG TGC TAC CCC ACC TAC CTG TAC CAG      2208
Thr Leu Leu Gly Thr Phe Asp Glu Cys Tyr Pro Thr Tyr Leu Tyr Gln
                725                 730                 735

AAG ATC GAC GAG AGC AAG CTG AAG GCC TAC ACC CGC TAC CAG CTG CGC      2256
Lys Ile Asp Glu Ser Lys Leu Lys Ala Tyr Thr Arg Tyr Gln Leu Arg
            740                 745                 750

GGC TAC ATC GAG GAC AGC CAG GAC CTG GAA ATC TAC CTG ATC CGC TAC      2304
Gly Tyr Ile Glu Asp Ser Gln Asp Leu Glu Ile Tyr Leu Ile Arg Tyr
        755                 760                 765

AAC GCC AAG CAC GAG ACC GTG AAC GTG CCC GGC ACC GGC AGC CTG TGG      2352
Asn Ala Lys His Glu Thr Val Asn Val Pro Gly Thr Gly Ser Leu Trp
    770                 775                 780

CCC CTG AGC GCC CCC AGC CCC ATC GGC AAG TGC GGG GAG CCG AAT CGA      2400
Pro Leu Ser Ala Pro Ser Pro Ile Gly Lys Cys Gly Glu Pro Asn Arg
785                 790                 795                 800

TGC GCT CCG CAC CTG GAG TGG AAC CCG GAC CTA GAC TGC AGC TGC AGG      2448
Cys Ala Pro His Leu Glu Trp Asn Pro Asp Leu Asp Cys Ser Cys Arg
                805                 810                 815

GAC GGG GAG AAG TGC GCC CAC CAC AGC CAC CAC TTC AGC CTG GAC ATC      2496
Asp Gly Glu Lys Cys Ala His His Ser His His Phe Ser Leu Asp Ile
            820                 825                 830

GAC GTG GGC TGC ACC GAC CTG AAC GAG GAC CTG GGC GTG TGG GTG ATC      2544
Asp Val Gly Cys Thr Asp Leu Asn Glu Asp Leu Gly Val Trp Val Ile
        835                 840                 845
```

-continued

TTC AAG ATC AAG ACC CAG GAC GGC CAC GCC CGC CTG GGC AAT CTA GAA 2592
Phe Lys Ile Lys Thr Gln Asp Gly His Ala Arg Leu Gly Asn Leu Glu
850 855 860

TTT CTC GAA GAG AAA CCA TTA GTA GGA GAA GCA CTA GCT CGT GTG AAA 2640
Phe Leu Glu Glu Lys Pro Leu Val Gly Glu Ala Leu Ala Arg Val Lys
865 870 875 880

AGA GCG GAG AAA AAA TGG AGA GAC AAA CGT GAA AAA TTG GAA TGG GAA 2688
Arg Ala Glu Lys Lys Trp Arg Asp Lys Arg Glu Lys Leu Glu Trp Glu
885 890 895

ACA AAT ATT GTT TAT AAA GAG GCA AAA GAA TCT GTA GAT GCT TTA TTT 2736
Thr Asn Ile Val Tyr Lys Glu Ala Lys Glu Ser Val Asp Ala Leu Phe
900 905 910

GTA AAC TCT CAA TAT GAT AGA TTA CAA GCG GAT ACC AAC ATC GCG ATG 2784
Val Asn Ser Gln Tyr Asp Arg Leu Gln Ala Asp Thr Asn Ile Ala Met
915 920 925

ATT CAT GCG GCA GAT AAA CGC GTT CAT AGC ATT CGA GAA GCT TAT CTG 2832
Ile His Ala Ala Asp Lys Arg Val His Ser Ile Arg Glu Ala Tyr Leu
930 935 940

CCT GAG CTG TCT GTG ATT CCG GGT GTC AAT GCG GCT ATT TTT GAA GAA 2880
Pro Glu Leu Ser Val Ile Pro Gly Val Asn Ala Ala Ile Phe Glu Glu
945 950 955 960

TTA GAA GGG CGT ATT TTC ACT GCA TTC TCC CTA TAT GAT GCG AGA AAT 2928
Leu Glu Gly Arg Ile Phe Thr Ala Phe Ser Leu Tyr Asp Ala Arg Asn
965 970 975

GTC ATT AAA AAT GGT GAT TTT AAT AAT GGC TTA TCC TGC TGG AAC GTG 2976
Val Ile Lys Asn Gly Asp Phe Asn Asn Gly Leu Ser Cys Trp Asn Val
980 985 990

AAA GGG CAT GTA GAT GTA GAA GAA CAA AAC AAC CAC CGT TCG GTC CTT 3024
Lys Gly His Val Asp Val Glu Glu Gln Asn Asn His Arg Ser Val Leu
995 1000 1005

GTT GTT CCG GAA TGG GAA GCA GAA GTG TCA CAA GAA GTT CGT GTC TGT 3072
Val Val Pro Glu Trp Glu Ala Glu Val Ser Gln Glu Val Arg Val Cys
1010 1015 1020

CCG GGT CGT GGA TAT ATC CTT CGT GTC ACA GCG TAC AAG GAG GGA TAT 3120
Pro Gly Arg Gly Tyr Ile Leu Arg Val Thr Ala Tyr Lys Glu Gly Tyr
1025 1030 1035 1040

GGA GAA GGT TGC GTA ACC ATT CAT GAG ATC GAG AAC AAT ACA GAC GAA 3168
Gly Glu Gly Cys Val Thr Ile His Glu Ile Glu Asn Asn Thr Asp Glu
1045 1050 1055

CTG AAG TTT AGC AAC TGT GTA GAA GAG GAA GTA TAT CCA AAC AAC ACG 3216
Leu Lys Phe Ser Asn Cys Val Glu Glu Glu Val Tyr Pro Asn Asn Thr
1060 1065 1070

GTA ACG TGT AAT GAT TAT ACT GCG ACT CAA GAA GAA TAT GAG GGT ACG 3264
Val Thr Cys Asn Asp Tyr Thr Ala Thr Gln Glu Glu Tyr Glu Gly Thr
1075 1080 1085

TAC ACT TCT CGT AAT CGA GGA TAT GAC GGA GCC TAT GAA AGC AAT TCT 3312
Tyr Thr Ser Arg Asn Arg Gly Tyr Asp Gly Ala Tyr Glu Ser Asn Ser
1090 1095 1100

TCT GTA CCA GCT GAT TAT GCA TCA GCC TAT GAA GAA AAA GCA TAT ACA 3360
Ser Val Pro Ala Asp Tyr Ala Ser Ala Tyr Glu Glu Lys Ala Tyr Thr
1105 1110 1115 1120

GAT GGA CGA AGA GAC AAT CCT TGT GAA TCT AAC AGA GGA TAT GGG GAT 3408
Asp Gly Arg Arg Asp Asn Pro Cys Glu Ser Asn Arg Gly Tyr Gly Asp
1125 1130 1135

TAC ACA CCA CTA CCA GCT GGC TAT GTG ACA AAA GAA TTA GAG TAC TTC 3456
Tyr Thr Pro Leu Pro Ala Gly Tyr Val Thr Lys Glu Leu Glu Tyr Phe
1140 1145 1150

CCA GAA ACC GAT AAG GTA TGG ATT GAG ATC GGA GAA ACG GAA GGA ACA 3504
Pro Glu Thr Asp Lys Val Trp Ile Glu Ile Gly Glu Thr Glu Gly Thr

-continued

```
        1155                1160                1165

TTC ATC GTG GAC AGC GTG GAA TTA CTT CTT ATG GAG GAA TAA            3546
Phe Ile Val Asp Ser Val Glu Leu Leu Leu Met Glu Glu
    1170                1175                1180
```

(2) INFORMATION FOR SEQ ID NO:4:

(i) SEQUENCE CHARACTERISTICS:
(A) LENGTH: 1181 amino acids
(B) TYPE: amino acid
(D) TOPOLOGY: linear (ii) MOLECULE TYPE: protein (xi) SEQUENCE DESCRIPTION: SEQ ID NO:4:

```
Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
```

-continued

```
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750
```

-continued

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Pro Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
    850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Arg Leu Gln Ala Asp Thr Asn Ile Ala Met
        915                 920                 925

Ile His Ala Ala Asp Lys Arg Val His Ser Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn His Arg Ser Val Leu
        995                 1000                1005

Val Val Pro Glu Trp Glu Ala Glu Val Ser Gln Glu Val Arg Val Cys
    1010                1015                1020

Pro Gly Arg Gly Tyr Ile Leu Arg Val Thr Ala Tyr Lys Glu Gly Tyr
1025                1030                1035                1040

Gly Glu Gly Cys Val Thr Ile His Glu Ile Glu Asn Asn Thr Asp Glu
                1045                1050                1055

Leu Lys Phe Ser Asn Cys Val Glu Glu Glu Val Tyr Pro Asn Asn Thr
            1060                1065                1070

Val Thr Cys Asn Asp Tyr Thr Ala Thr Gln Glu Glu Tyr Glu Gly Thr
        1075                1080                1085

Tyr Thr Ser Arg Asn Arg Gly Tyr Asp Gly Ala Tyr Glu Ser Asn Ser
    1090                1095                1100

Ser Val Pro Ala Asp Tyr Ala Ser Ala Tyr Glu Glu Lys Ala Tyr Thr
1105                1110                1115                1120

Asp Gly Arg Arg Asp Asn Pro Cys Glu Ser Asn Arg Gly Tyr Gly Asp
                1125                1130                1135

Tyr Thr Pro Leu Pro Ala Gly Tyr Val Thr Lys Glu Leu Glu Tyr Phe
            1140                1145                1150

Pro Glu Thr Asp Lys Val Trp Ile Glu Ile Gly Glu Thr Glu Gly Thr
        1155                1160                1165

-continued

Phe Ile Val Asp Ser Val Glu Leu Leu Leu Met Glu Glu
1170 1175 1180

(2) INFORMATION FOR SEQ ID NO:5:

(i) SEQUENCE CHARACTERISTICS:
(A) LENGTH: 1961 base pairs
(B) TYPE: nucleic acid
(C) STRANDEDNESS: single
(D) TOPOLOGY: linear (ii) MOLECULE TYPE: Other nucleic acid
(A) DESCRIPTION: DNA sequence of truncated maize optimized synthetic BT cryIA(b) gene (iii) HYPOTHETICAL: YES (iv) ANTI-SENSE: NO (xi) SEQUENCE DESCRIPTION: SEQ ID NO:5:

GATCCAACAA TGGACAACAA CCCCAACATC AACGAGTGCA TCCCCTACAA CTGCCTGAGC 60

AACCCCGAGG TGGAGGTGCT GGGCGGCGAG CGCATCGAGA CCGGCTACAC CCCCATCGAC 120

ATCAGCCTGA GCCTGACCCA GTTCCTGCTG AGCGAGTTCG TGCCCGGCGC CGGCTTCGTG 180

CTGGGCCTGG TGGACATCAT CTGGGGCATC TTCGGCCCCA GCCAGTGGGA CGCCTTCCTG 240

GTGCAGATCG AGCAGCTGAT CAACCAGCGC ATCGAGGAGT TCGCCCGCAA CCAGGCCATC 300

AGCCGCCTGG AGGGCCTGAG CAACCTGTAC CAAATCTACG CCGAGAGCTT CCGCGAGTGG 360

GAGGCCGACC CCACCAACCC CGCCCTGCGC GAGGAGATGC GCATCCAGTT CAACGACATG 420

AACAGCGCCC TGACCACCGC CATCCCCCTG TTCGCCGTGC AGAACTACCA GGTGCCCCTG 480

CTGAGCGTGT ACGTGCAGGC CGCCAACCTG CACCTGAGCG TGCTGCGCGA CGTCAGCGTG 540

TTCGGCCAGC GCTGGGGCTT CGACGCCGCC ACCATCAACA GCCGCTACAA CGACCTGACC 600

CGCCTGATCG GCAACTACAC CGACCACGCC GTGCGCTGGT ACAACACCGG CCTGGAGCGC 660

GTGTGGGGTC CCGACAGCCG CGACTGGATC AGGTACAACC AGTTCCGCCG CGAGCTGACC 720

CTGACCGTGC TGGACATCGT GAGCCTGTTC CCCAACTACG ACAGCCGCAC CTACCCCATC 780

CGCACCGTGA GCCAGCTGAC CCGCGAGATT TACACCAACC CCGTGCTGGA GAACTTCGAC 840

GGCAGCTTCC GCGGCAGCGC CCAGGGCATC GAGGGCAGCA TCCGCAGCCC CCACCTGATG 900

GACATCCTGA ACAGCATCAC CATCTACACC GACGCCCACC GCGGCGAGTA CTACTGGAGC 960

GGCCACCAGA TCATGGCCAG CCCCGTCGGC TTCAGCGGCC CCGAGTTCAC CTTCCCCCTG 1020

TACGGCACCA TGGGCAACGC TGCACCTCAG CAGCGCATCG TGGCACAGCT GGGCCAGGGA 1080

GTGTACCGCA CCCTGAGCAG CACCCTGTAC CGTCGACCTT TCAACATCGG CATCAACAAC 1140

CAGCAGCTGA GCGTGCTGGA CGGCACCGAG TTCGCCTACG GCACCAGCAG CAACCTGCCC 1200

AGCGCCGTGT ACCGCAAGAG CGGCACCGTG GACAGCCTGG ACGAGATCCC CCCTCAGAAC 1260

AACAACGTGC CACCTCGACA GGGCTTCAGC CACCGTCTGA GCCACGTGAG CATGTTCCGC 1320

AGTGGCTTCA GCAACAGCAG CGTGAGCATC ATCCGTGCAC CTATGTTCAG CTGGATTCAC 1380

CGCAGTGCCG AGTTCAACAA CATCATCCCC AGCAGCCAGA TCACCCAGAT CCCCCTGACC 1440

AAGAGCACCA ACCTGGGCAG CGGCACCAGC GTGGTGAAGG GCCCCGGCTT CACCGGCGGC 1500

GACATCCTGC GCCGCACCAG CCCCGGCCAG ATCAGCACCC TGCGCGTGAA CATCACCGCC 1560

CCCCTGAGCC AGCGCTACCG CGTCCGCATC CGCTACGCCA GCACCACCAA CCTGCAGTTC 1620

CACACCAGCA TCGACGGCCG CCCCATCAAC CAGGGCAACT TCAGCGCCAC CATGAGCAGC 1680

GGCAGCAACC TGCAGAGCGG CAGCTTCCGC ACCGTGGGCT TCACCACCCC CTTCAACTTC 1740

-continued

AGCAACGGCA GCAGCGTGTT CACCCTGAGC GCCCACGTGT TCAACAGCGG CAACGAGGTG 1800

TACATCGACC GCATCGAGTT CGTGCCCGCC GAGGTGACCT TCGAGGCCGA GTACGACCTG 1860

GAGAGGGCTC AGAAGGCCGT GAACGAGCTG TTCACCAGCA GCAACCAGAT CGGCCTGAAG 1920

ACCGACGTGA CCGACTACCA CATCGATCAG GTGTAGGAGC T 1961

(2) INFORMATION FOR SEQ ID NO:6:

(i) SEQUENCE CHARACTERISTICS:
(A) LENGTH: 3508 base pairs
(B) TYPE: nucleic acid
(C) STRANDEDNESS: single
(D) TOPOLOGY: linear (ii) MOLECULE TYPE: Other nucleic acid
(A) DESCRIPTION: DNA sequence of full-length maize optimized synthetic BT cryIA(b) gene (iii) HYPOTHETICAL: YES (iv) ANTI-SENSE: NO (xi) SEQUENCE DESCRIPTION: SEQ ID NO:6:

GATCCAACAA TGGACAACAA CCCCAACATC AACGAGTGCA TCCCCTACAA CTGCCTGAGC 60

AACCCCGAGG TGGAGGTGCT GGGCGGCGAG CGCATCGAGA CCGGCTACAC CCCCATCGAC 120

ATCAGCCTGA GCCTGACCCA GTTCCTGCTG AGCGAGTTCG TGCCCGGCGC CGGCTTCGTG 180

CTGGGCCTGG TGGACATCAT CTGGGGCATC TTCGGCCCCA GCCAGTGGGA CGCCTTCCTG 240

GTGCAGATCG AGCAGCTGAT CAACCAGCGC ATCGAGGAGT TCGCCCGCAA CCAGGCCATC 300

AGCCGCCTGG AGGGCCTGAG CAACCTGTAC CAAATCTACG CCGAGAGCTT CCGCGAGTGG 360

GAGGCCGACC CCACCAACCC CGCCCTGCGC GAGGAGATGC GCATCCAGTT CAACGACATG 420

AACAGCGCCC TGACCACCGC CATCCCCCTG TTCGCCGTGC AGAACTACCA GGTGCCCCTG 480

CTGAGCGTGT ACGTGCAGGC CGCCAACCTG CACCTGAGCG TGCTGCGCGA CGTCAGCGTG 540

TTCGGCCAGC GCTGGGGCTT CGACGCCGCC ACCATCAACA GCCGCTACAA CGACCTGACC 600

CGCCTGATCG GCAACTACAC CGACCACGCC GTGCGCTGGT ACAACACCGG CCTGGAGCGC 660

GTGTGGGGTC CCGACAGCCG CGACTGGATC AGGTACAACC AGTTCCGCCG CGAGCTGACC 720

CTGACCGTGC TGGACATCGT GAGCCTGTTC CCCAACTACG ACAGCCGCAC CTACCCCATC 780

CGCACCGTGA GCCAGCTGAC CCGCGAGATT TACACCAACC CCGTGCTGGA GAACTTCGAC 840

GGCAGCTTCC GCGGCAGCGC CCAGGGCATC GAGGGCAGCA TCCGCAGCCC CCACCTGATG 900

GACATCCTGA ACAGCATCAC CATCTACACC GACGCCCACC GCGGCGAGTA CTACTGGAGC 960

GGCCACCAGA TCATGGCCAG CCCCGTCGGC TTCAGCGGCC CCGAGTTCAC CTTCCCCCTG 1020

TACGGCACCA TGGGCAACGC TGCACCTCAG CAGCGCATCG TGGCACAGCT GGGCCAGGGA 1080

GTGTACCGCA CCCTGAGCAG CACCCTGTAC CGTCGACCTT TCAACATCGG CATCAACAAC 1140

CAGCAGCTGA GCGTGCTGGA CGGCACCGAG TTCGCCTACG GCACCAGCAG CAACCTGCCC 1200

AGCGCCGTGT ACCGCAAGAG CGGCACCGTG GACAGCCTGG ACGAGATCCC CCCTCAGAAC 1260

AACAACGTGC CACCTCGACA GGGCTTCAGC CACCGTCTGA GCCACGTGAG CATGTTCCGC 1320

AGTGGCTTCA GCAACAGCAG CGTGAGCATC ATCCGTGCAC CTATGTTCAG CTGGATTCAC 1380

CGCAGTGCCG AGTTCAACAA CATCATCCCC AGCAGCCAGA TCACCCAGAT CCCCCTGACC 1440

AAGAGCACCA ACCTGGGCAG CGGCACCAGC GTGGTGAAGG GCCCCGGCTT CACCGGCGGC 1500

GACATCCTGC GCCGCACCAG CCCCGGCCAG ATCAGCACCC TGCGCGTGAA CATCACCGCC 1560

-continued

```
CCCCTGAGCC AGCGCTACCG CGTCCGCATC CGCTACGCCA GCACCACCAA CCTGCAGTTC   1620
CACACCAGCA TCGACGGCCG CCCCATCAAC CAGGGCAACT TCAGCGCCAC CATGAGCAGC   1680
GGCAGCAACC TGCAGAGCGG CAGCTTCCGC ACCGTGGGCT TCACCACCCC CTTCAACTTC   1740
AGCAACGGCA GCAGCGTGTT CACCCTGAGC GCCCACGTGT TCAACAGCGG CAACGAGGTG   1800
TACATCGACC GCATCGAGTT CGTGCCCGCC GAGGTGACCT TCGAGGCCGA GTACGACCTG   1860
GAGAGGGCTC AGAAGGCCGT GAACGAGCTG TTCACCAGCA GCAACCAGAT CGGCCTGAAG   1920
ACCGACGTGA CCGACTACCA CATCGATCAG GTGAGCAACC TGGTGGAGTG CCTGAGCGAC   1980
GAGTTCTGCC TGGACGAGAA GAAGGAGCTG AGCGAGAAGG TGAAGCACGC CAAGCGCCTG   2040
AGCGACGAGC GCAACCTGCT GCAGGACCCC AACTTCCGCG GCATCAACCG CCAGCTGGAC   2100
CGCGGCTGGC GCGGCAGCAC CGACATCACC ATCCAGGGCG GCGACGACGT GTTCAAGGAG   2160
AACTACGTGA CCCTGCTGGG CACCTTCGAC GAGTGCTACC CCACCTACCT GTACCAGAAG   2220
ATCGACGAGA GCAAGCTGAA GGCCTACACC CGCTACCAGC TGCGCGGCTA CATCGAGGAC   2280
AGCCAGGACC TGGAGATCTA CCTGATCCGC TACAACGCCA AGCACGAGAC CGTGAACGTG   2340
CCCGGCACCG GCAGCCTGTG GCCCCTGAGC GCCCCCAGCC CCATCGGCAA GTGCGCCCAC   2400
CACAGCCACC ACTTCAGCCT GGACATCGAC GTGGGCTGCA CCGACCTGAA CGAGGACCTG   2460
GGCGTGTGGG TGATCTTCAA GATCAAGACC CAGGACGGCC ACGCCCGCCT GGGCAACCTG   2520
GAGTTCCTGG AGGAGAAGCC CCTGGTGGGC GAGGCCCTGG CCCGCGTGAA GCGCGCCGAG   2580
AAGAAGTGGC GCGACAAGCG CGAGAAGCTG GAGTGGGAGA CCAACATCGT GTACAAGGAG   2640
GCCAAGGAGA GCGTGGACGC CCTGTTCGTG AACAGCCAGT ACGACCGCCT GCAGGCCGAC   2700
ACCAACATCG CCATGATCCA CGCCGCCGAC AAGCGCGTGC ACAGCATTCG CGAGGCCTAC   2760
CTGCCCGAGC TGAGCGTGAT CCCCGGCGTG AACGCCGCCA TCTTCGAGGA GCTGGAGGGC   2820
CGCATCTTCA CCGCCTTCAG CCTGTACGAC GCCCGCAACG TGATCAAGAA CGGCGACTTC   2880
AACAACGGCC TGAGCTGCTG GAACGTGAAG GGCCACGTGG ACGTGGAGGA GCAGAACAAC   2940
CACCGCAGCG TGCTGGTGGT GCCCGAGTGG GAGGCCGAGG TGAGCCAGGA GGTGCGCGTG   3000
TGCCCCGGCC GCGGCTACAT CCTGCGCGTG ACCGCCTACA AGGAGGGCTA CGGCGAGGGC   3060
TGCGTGACCA TCCACGAGAT CGAGAACAAC ACCGACGAGC TCAAGTTCAG CAACTGCGTG   3120
GAGGAGGAGG TGTACCCCAA CAACACCGTG ACCTGCAACG ACTACACCGC CACCCAGGAG   3180
GAGTACGAGG GCACCTACAC CAGCCGCAAC CGCGGCTACG ACGGCGCCTA CGAGAGCAAC   3240
AGCAGCGTGC CCGCCGACTA CGCCAGCGCC TACGAGGAGA AGGCCTACAC CGACGGCCGC   3300
CGCGACAACC CCTGCGAGAG CAACCGCGGC TACGGCGACT ACACCCCCCT GCCCGCCGGC   3360
TACGTGACCA AGGAGCTGGA GTACTTCCCC GAGACCGACA AGGTGTGGAT CGAGATCGGC   3420
GAGACCGAGG GCACCTTCAT CGTGGACAGC GTGGAGCTGC TGCTGATGGA GGAGTAGTAC   3480
ATGTGATAGT ACGTAAGCTC GAGGATCT                                      3508
```

(2) INFORMATION FOR SEQ ID NO:7:

(i) SEQUENCE CHARACTERISTICS:
(A) LENGTH: 3546 base pairs
(B) TYPE: nucleic acid
(C) STRANDEDNESS: single
(D) TOPOLOGY: linear (ii) MOLECULE TYPE: Other nucleic acid
(A) DESCRIPTION: Full-length hybrid maize-optimized DNA sequence encoding a heat stable cryIA(b) protein -continued as contained in pCIB5512

(iii) HYPOTHETICAL: YES (iv) ANTI-SENSE: NO (ix) FEATURE:
(A) NAME/KEY: CDS
(B) LOCATION: 1..3543

(xi) SEQUENCE DESCRIPTION: SEQ ID NO:7:

```
ATG GAC AAC AAC CCC AAC ATC AAC GAG TGC ATC CCC TAC AAC TGC CTG        48
Met Asp Asn Asn Pro Asn Ile Asn Glu Cys Ile Pro Tyr Asn Cys Leu
  1               5                  10                  15

AGC AAC CCC GAG GTG GAG GTG CTG GGC GGC GAG CGC ATC GAG ACC GGC        96
Ser Asn Pro Glu Val Glu Val Leu Gly Gly Glu Arg Ile Glu Thr Gly
             20                  25                  30

TAC ACC CCC ATC GAC ATC AGC CTG AGC CTG ACC CAG TTC CTG CTG AGC       144
Tyr Thr Pro Ile Asp Ile Ser Leu Ser Leu Thr Gln Phe Leu Leu Ser
         35                  40                  45

GAG TTC GTG CCC GGC GCC GGC TTC GTG CTG GGC CTG GTG GAC ATC ATC       192
Glu Phe Val Pro Gly Ala Gly Phe Val Leu Gly Leu Val Asp Ile Ile
     50                  55                  60

TGG GGC ATC TTC GGC CCC AGC CAG TGG GAC GCC TTC CTG GTG CAG ATC       240
Trp Gly Ile Phe Gly Pro Ser Gln Trp Asp Ala Phe Leu Val Gln Ile
 65                  70                  75                  80

GAG CAG CTG ATC AAC CAG CGC ATC GAG GAG TTC GCC CGC AAC CAG GCC       288
Glu Gln Leu Ile Asn Gln Arg Ile Glu Glu Phe Ala Arg Asn Gln Ala
                 85                  90                  95

ATC AGC CGC CTG GAG GGC CTG AGC AAC CTG TAC CAA ATC TAC GCC GAG       336
Ile Ser Arg Leu Glu Gly Leu Ser Asn Leu Tyr Gln Ile Tyr Ala Glu
            100                 105                 110

AGC TTC CGC GAG TGG GAG GCC GAC CCC ACC AAC CCC GCC CTG CGC GAG       384
Ser Phe Arg Glu Trp Glu Ala Asp Pro Thr Asn Pro Ala Leu Arg Glu
        115                 120                 125

GAG ATG CGC ATC CAG TTC AAC GAC ATG AAC AGC GCC CTG ACC ACC GCC       432
Glu Met Arg Ile Gln Phe Asn Asp Met Asn Ser Ala Leu Thr Thr Ala
    130                 135                 140

ATC CCC CTG TTC GCC GTG CAG AAC TAC CAG GTG CCC CTG CTG AGC GTG       480
Ile Pro Leu Phe Ala Val Gln Asn Tyr Gln Val Pro Leu Leu Ser Val
145                 150                 155                 160

TAC GTG CAG GCC GCC AAC CTG CAC CTG AGC GTG CTG CGC GAC GTC AGC       528
Tyr Val Gln Ala Ala Asn Leu His Leu Ser Val Leu Arg Asp Val Ser
                165                 170                 175

GTG TTC GGC CAG CGC TGG GGC TTC GAC GCC GCC ACC ATC AAC AGC CGC       576
Val Phe Gly Gln Arg Trp Gly Phe Asp Ala Ala Thr Ile Asn Ser Arg
            180                 185                 190

TAC AAC GAC CTG ACC CGC CTG ATC GGC AAC TAC ACC GAC CAC GCC GTG       624
Tyr Asn Asp Leu Thr Arg Leu Ile Gly Asn Tyr Thr Asp His Ala Val
        195                 200                 205

CGC TGG TAC AAC ACC GGC CTG GAG CGC GTG TGG GGT CCC GAC AGC CGC       672
Arg Trp Tyr Asn Thr Gly Leu Glu Arg Val Trp Gly Pro Asp Ser Arg
    210                 215                 220

GAC TGG ATC AGG TAC AAC CAG TTC CGC CGC GAG CTG ACC CTG ACC GTG       720
Asp Trp Ile Arg Tyr Asn Gln Phe Arg Arg Glu Leu Thr Leu Thr Val
225                 230                 235                 240

CTG GAC ATC GTG AGC CTG TTC CCC AAC TAC GAC AGC CGC ACC TAC CCC       768
Leu Asp Ile Val Ser Leu Phe Pro Asn Tyr Asp Ser Arg Thr Tyr Pro
                245                 250                 255

ATC CGC ACC GTG AGC CAG CTG ACC CGC GAG ATT TAC ACC AAC CCC GTG       816
Ile Arg Thr Val Ser Gln Leu Thr Arg Glu Ile Tyr Thr Asn Pro Val
            260                 265                 270
```

-continued

```
CTG GAG AAC TTC GAC GGC AGC TTC CGC GGC AGC GCC CAG GGC ATC GAG      864
Leu Glu Asn Phe Asp Gly Ser Phe Arg Gly Ser Ala Gln Gly Ile Glu
        275                 280                 285

GGC AGC ATC CGC AGC CCC CAC CTG ATG GAC ATC CTG AAC AGC ATC ACC      912
Gly Ser Ile Arg Ser Pro His Leu Met Asp Ile Leu Asn Ser Ile Thr
    290                 295                 300

ATC TAC ACC GAC GCC CAC CGC GGC GAG TAC TAC TGG AGC GGC CAC CAG      960
Ile Tyr Thr Asp Ala His Arg Gly Glu Tyr Tyr Trp Ser Gly His Gln
305                 310                 315                 320

ATC ATG GCC AGC CCC GTC GGC TTC AGC GGC CCC GAG TTC ACC TTC CCC     1008
Ile Met Ala Ser Pro Val Gly Phe Ser Gly Pro Glu Phe Thr Phe Pro
                325                 330                 335

CTG TAC GGC ACC ATG GGC AAC GCT GCA CCT CAG CAG CGC ATC GTG GCA     1056
Leu Tyr Gly Thr Met Gly Asn Ala Ala Pro Gln Gln Arg Ile Val Ala
            340                 345                 350

CAG CTG GGC CAG GGA GTG TAC CGC ACC CTG AGC AGC ACC CTG TAC CGT     1104
Gln Leu Gly Gln Gly Val Tyr Arg Thr Leu Ser Ser Thr Leu Tyr Arg
        355                 360                 365

CGA CCT TTC AAC ATC GGC ATC AAC AAC CAG CAG CTG AGC GTG CTG GAC     1152
Arg Pro Phe Asn Ile Gly Ile Asn Asn Gln Gln Leu Ser Val Leu Asp
    370                 375                 380

GGC ACC GAG TTC GCC TAC GGC ACC AGC AGC AAC CTG CCC AGC GCC GTG     1200
Gly Thr Glu Phe Ala Tyr Gly Thr Ser Ser Asn Leu Pro Ser Ala Val
385                 390                 395                 400

TAC CGC AAG AGC GGC ACC GTG GAC AGC CTG GAC GAG ATC CCC CCT CAG     1248
Tyr Arg Lys Ser Gly Thr Val Asp Ser Leu Asp Glu Ile Pro Pro Gln
                405                 410                 415

AAC AAC AAC GTG CCA CCT CGA CAG GGC TTC AGC CAC CGT CTG AGC CAC     1296
Asn Asn Asn Val Pro Pro Arg Gln Gly Phe Ser His Arg Leu Ser His
            420                 425                 430

GTG AGC ATG TTC CGC AGT GGC TTC AGC AAC AGC AGC GTG AGC ATC ATC     1344
Val Ser Met Phe Arg Ser Gly Phe Ser Asn Ser Ser Val Ser Ile Ile
        435                 440                 445

CGT GCA CCT ATG TTC AGC TGG ATT CAC CGC AGT GCC GAG TTC AAC AAC     1392
Arg Ala Pro Met Phe Ser Trp Ile His Arg Ser Ala Glu Phe Asn Asn
    450                 455                 460

ATC ATC CCC AGC AGC CAG ATC ACC CAG ATC CCC CTG ACC AAG AGC ACC     1440
Ile Ile Pro Ser Ser Gln Ile Thr Gln Ile Pro Leu Thr Lys Ser Thr
465                 470                 475                 480

AAC CTG GGC AGC GGC ACC AGC GTG GTG AAG GGC CCC GGC TTC ACC GGC     1488
Asn Leu Gly Ser Gly Thr Ser Val Val Lys Gly Pro Gly Phe Thr Gly
                485                 490                 495

GGC GAC ATC CTG CGC CGC ACC AGC CCC GGC CAG ATC AGC ACC CTG CGC     1536
Gly Asp Ile Leu Arg Arg Thr Ser Pro Gly Gln Ile Ser Thr Leu Arg
            500                 505                 510

GTG AAC ATC ACC GCC CCC CTG AGC CAG CGC TAC CGC GTC CGC ATC CGC     1584
Val Asn Ile Thr Ala Pro Leu Ser Gln Arg Tyr Arg Val Arg Ile Arg
        515                 520                 525

TAC GCC AGC ACC ACC AAC CTG CAG TTC CAC ACC AGC ATC GAC GGC CGC     1632
Tyr Ala Ser Thr Thr Asn Leu Gln Phe His Thr Ser Ile Asp Gly Arg
    530                 535                 540

CCC ATC AAC CAG GGC AAC TTC AGC GCC ACC ATG AGC AGC GGC AGC AAC     1680
Pro Ile Asn Gln Gly Asn Phe Ser Ala Thr Met Ser Ser Gly Ser Asn
545                 550                 555                 560

CTG CAG AGC GGC AGC TTC CGC ACC GTG GGC TTC ACC ACC CCC TTC AAC     1728
Leu Gln Ser Gly Ser Phe Arg Thr Val Gly Phe Thr Thr Pro Phe Asn
                565                 570                 575

TTC AGC AAC GGC AGC AGC GTG TTC ACC CTG AGC GCC CAC GTG TTC AAC     1776
Phe Ser Asn Gly Ser Ser Val Phe Thr Leu Ser Ala His Val Phe Asn
```

-continued

```
            580                 585                 590

AGC GGC AAC GAG GTG TAC ATC GAC CGC ATC GAG TTC GTG CCC GCC GAG     1824
Ser Gly Asn Glu Val Tyr Ile Asp Arg Ile Glu Phe Val Pro Ala Glu
        595                 600                 605

GTG ACC TTC GAG GCC GAG TAC GAC CTG GAG AGG GCT CAG AAG GCC GTG     1872
Val Thr Phe Glu Ala Glu Tyr Asp Leu Glu Arg Ala Gln Lys Ala Val
    610                 615                 620

AAC GAG CTG TTC ACC AGC AGC AAC CAG ATC GGC CTG AAG ACC GAC GTG     1920
Asn Glu Leu Phe Thr Ser Ser Asn Gln Ile Gly Leu Lys Thr Asp Val
625                 630                 635                 640

ACC GAC TAC CAC ATC GAT CAG GTG AGC AAC CTG GTG GAG TGC TTA AGC     1968
Thr Asp Tyr His Ile Asp Gln Val Ser Asn Leu Val Glu Cys Leu Ser
                645                 650                 655

GAC GAG TTC TGC CTG GAC GAG AAG AAG GAG CTG AGC GAG AAG GTG AAG     2016
Asp Glu Phe Cys Leu Asp Glu Lys Lys Glu Leu Ser Glu Lys Val Lys
            660                 665                 670

CAC GCC AAG CGC CTG AGC GAC GAG CGC AAC CTG CTG CAG GAC CCC AAC     2064
His Ala Lys Arg Leu Ser Asp Glu Arg Asn Leu Leu Gln Asp Pro Asn
        675                 680                 685

TTC CGC GGC ATC AAC CGC CAG CTG GAC CGC GGC TGG CGA GGC AGC ACC     2112
Phe Arg Gly Ile Asn Arg Gln Leu Asp Arg Gly Trp Arg Gly Ser Thr
    690                 695                 700

GAT ATC ACC ATC CAG GGC GGC GAC GAC GTG TTC AAG GAG AAC TAC GTG     2160
Asp Ile Thr Ile Gln Gly Gly Asp Asp Val Phe Lys Glu Asn Tyr Val
705                 710                 715                 720

ACC CTG CTG GGC ACC TTC GAC GAG TGC TAC CCC ACC TAC CTG TAC CAG     2208
Thr Leu Leu Gly Thr Phe Asp Glu Cys Tyr Pro Thr Tyr Leu Tyr Gln
                725                 730                 735

AAG ATC GAC GAG AGC AAG CTG AAG GCC TAC ACC CGC TAC CAG CTG CGC     2256
Lys Ile Asp Glu Ser Lys Leu Lys Ala Tyr Thr Arg Tyr Gln Leu Arg
            740                 745                 750

GGC TAC ATC GAG GAC AGC CAG GAC CTG GAA ATC TAC CTG ATC CGC TAC     2304
Gly Tyr Ile Glu Asp Ser Gln Asp Leu Glu Ile Tyr Leu Ile Arg Tyr
        755                 760                 765

AAC GCC AAG CAC GAG ACC GTG AAC GTG CCC GGC ACC GGC AGC CTG TGG     2352
Asn Ala Lys His Glu Thr Val Asn Val Pro Gly Thr Gly Ser Leu Trp
    770                 775                 780

CCC CTG AGC GCC CCC AGC CCC ATC GGC AAG TGC GGG GAG CCG AAT CGA     2400
Pro Leu Ser Ala Pro Ser Pro Ile Gly Lys Cys Gly Glu Pro Asn Arg
785                 790                 795                 800

TGC GCT CCG CAC CTG GAG TGG AAC CCG GAC CTA GAC TGC AGC TGC AGG     2448
Cys Ala Pro His Leu Glu Trp Asn Pro Asp Leu Asp Cys Ser Cys Arg
                805                 810                 815

GAC GGG GAG AAG TGC GCC CAC CAC AGC CAC CAC TTC AGC CTG GAC ATC     2496
Asp Gly Glu Lys Cys Ala His His Ser His His Phe Ser Leu Asp Ile
            820                 825                 830

GAC GTG GGC TGC ACC GAC CTG AAC GAG GAC CTG GGC GTG TGG GTG ATC     2544
Asp Val Gly Cys Thr Asp Leu Asn Glu Asp Leu Gly Val Trp Val Ile
        835                 840                 845

TTC AAG ATC AAG ACC CAG GAC GGC CAC GCC CGC CTG GGC AAT CTA GAA     2592
Phe Lys Ile Lys Thr Gln Asp Gly His Ala Arg Leu Gly Asn Leu Glu
    850                 855                 860

TTT CTC GAA GAG AAA CCA TTA GTA GGA GAA GCA CTA GCT CGT GTG AAA     2640
Phe Leu Glu Glu Lys Pro Leu Val Gly Glu Ala Leu Ala Arg Val Lys
865                 870                 875                 880

AGA GCG GAG AAA AAA TGG AGA GAC AAA CGT GAA AAA TTG GAA TGG GAA     2688
Arg Ala Glu Lys Lys Trp Arg Asp Lys Arg Glu Lys Leu Glu Trp Glu
                885                 890                 895

ACA AAT ATT GTT TAT AAA GAG GCA AAA GAA TCT GTA GAT GCT TTA TTT     2736
```

-continued

```
Thr Asn Ile Val Tyr Lys Glu Ala Lys Glu Ser Val Asp Ala Leu Phe
            900                 905                 910

GTA AAC TCT CAA TAT GAT AGA TTA CAA GCG GAT ACC AAC ATC GCG ATG      2784
Val Asn Ser Gln Tyr Asp Arg Leu Gln Ala Asp Thr Asn Ile Ala Met
        915                 920                 925

ATT CAT GCG GCA GAT AAA CGC GTT CAT AGC ATT CGA GAA GCT TAT CTG      2832
Ile His Ala Ala Asp Lys Arg Val His Ser Ile Arg Glu Ala Tyr Leu
    930                 935                 940

CCT GAG CTG TCT GTG ATT CCG GGT GTC AAT GCG GCT ATT TTT GAA GAA      2880
Pro Glu Leu Ser Val Ile Pro Gly Val Asn Ala Ala Ile Phe Glu Glu
945                 950                 955                 960

TTA GAA GGG CGT ATT TTC ACT GCA TTC TCC CTA TAT GAT GCG AGA AAT      2928
Leu Glu Gly Arg Ile Phe Thr Ala Phe Ser Leu Tyr Asp Ala Arg Asn
                965                 970                 975

GTC ATT AAA AAT GGT GAT TTT AAT AAT GGC TTA TCC TGC TGG AAC GTG      2976
Val Ile Lys Asn Gly Asp Phe Asn Asn Gly Leu Ser Cys Trp Asn Val
            980                 985                 990

AAA GGG CAT GTA GAT GTA GAA GAA CAA AAC AAC CAC CGT TCG GTC CTT      3024
Lys Gly His Val Asp Val Glu Glu Gln Asn Asn His Arg Ser Val Leu
        995                 1000                1005

GTT GTT CCG GAA TGG GAA GCA GAA GTG TCA CAA GAA GTT CGT GTC TGT      3072
Val Val Pro Glu Trp Glu Ala Glu Val Ser Gln Glu Val Arg Val Cys
    1010                1015                1020

CCG GGT CGT GGC TAT ATC CTT CGT GTC ACA GCG TAC AAG GAG GGA TAT      3120
Pro Gly Arg Gly Tyr Ile Leu Arg Val Thr Ala Tyr Lys Glu Gly Tyr
1025                1030                1035                1040

GGA GAA GGT TGC GTA ACC ATT CAT GAG ATC GAG AAC AAT ACA GAC GAA      3168
Gly Glu Gly Cys Val Thr Ile His Glu Ile Glu Asn Asn Thr Asp Glu
                1045                1050                1055

CTG AAG TTT AGC AAC TGT GTA GAA GAG GAA GTA TAT CCA AAC AAC ACG      3216
Leu Lys Phe Ser Asn Cys Val Glu Glu Glu Val Tyr Pro Asn Asn Thr
            1060                1065                1070

GTA ACG TGT AAT GAT TAT ACT GCG ACT CAA GAA GAA TAT GAG GGT ACG      3264
Val Thr Cys Asn Asp Tyr Thr Ala Thr Gln Glu Glu Tyr Glu Gly Thr
        1075                1080                1085

TAC ACT TCT CGT AAT CGA GGA TAT GAC GGA GCC TAT GAA AGC AAT TCT      3312
Tyr Thr Ser Arg Asn Arg Gly Tyr Asp Gly Ala Tyr Glu Ser Asn Ser
    1090                1095                1100

TCT GTA CCA GCT GAT TAT GCA TCA GCC TAT GAA GAA AAA GCA TAT ACA      3360
Ser Val Pro Ala Asp Tyr Ala Ser Ala Tyr Glu Glu Lys Ala Tyr Thr
1105                1110                1115                1120

GAT GGA CGA AGA GAC AAT CCT TGT GAA TCT AAC AGA GGA TAT GGG GAT      3408
Asp Gly Arg Arg Asp Asn Pro Cys Glu Ser Asn Arg Gly Tyr Gly Asp
                1125                1130                1135

TAC ACA CCA CTA CCA GCT GGC TAT GTG ACA AAA GAA TTA GAG TAC TTC      3456
Tyr Thr Pro Leu Pro Ala Gly Tyr Val Thr Lys Glu Leu Glu Tyr Phe
            1140                1145                1150

CCA GAA ACC GAT AAG GTA TGG ATT GAG ATC GGA GAA ACG GAA GGA ACA      3504
Pro Glu Thr Asp Lys Val Trp Ile Glu Ile Gly Glu Thr Glu Gly Thr
        1155                1160                1165

TTC ATC GTG GAC AGC GTG GAA TTA CTT CTT ATG GAG GAA TAA              3546
Phe Ile Val Asp Ser Val Glu Leu Leu Leu Met Glu Glu
    1170                1175                1180
```

(2) INFORMATION FOR SEQ ID NO:8:

(i) SEQUENCE CHARACTERISTICS:
(A) LENGTH: 1181 amino acids
(B) TYPE: amino acid
(D) TOPOLOGY: linear -continued (ii) MOLECULE TYPE: protein (xi) SEQUENCE DESCRIPTION: SEQ ID NO:8:

```
Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400
```

-continued

```
Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Pro Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
```

-continued

```
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
    850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Arg Leu Gln Ala Asp Thr Asn Ile Ala Met
        915                 920                 925

Ile His Ala Ala Asp Lys Arg Val His Ser Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn His Arg Ser Val Leu
        995                 1000                1005

Val Val Pro Glu Trp Glu Ala Glu Val Ser Gln Glu Val Arg Val Cys
    1010                1015                1020

Pro Gly Arg Gly Tyr Ile Leu Arg Val Thr Ala Tyr Lys Glu Gly Tyr
1025                1030                1035                1040

Gly Glu Gly Cys Val Thr Ile His Glu Ile Glu Asn Asn Thr Asp Glu
                1045                1050                1055

Leu Lys Phe Ser Asn Cys Val Glu Glu Glu Val Tyr Pro Asn Asn Thr
            1060                1065                1070

Val Thr Cys Asn Asp Tyr Thr Ala Thr Gln Glu Glu Tyr Glu Gly Thr
        1075                1080                1085

Tyr Thr Ser Arg Asn Arg Gly Tyr Asp Gly Ala Tyr Glu Ser Asn Ser
    1090                1095                1100

Ser Val Pro Ala Asp Tyr Ala Ser Ala Tyr Glu Glu Lys Ala Tyr Thr
1105                1110                1115                1120

Asp Gly Arg Arg Asp Asn Pro Cys Glu Ser Asn Arg Gly Tyr Gly Asp
                1125                1130                1135

Tyr Thr Pro Leu Pro Ala Gly Tyr Val Thr Lys Glu Leu Glu Tyr Phe
            1140                1145                1150

Pro Glu Thr Asp Lys Val Trp Ile Glu Ile Gly Glu Thr Glu Gly Thr
        1155                1160                1165

Phe Ile Val Asp Ser Val Glu Leu Leu Leu Met Glu Glu
    1170                1175                1180
```

(2) INFORMATION FOR SEQ ID NO:9:

(i) SEQUENCE CHARACTERISTICS:
(A) LENGTH: 3546 base pairs
(B) TYPE: nucleic acid
(C) STRANDEDNESS: single
(D) TOPOLOGY: linear (ii) MOLECULE TYPE: Other nucleic acid
(A) DESCRIPTION: Full-length hybrid maize-optimized -continued DNA sequence encoding a heat stable cryIA(b) protein as contained in pCIB5513

(iii) HYPOTHETICAL: YES (iv) ANTI-SENSE: NO (ix) FEATURE:
(A) NAME/KEY: CDS
(B) LOCATION: 1..3543

(xi) SEQUENCE DESCRIPTION: SEQ ID NO:9:

```
ATG GAC AAC AAC CCC AAC ATC AAC GAG TGC ATC CCC TAC AAC TGC CTG       48
Met Asp Asn Asn Pro Asn Ile Asn Glu Cys Ile Pro Tyr Asn Cys Leu
  1               5                  10                  15

AGC AAC CCC GAG GTG GAG GTG CTG GGC GGC GAG CGC ATC GAG ACC GGC       96
Ser Asn Pro Glu Val Glu Val Leu Gly Gly Glu Arg Ile Glu Thr Gly
             20                  25                  30

TAC ACC CCC ATC GAC ATC AGC CTG AGC CTG ACC CAG TTC CTG CTG AGC      144
Tyr Thr Pro Ile Asp Ile Ser Leu Ser Leu Thr Gln Phe Leu Leu Ser
         35                  40                  45

GAG TTC GTG CCC GGC GCC GGC TTC GTG CTG GGC CTG GTG GAC ATC ATC      192
Glu Phe Val Pro Gly Ala Gly Phe Val Leu Gly Leu Val Asp Ile Ile
     50                  55                  60

TGG GGC ATC TTC GGC CCC AGC CAG TGG GAC GCC TTC CTG GTG CAG ATC      240
Trp Gly Ile Phe Gly Pro Ser Gln Trp Asp Ala Phe Leu Val Gln Ile
 65                  70                  75                  80

GAG CAG CTG ATC AAC CAG CGC ATC GAG GAG TTC GCC CGC AAC CAG GCC      288
Glu Gln Leu Ile Asn Gln Arg Ile Glu Glu Phe Ala Arg Asn Gln Ala
                 85                  90                  95

ATC AGC CGC CTG GAG GGC CTG AGC AAC CTG TAC CAA ATC TAC GCC GAG      336
Ile Ser Arg Leu Glu Gly Leu Ser Asn Leu Tyr Gln Ile Tyr Ala Glu
            100                 105                 110

AGC TTC CGC GAG TGG GAG GCC GAC CCC ACC AAC CCC GCC CTG CGC GAG      384
Ser Phe Arg Glu Trp Glu Ala Asp Pro Thr Asn Pro Ala Leu Arg Glu
        115                 120                 125

GAG ATG CGC ATC CAG TTC AAC GAC ATG AAC AGC GCC CTG ACC ACC GCC      432
Glu Met Arg Ile Gln Phe Asn Asp Met Asn Ser Ala Leu Thr Thr Ala
    130                 135                 140

ATC CCC CTG TTC GCC GTG CAG AAC TAC CAG GTG CCC CTG CTG AGC GTG      480
Ile Pro Leu Phe Ala Val Gln Asn Tyr Gln Val Pro Leu Leu Ser Val
145                 150                 155                 160

TAC GTG CAG GCC GCC AAC CTG CAC CTG AGC GTG CTG CGC GAC GTC AGC      528
Tyr Val Gln Ala Ala Asn Leu His Leu Ser Val Leu Arg Asp Val Ser
                165                 170                 175

GTG TTC GGC CAG CGC TGG GGC TTC GAC GCC GCC ACC ATC AAC AGC CGC      576
Val Phe Gly Gln Arg Trp Gly Phe Asp Ala Ala Thr Ile Asn Ser Arg
            180                 185                 190

TAC AAC GAC CTG ACC CGC CTG ATC GGC AAC TAC ACC GAC CAC GCC GTG      624
Tyr Asn Asp Leu Thr Arg Leu Ile Gly Asn Tyr Thr Asp His Ala Val
        195                 200                 205

CGC TGG TAC AAC ACC GGC CTG GAG CGC GTG TGG GGT CCC GAC AGC CGC      672
Arg Trp Tyr Asn Thr Gly Leu Glu Arg Val Trp Gly Pro Asp Ser Arg
    210                 215                 220

GAC TGG ATC AGG TAC AAC CAG TTC CGC CGC GAG CTG ACC CTG ACC GTG      720
Asp Trp Ile Arg Tyr Asn Gln Phe Arg Arg Glu Leu Thr Leu Thr Val
225                 230                 235                 240

CTG GAC ATC GTG AGC CTG TTC CCC AAC TAC GAC AGC CGC ACC TAC CCC      768
Leu Asp Ile Val Ser Leu Phe Pro Asn Tyr Asp Ser Arg Thr Tyr Pro
                245                 250                 255

ATC CGC ACC GTG AGC CAG CTG ACC CGC GAG ATT TAC ACC AAC CCC GTG      816
Ile Arg Thr Val Ser Gln Leu Thr Arg Glu Ile Tyr Thr Asn Pro Val
```

-continued

```
            260                 265                 270

CTG GAG AAC TTC GAC GGC AGC TTC CGC GGC AGC GCC CAG GGC ATC GAG      864
Leu Glu Asn Phe Asp Gly Ser Phe Arg Gly Ser Ala Gln Gly Ile Glu
        275                 280                 285

GGC AGC ATC CGC AGC CCC CAC CTG ATG GAC ATC CTG AAC AGC ATC ACC      912
Gly Ser Ile Arg Ser Pro His Leu Met Asp Ile Leu Asn Ser Ile Thr
    290                 295                 300

ATC TAC ACC GAC GCC CAC CGC GGC GAG TAC TAC TGG AGC GGC CAC CAG      960
Ile Tyr Thr Asp Ala His Arg Gly Glu Tyr Tyr Trp Ser Gly His Gln
305                 310                 315                 320

ATC ATG GCC AGC CCC GTC GGC TTC AGC GGC CCC GAG TTC ACC TTC CCC     1008
Ile Met Ala Ser Pro Val Gly Phe Ser Gly Pro Glu Phe Thr Phe Pro
                325                 330                 335

CTG TAC GGC ACC ATG GGC AAC GCT GCA CCT CAG CAG CGC ATC GTG GCA     1056
Leu Tyr Gly Thr Met Gly Asn Ala Ala Pro Gln Gln Arg Ile Val Ala
            340                 345                 350

CAG CTG GGC CAG GGA GTG TAC CGC ACC CTG AGC AGC ACC CTG TAC CGT     1104
Gln Leu Gly Gln Gly Val Tyr Arg Thr Leu Ser Ser Thr Leu Tyr Arg
        355                 360                 365

CGA CCT TTC AAC ATC GGC ATC AAC AAC CAG CAG CTG AGC GTG CTG GAC     1152
Arg Pro Phe Asn Ile Gly Ile Asn Asn Gln Gln Leu Ser Val Leu Asp
    370                 375                 380

GGC ACC GAG TTC GCC TAC GGC ACC AGC AGC AAC CTG CCC AGC GCC GTG     1200
Gly Thr Glu Phe Ala Tyr Gly Thr Ser Ser Asn Leu Pro Ser Ala Val
385                 390                 395                 400

TAC CGC AAG AGC GGC ACC GTG GAC AGC CTG GAC GAG ATC CCC CCT CAG     1248
Tyr Arg Lys Ser Gly Thr Val Asp Ser Leu Asp Glu Ile Pro Pro Gln
                405                 410                 415

AAC AAC AAC GTG CCA CCT CGA CAG GGC TTC AGC CAC CGT CTG AGC CAC     1296
Asn Asn Asn Val Pro Pro Arg Gln Gly Phe Ser His Arg Leu Ser His
            420                 425                 430

GTG AGC ATG TTC CGC AGT GGC TTC AGC AAC AGC AGC GTG AGC ATC ATC     1344
Val Ser Met Phe Arg Ser Gly Phe Ser Asn Ser Ser Val Ser Ile Ile
        435                 440                 445

CGT GCA CCT ATG TTC AGC TGG ATT CAC CGC AGT GCC GAG TTC AAC AAC     1392
Arg Ala Pro Met Phe Ser Trp Ile His Arg Ser Ala Glu Phe Asn Asn
    450                 455                 460

ATC ATC CCC AGC AGC CAG ATC ACC CAG ATC CCC CTG ACC AAG AGC ACC     1440
Ile Ile Pro Ser Ser Gln Ile Thr Gln Ile Pro Leu Thr Lys Ser Thr
465                 470                 475                 480

AAC CTG GGC AGC GGC ACC AGC GTG GTG AAG GGC CCC GGC TTC ACC GGC     1488
Asn Leu Gly Ser Gly Thr Ser Val Val Lys Gly Pro Gly Phe Thr Gly
                485                 490                 495

GGC GAC ATC CTG CGC CGC ACC AGC CCC GGC CAG ATC AGC ACC CTG CGC     1536
Gly Asp Ile Leu Arg Arg Thr Ser Pro Gly Gln Ile Ser Thr Leu Arg
            500                 505                 510

GTG AAC ATC ACC GCC CCC CTG AGC CAG CGC TAC CGC GTC CGC ATC CGC     1584
Val Asn Ile Thr Ala Pro Leu Ser Gln Arg Tyr Arg Val Arg Ile Arg
        515                 520                 525

TAC GCC AGC ACC ACC AAC CTG CAG TTC CAC ACC AGC ATC GAC GGC CGC     1632
Tyr Ala Ser Thr Thr Asn Leu Gln Phe His Thr Ser Ile Asp Gly Arg
    530                 535                 540

CCC ATC AAC CAG GGC AAC TTC AGC GCC ACC ATG AGC AGC GGC AGC AAC     1680
Pro Ile Asn Gln Gly Asn Phe Ser Ala Thr Met Ser Ser Gly Ser Asn
545                 550                 555                 560

CTG CAG AGC GGC AGC TTC CGC ACC GTG GGC TTC ACC ACC CCC TTC AAC     1728
Leu Gln Ser Gly Ser Phe Arg Thr Val Gly Phe Thr Thr Pro Phe Asn
                565                 570                 575

TTC AGC AAC GGC AGC AGC GTG TTC ACC CTG AGC GCC CAC GTG TTC AAC     1776
```

-continued

```
Phe Ser Asn Gly Ser Ser Val Phe Thr Leu Ser Ala His Val Phe Asn
            580                 585                 590

AGC GGC AAC GAG GTG TAC ATC GAC CGC ATC GAG TTC GTG CCC GCC GAG     1824
Ser Gly Asn Glu Val Tyr Ile Asp Arg Ile Glu Phe Val Pro Ala Glu
        595                 600                 605

GTG ACC TTC GAG GCC GAG TAC GAC CTG GAG AGG GCT CAG AAG GCC GTG     1872
Val Thr Phe Glu Ala Glu Tyr Asp Leu Glu Arg Ala Gln Lys Ala Val
    610                 615                 620

AAC GAG CTG TTC ACC AGC AGC AAC CAG ATC GGC CTG AAG ACC GAC GTG     1920
Asn Glu Leu Phe Thr Ser Ser Asn Gln Ile Gly Leu Lys Thr Asp Val
625                 630                 635                 640

ACC GAC TAC CAC ATC GAT CAG GTG AGC AAC CTG GTG GAG TGC TTA AGC     1968
Thr Asp Tyr His Ile Asp Gln Val Ser Asn Leu Val Glu Cys Leu Ser
                645                 650                 655

GAC GAG TTC TGC CTG GAC GAG AAG AAG GAG CTG AGC GAG AAG GTG AAG     2016
Asp Glu Phe Cys Leu Asp Glu Lys Lys Glu Leu Ser Glu Lys Val Lys
            660                 665                 670

CAC GCC AAG CGC CTG AGC GAC GAG CGC AAC CTG CTG CAG GAC CCC AAC     2064
His Ala Lys Arg Leu Ser Asp Glu Arg Asn Leu Leu Gln Asp Pro Asn
        675                 680                 685

TTC CGC GGC ATC AAC CGC CAG CTG GAC CGC GGC TGG CGA GGC AGC ACC     2112
Phe Arg Gly Ile Asn Arg Gln Leu Asp Arg Gly Trp Arg Gly Ser Thr
    690                 695                 700

GAT ATC ACC ATC CAG GGC GGC GAC GAC GTG TTC AAG GAG AAC TAC GTG     2160
Asp Ile Thr Ile Gln Gly Gly Asp Asp Val Phe Lys Glu Asn Tyr Val
705                 710                 715                 720

ACC CTG CTG GGC ACC TTC GAC GAG TGC TAC CCC ACC TAC CTG TAC CAG     2208
Thr Leu Leu Gly Thr Phe Asp Glu Cys Tyr Pro Thr Tyr Leu Tyr Gln
                725                 730                 735

AAG ATC GAC GAG AGC AAG CTG AAG GCC TAC ACC CGC TAC CAG CTG CGC     2256
Lys Ile Asp Glu Ser Lys Leu Lys Ala Tyr Thr Arg Tyr Gln Leu Arg
            740                 745                 750

GGC TAC ATC GAG GAC AGC CAG GAC CTG GAA ATC TAC CTG ATC CGC TAC     2304
Gly Tyr Ile Glu Asp Ser Gln Asp Leu Glu Ile Tyr Leu Ile Arg Tyr
        755                 760                 765

AAC GCC AAG CAC GAG ACC GTG AAC GTG CCC GGC ACC GGC AGC CTG TGG     2352
Asn Ala Lys His Glu Thr Val Asn Val Pro Gly Thr Gly Ser Leu Trp
    770                 775                 780

CCC CTG AGC GCC CCC AGC CCC ATC GGC AAG TGC GGG GAG CCG AAT CGA     2400
Pro Leu Ser Ala Pro Ser Pro Ile Gly Lys Cys Gly Glu Pro Asn Arg
785                 790                 795                 800

TGC GCT CCG CAC CTG GAG TGG AAC CCG GAC CTA GAC TGC AGC TGC AGG     2448
Cys Ala Pro His Leu Glu Trp Asn Pro Asp Leu Asp Cys Ser Cys Arg
                805                 810                 815

GAC GGG GAG AAG TGC GCC CAC CAC AGC CAC CAC TTC AGC CTG GAC ATC     2496
Asp Gly Glu Lys Cys Ala His His Ser His His Phe Ser Leu Asp Ile
            820                 825                 830

GAC GTG GGC TGC ACC GAC CTG AAC GAG GAC CTG GGC GTG TGG GTG ATC     2544
Asp Val Gly Cys Thr Asp Leu Asn Glu Asp Leu Gly Val Trp Val Ile
        835                 840                 845

TTC AAG ATC AAG ACC CAG GAC GGC CAC GCC CGC CTG GGC AAT CTA GAG     2592
Phe Lys Ile Lys Thr Gln Asp Gly His Ala Arg Leu Gly Asn Leu Glu
    850                 855                 860

TTC CTG GAG GAG AAG CCC CTG GTG GGC GAG GCC CTG GCC CGC GTG AAG     2640
Phe Leu Glu Glu Lys Pro Leu Val Gly Glu Ala Leu Ala Arg Val Lys
865                 870                 875                 880

CGC GCC GAG AAG AAG TGG CGC GAC AAG CGC GAG AAG CTG GAG TGG GAG     2688
Arg Ala Glu Lys Lys Trp Arg Asp Lys Arg Glu Lys Leu Glu Trp Glu
                885                 890                 895
```

-continued

```
ACC AAC ATC GTG TAC AAG GAG GCC AAG GAG AGC GTG GAC GCC CTG TTC      2736
Thr Asn Ile Val Tyr Lys Glu Ala Lys Glu Ser Val Asp Ala Leu Phe
            900                 905                 910

GTG AAC AGC CAG TAC GAC CGC CTG CAG GCC GAC ACC AAC ATC GCC ATG      2784
Val Asn Ser Gln Tyr Asp Arg Leu Gln Ala Asp Thr Asn Ile Ala Met
        915                 920                 925

ATC CAC GCC GCC GAC AAG CGC GTG CAC AGC ATT CGC GAG GCC TAC CTG      2832
Ile His Ala Ala Asp Lys Arg Val His Ser Ile Arg Glu Ala Tyr Leu
    930                 935                 940

CCC GAG CTG AGC GTG ATC CCC GGC GTG AAC GCC GCC ATC TTC GAG GAA      2880
Pro Glu Leu Ser Val Ile Pro Gly Val Asn Ala Ala Ile Phe Glu Glu
945                 950                 955                 960

CTC GAG GGC CGC ATC TTC ACC GCC TTC AGC CTG TAC GAC GCC CGC AAC      2928
Leu Glu Gly Arg Ile Phe Thr Ala Phe Ser Leu Tyr Asp Ala Arg Asn
                965                 970                 975

GTG ATC AAG AAC GGC GAC TTC AAC AAC GGC CTG AGC TGC TGG AAC GTG      2976
Val Ile Lys Asn Gly Asp Phe Asn Asn Gly Leu Ser Cys Trp Asn Val
            980                 985                 990

AAG GGC CAC GTG GAC GTG GAG GAG CAG AAC AAC CAC CGC AGC GTG CTG      3024
Lys Gly His Val Asp Val Glu Glu Gln Asn Asn His Arg Ser Val Leu
        995                 1000                1005

GTG GTG CCC GAG TGG GAG GCC GAG GTG AGC CAG GAG GTG CGC GTG TGC      3072
Val Val Pro Glu Trp Glu Ala Glu Val Ser Gln Glu Val Arg Val Cys
    1010                1015                1020

CCC GGC CGC GGC TAC ATC CTG CGC GTG ACC GCC TAC AAG GAG GGC TAC      3120
Pro Gly Arg Gly Tyr Ile Leu Arg Val Thr Ala Tyr Lys Glu Gly Tyr
1025                1030                1035                1040

GGC GAG GGC TGC GTG ACC ATC CAC GAG ATC GAG AAC AAC ACC GAC GAG      3168
Gly Glu Gly Cys Val Thr Ile His Glu Ile Glu Asn Asn Thr Asp Glu
                1045                1050                1055

CTC AAG TTC AGC AAC TGC GTG GAG GAG GAG GTG TAC CCC AAC AAC ACC      3216
Leu Lys Phe Ser Asn Cys Val Glu Glu Glu Val Tyr Pro Asn Asn Thr
            1060                1065                1070

GTG ACC TGC AAC GAC TAC ACC GCG ACC CAG GAG GAG TAC GAG GGC ACC      3264
Val Thr Cys Asn Asp Tyr Thr Ala Thr Gln Glu Glu Tyr Glu Gly Thr
        1075                1080                1085

TAC ACC AGC CGC AAC CGC GGC TAC GAC GGC GCC TAC GAG AGC AAC AGC      3312
Tyr Thr Ser Arg Asn Arg Gly Tyr Asp Gly Ala Tyr Glu Ser Asn Ser
    1090                1095                1100

AGC GTG CCC GCC GAC TAC GCC AGC GCC TAC GAG GAG AAG GCC TAC ACC      3360
Ser Val Pro Ala Asp Tyr Ala Ser Ala Tyr Glu Glu Lys Ala Tyr Thr
1105                1110                1115                1120

GAC GGC CGC CGC GAC AAC CCC TGC GAG AGC AAC CGC GGC TAC GGC GAC      3408
Asp Gly Arg Arg Asp Asn Pro Cys Glu Ser Asn Arg Gly Tyr Gly Asp
                1125                1130                1135

TAC ACC CCC CTG CCC GCC GGC TAC GTG ACC AAG GAG CTG GAG TAC TTC      3456
Tyr Thr Pro Leu Pro Ala Gly Tyr Val Thr Lys Glu Leu Glu Tyr Phe
            1140                1145                1150

CCC GAG ACC GAC AAG GTG TGG ATC GAG ATC GGC GAG ACC GAG GGC ACC      3504
Pro Glu Thr Asp Lys Val Trp Ile Glu Ile Gly Glu Thr Glu Gly Thr
        1155                1160                1165

TTC ATC GTG GAC AGC GTG GAG CTG CTG CTG ATG GAG GAG TAG              3546
Phe Ile Val Asp Ser Val Glu Leu Leu Leu Met Glu Glu
    1170                1175                1180
```

(2) INFORMATION FOR SEQ ID NO:10:

(i) SEQUENCE CHARACTERISTICS:
(A) LENGTH: 1181 amino acids
(B) TYPE: amino acid
(D) TOPOLOGY: linear -continued (ii) MOLECULE TYPE: protein (xi) SEQUENCE DESCRIPTION: SEQ ID NO:10:

```
Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400
```

-continued

```
Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Pro Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815
```

-continued

```
Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
    850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Arg Leu Gln Ala Asp Thr Asn Ile Ala Met
        915                 920                 925

Ile His Ala Ala Asp Lys Arg Val His Ser Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn His Arg Ser Val Leu
        995                 1000                1005

Val Val Pro Glu Trp Glu Ala Glu Val Ser Gln Glu Val Arg Val Cys
    1010                1015                1020

Pro Gly Arg Gly Tyr Ile Leu Arg Val Thr Ala Tyr Lys Glu Gly Tyr
1025                1030                1035                1040

Gly Glu Gly Cys Val Thr Ile His Glu Ile Glu Asn Asn Thr Asp Glu
                1045                1050                1055

Leu Lys Phe Ser Asn Cys Val Glu Glu Glu Val Tyr Pro Asn Asn Thr
            1060                1065                1070

Val Thr Cys Asn Asp Tyr Thr Ala Thr Gln Glu Glu Tyr Glu Gly Thr
        1075                1080                1085

Tyr Thr Ser Arg Asn Arg Gly Tyr Asp Gly Ala Tyr Glu Ser Asn Ser
    1090                1095                1100

Ser Val Pro Ala Asp Tyr Ala Ser Ala Tyr Glu Glu Lys Ala Tyr Thr
1105                1110                1115                1120

Asp Gly Arg Arg Asp Asn Pro Cys Glu Ser Asn Arg Gly Tyr Gly Asp
                1125                1130                1135

Tyr Thr Pro Leu Pro Ala Gly Tyr Val Thr Lys Glu Leu Glu Tyr Phe
            1140                1145                1150

Pro Glu Thr Asp Lys Val Trp Ile Glu Ile Gly Glu Thr Glu Gly Thr
        1155                1160                1165

Phe Ile Val Asp Ser Val Glu Leu Leu Leu Met Glu Glu
    1170                1175                1180
```

(2) INFORMATION FOR SEQ ID NO:11:

(i) SEQUENCE CHARACTERISTICS:
(A) LENGTH: 3547 base pairs
(B) TYPE: nucleic acid
(C) STRANDEDNESS: single
(D) TOPOLOGY: linear (ii) MOLECULE TYPE: Other nucleic acid -continued

```
          (A) DESCRIPTION:  Full-length hybrid maize-optimized
               DNA sequence encoding a heat stable cryIA(b) protein
               as contained in pCIB5514

   (iii) HYPOTHETICAL: YES

    (iv) ANTI-SENSE: NO

    (ix) FEATURE:
          (A) NAME/KEY: CDS
          (B) LOCATION: 1..3543

    (xi) SEQUENCE DESCRIPTION: SEQ ID NO:11:

ATG GAC AAC AAC CCC AAC ATC AAC GAG TGC ATC CCC TAC AAC TGC CTG       48
Met Asp Asn Asn Pro Asn Ile Asn Glu Cys Ile Pro Tyr Asn Cys Leu
  1               5                  10                  15

AGC AAC CCC GAG GTG GAG GTG CTG GGC GGC GAG CGC ATC GAG ACC GGC       96
Ser Asn Pro Glu Val Glu Val Leu Gly Gly Glu Arg Ile Glu Thr Gly
             20                  25                  30

TAC ACC CCC ATC GAC ATC AGC CTG AGC CTG ACC CAG TTC CTG CTG AGC      144
Tyr Thr Pro Ile Asp Ile Ser Leu Ser Leu Thr Gln Phe Leu Leu Ser
         35                  40                  45

GAG TTC GTG CCC GGC GCC GGC TTC GTG CTG GGC CTG GTG GAC ATC ATC      192
Glu Phe Val Pro Gly Ala Gly Phe Val Leu Gly Leu Val Asp Ile Ile
     50                  55                  60

TGG GGC ATC TTC GGC CCC AGC CAG TGG GAC GCC TTC CTG GTG CAG ATC      240
Trp Gly Ile Phe Gly Pro Ser Gln Trp Asp Ala Phe Leu Val Gln Ile
 65                  70                  75                  80

GAG CAG CTG ATC AAC CAG CGC ATC GAG GAG TTC GCC CGC AAC CAG GCC      288
Glu Gln Leu Ile Asn Gln Arg Ile Glu Glu Phe Ala Arg Asn Gln Ala
                 85                  90                  95

ATC AGC CGC CTG GAG GGC CTG AGC AAC CTG TAC CAA ATC TAC GCC GAG      336
Ile Ser Arg Leu Glu Gly Leu Ser Asn Leu Tyr Gln Ile Tyr Ala Glu
            100                 105                 110

AGC TTC CGC GAG TGG GAG GCC GAC CCC ACC AAC CCC GCC CTG CGC GAG      384
Ser Phe Arg Glu Trp Glu Ala Asp Pro Thr Asn Pro Ala Leu Arg Glu
        115                 120                 125

GAG ATG CGC ATC CAG TTC AAC GAC ATG AAC AGC GCC CTG ACC ACC GCC      432
Glu Met Arg Ile Gln Phe Asn Asp Met Asn Ser Ala Leu Thr Thr Ala
    130                 135                 140

ATC CCC CTG TTC GCC GTG CAG AAC TAC CAG GTG CCC CTG CTG AGC GTG      480
Ile Pro Leu Phe Ala Val Gln Asn Tyr Gln Val Pro Leu Leu Ser Val
145                 150                 155                 160

TAC GTG CAG GCC GCC AAC CTG CAC CTG AGC GTG CTG CGC GAC GTC AGC      528
Tyr Val Gln Ala Ala Asn Leu His Leu Ser Val Leu Arg Asp Val Ser
                165                 170                 175

GTG TTC GGC CAG CGC TGG GGC TTC GAC GCC GCC ACC ATC AAC AGC CGC      576
Val Phe Gly Gln Arg Trp Gly Phe Asp Ala Ala Thr Ile Asn Ser Arg
            180                 185                 190

TAC AAC GAC CTG ACC CGC CTG ATC GGC AAC TAC ACC GAC CAC GCC GTG      624
Tyr Asn Asp Leu Thr Arg Leu Ile Gly Asn Tyr Thr Asp His Ala Val
        195                 200                 205

CGC TGG TAC AAC ACC GGC CTG GAG CGC GTG TGG GGT CCC GAC AGC CGC      672
Arg Trp Tyr Asn Thr Gly Leu Glu Arg Val Trp Gly Pro Asp Ser Arg
    210                 215                 220

GAC TGG ATC AGG TAC AAC CAG TTC CGC CGC GAG CTG ACC CTG ACC GTG      720
Asp Trp Ile Arg Tyr Asn Gln Phe Arg Arg Glu Leu Thr Leu Thr Val
225                 230                 235                 240

CTG GAC ATC GTG AGC CTG TTC CCC AAC TAC GAC AGC CGC ACC TAC CCC      768
Leu Asp Ile Val Ser Leu Phe Pro Asn Tyr Asp Ser Arg Thr Tyr Pro
                245                 250                 255

ATC CGC ACC GTG AGC CAG CTG ACC CGC GAG ATT TAC ACC AAC CCC GTG      816
```

-continued

```
Ile Arg Thr Val Ser Gln Leu Thr Arg Glu Ile Tyr Thr Asn Pro Val
            260                 265                 270

CTG GAG AAC TTC GAC GGC AGC TTC CGC GGC AGC GCC CAG GGC ATC GAG      864
Leu Glu Asn Phe Asp Gly Ser Phe Arg Gly Ser Ala Gln Gly Ile Glu
        275                 280                 285

GGC AGC ATC CGC AGC CCC CAC CTG ATG GAC ATC CTG AAC AGC ATC ACC      912
Gly Ser Ile Arg Ser Pro His Leu Met Asp Ile Leu Asn Ser Ile Thr
    290                 295                 300

ATC TAC ACC GAC GCC CAC CGC GGC GAG TAC TAC TGG AGC GGC CAC CAG      960
Ile Tyr Thr Asp Ala His Arg Gly Glu Tyr Tyr Trp Ser Gly His Gln
305                 310                 315                 320

ATC ATG GCC AGC CCC GTC GGC TTC AGC GGC CCC GAG TTC ACC TTC CCC     1008
Ile Met Ala Ser Pro Val Gly Phe Ser Gly Pro Glu Phe Thr Phe Pro
                325                 330                 335

CTG TAC GGC ACC ATG GGC AAC GCT GCA CCT CAG CAG CGC ATC GTG GCA     1056
Leu Tyr Gly Thr Met Gly Asn Ala Ala Pro Gln Gln Arg Ile Val Ala
            340                 345                 350

CAG CTG GGC CAG GGA GTG TAC CGC ACC CTG AGC AGC ACC CTG TAC CGT     1104
Gln Leu Gly Gln Gly Val Tyr Arg Thr Leu Ser Ser Thr Leu Tyr Arg
        355                 360                 365

CGA CCT TTC AAC ATC GGC ATC AAC AAC CAG CAG CTG AGC GTG CTG GAC     1152
Arg Pro Phe Asn Ile Gly Ile Asn Asn Gln Gln Leu Ser Val Leu Asp
    370                 375                 380

GGC ACC GAG TTC GCC TAC GGC ACC AGC AGC AAC CTG CCC AGC GCC GTG     1200
Gly Thr Glu Phe Ala Tyr Gly Thr Ser Ser Asn Leu Pro Ser Ala Val
385                 390                 395                 400

TAC CGC AAG AGC GGC ACC GTG GAC AGC CTG GAC GAG ATC CCC CCT CAG     1248
Tyr Arg Lys Ser Gly Thr Val Asp Ser Leu Asp Glu Ile Pro Pro Gln
                405                 410                 415

AAC AAC AAC GTG CCA CCT CGA CAG GGC TTC AGC CAC CGT CTG AGC CAC     1296
Asn Asn Asn Val Pro Pro Arg Gln Gly Phe Ser His Arg Leu Ser His
            420                 425                 430

GTG AGC ATG TTC CGC AGT GGC TTC AGC AAC AGC AGC GTG AGC ATC ATC     1344
Val Ser Met Phe Arg Ser Gly Phe Ser Asn Ser Ser Val Ser Ile Ile
        435                 440                 445

CGT GCA CCT ATG TTC AGC TGG ATT CAC CGC AGT GCC GAG TTC AAC AAC     1392
Arg Ala Pro Met Phe Ser Trp Ile His Arg Ser Ala Glu Phe Asn Asn
    450                 455                 460

ATC ATC CCC AGC AGC CAG ATC ACC CAG ATC CCC CTG ACC AAG AGC ACC     1440
Ile Ile Pro Ser Ser Gln Ile Thr Gln Ile Pro Leu Thr Lys Ser Thr
465                 470                 475                 480

AAC CTG GGC AGC GGC ACC AGC GTG GTG AAG GGC CCC GGC TTC ACC GGC     1488
Asn Leu Gly Ser Gly Thr Ser Val Val Lys Gly Pro Gly Phe Thr Gly
                485                 490                 495

GGC GAC ATC CTG CGC CGC ACC AGC CCC GGC CAG ATC AGC ACC CTG CGC     1536
Gly Asp Ile Leu Arg Arg Thr Ser Pro Gly Gln Ile Ser Thr Leu Arg
            500                 505                 510

GTG AAC ATC ACC GCC CCC CTG AGC CAG CGC TAC CGC GTC CGC ATC CGC     1584
Val Asn Ile Thr Ala Pro Leu Ser Gln Arg Tyr Arg Val Arg Ile Arg
        515                 520                 525

TAC GCC AGC ACC ACC AAC CTG CAG TTC CAC ACC AGC ATC GAC GGC CGC     1632
Tyr Ala Ser Thr Thr Asn Leu Gln Phe His Thr Ser Ile Asp Gly Arg
    530                 535                 540

CCC ATC AAC CAG GGC AAC TTC AGC GCC ACC ATG AGC AGC GGC AGC AAC     1680
Pro Ile Asn Gln Gly Asn Phe Ser Ala Thr Met Ser Ser Gly Ser Asn
545                 550                 555                 560

CTG CAG AGC GGC AGC TTC CGC ACC GTG GGC TTC ACC ACC CCC TTC AAC     1728
Leu Gln Ser Gly Ser Phe Arg Thr Val Gly Phe Thr Thr Pro Phe Asn
                565                 570                 575
```

-continued

```
TTC AGC AAC GGC AGC AGC GTG TTC ACC CTG AGC GCC CAC GTG TTC AAC      1776
Phe Ser Asn Gly Ser Ser Val Phe Thr Leu Ser Ala His Val Phe Asn
            580                 585                 590

AGC GGC AAC GAG GTG TAC ATC GAC CGC ATC GAG TTC GTG CCC GCC GAG      1824
Ser Gly Asn Glu Val Tyr Ile Asp Arg Ile Glu Phe Val Pro Ala Glu
        595                 600                 605

GTG ACC TTC GAG GCC GAG TAC GAC CTG GAG AGG GCT CAG AAG GCC GTG      1872
Val Thr Phe Glu Ala Glu Tyr Asp Leu Glu Arg Ala Gln Lys Ala Val
    610                 615                 620

AAC GAG CTG TTC ACC AGC AGC AAC CAG ATC GGC CTG AAG ACC GAC GTG      1920
Asn Glu Leu Phe Thr Ser Ser Asn Gln Ile Gly Leu Lys Thr Asp Val
625                 630                 635                 640

ACC GAC TAC CAC ATC GAT CAA GTA TCC AAT TTA GTT GAG TGT TTA TCT      1968
Thr Asp Tyr His Ile Asp Gln Val Ser Asn Leu Val Glu Cys Leu Ser
                645                 650                 655

GAT GAA TTT TGT CTG GAT GAA AAA AAA GAA TTG TCC GAG AAA GTC AAA      2016
Asp Glu Phe Cys Leu Asp Glu Lys Lys Glu Leu Ser Glu Lys Val Lys
            660                 665                 670

CAT GCG AAG CGA CTT AGT GAT GAG CGG AAT TTA CTT CAA GAT CCA AAC      2064
His Ala Lys Arg Leu Ser Asp Glu Arg Asn Leu Leu Gln Asp Pro Asn
        675                 680                 685

TTT AGA GGG ATC AAT AGA CAA CTA GAC CGT GGC TGG AGA GGA AGT ACG      2112
Phe Arg Gly Ile Asn Arg Gln Leu Asp Arg Gly Trp Arg Gly Ser Thr
    690                 695                 700

GAT ATT ACC ATC CAA GGA GGC GAT GAC GTA TTC AAA GAG AAT TAC GTT      2160
Asp Ile Thr Ile Gln Gly Gly Asp Asp Val Phe Lys Glu Asn Tyr Val
705                 710                 715                 720

ACG CTA TTG GGT ACC TTT GAT GAG TGC TAT CCA ACG TAT TTA TAT CAA      2208
Thr Leu Leu Gly Thr Phe Asp Glu Cys Tyr Pro Thr Tyr Leu Tyr Gln
                725                 730                 735

AAA ATA GAT GAG TCG AAA TTA AAA GCC TAT ACC CGT TAC CAA TTA AGA      2256
Lys Ile Asp Glu Ser Lys Leu Lys Ala Tyr Thr Arg Tyr Gln Leu Arg
            740                 745                 750

GGG TAT ATC GAA GAT AGT CAA GAC TTA GAA ATC TAT TTA ATT CGC TAC      2304
Gly Tyr Ile Glu Asp Ser Gln Asp Leu Glu Ile Tyr Leu Ile Arg Tyr
        755                 760                 765

AAT GCC AAA CAC GAA ACA GTA AAT GTG CCA GGT ACG GGT TCC TTA TGG      2352
Asn Ala Lys His Glu Thr Val Asn Val Pro Gly Thr Gly Ser Leu Trp
    770                 775                 780

CCG CTT TCA GCC CCA AGT CCA ATC GGC AAG TGC GGG GAG CCG AAT CGA      2400
Pro Leu Ser Ala Pro Ser Pro Ile Gly Lys Cys Gly Glu Pro Asn Arg
785                 790                 795                 800

TGC GCT CCG CAC CTG GAG TGG AAC CCG GAC CTA GAC TGC AGC TGC AGG      2448
Cys Ala Pro His Leu Glu Trp Asn Pro Asp Leu Asp Cys Ser Cys Arg
                805                 810                 815

GAC GGG GAG AAG TGC GCC CAC CAC AGC CAC CAC TTC AGC CTG GAC ATC      2496
Asp Gly Glu Lys Cys Ala His His Ser His His Phe Ser Leu Asp Ile
            820                 825                 830

GAC GTG GGC TGC ACC GAC CTG AAC GAG GAC CTG GGC GTG TGG GTG ATC      2544
Asp Val Gly Cys Thr Asp Leu Asn Glu Asp Leu Gly Val Trp Val Ile
        835                 840                 845

TTC AAG ATC AAG ACC CAG GAC GGC CAC GCC CGC CTG GGC AAT CTA GAA      2592
Phe Lys Ile Lys Thr Gln Asp Gly His Ala Arg Leu Gly Asn Leu Glu
    850                 855                 860

TTT CTC GAA GAG AAA CCA TTA GTA GGA GAA GCA CTA GCT CGT GTG AAA      2640
Phe Leu Glu Glu Lys Pro Leu Val Gly Glu Ala Leu Ala Arg Val Lys
865                 870                 875                 880

AGA GCG GAG AAA AAA TGG AGA GAC AAA CGT GAA AAA TTG GAA TGG GAA      2688
Arg Ala Glu Lys Lys Trp Arg Asp Lys Arg Glu Lys Leu Glu Trp Glu
                885                 890                 895
```

-continued

```
ACA AAT ATT GTT TAT AAA GAG GCA AAA GAA TCT GTA GAT GCT TTA TTT      2736
Thr Asn Ile Val Tyr Lys Glu Ala Lys Glu Ser Val Asp Ala Leu Phe
            900                 905                 910

GTA AAC TCT CAA TAT GAT AGA TTA CAA GCG GAT ACC AAC ATC GCG ATG      2784
Val Asn Ser Gln Tyr Asp Arg Leu Gln Ala Asp Thr Asn Ile Ala Met
        915                 920                 925

ATT CAT GCG GCA GAT AAA CGC GTT CAT AGC ATT CGA GAA GCT TAT CTG      2832
Ile His Ala Ala Asp Lys Arg Val His Ser Ile Arg Glu Ala Tyr Leu
    930                 935                 940

CCT GAG CTG TCT GTG ATT CCG GGT GTC AAT GCG GCT ATT TTT GAA GAA      2880
Pro Glu Leu Ser Val Ile Pro Gly Val Asn Ala Ala Ile Phe Glu Glu
945                 950                 955                 960

TTA GAA GGG CGT ATT TTC ACT GCA TTC TCC CTA TAT GAT GCG AGA AAT      2928
Leu Glu Gly Arg Ile Phe Thr Ala Phe Ser Leu Tyr Asp Ala Arg Asn
                965                 970                 975

GTC ATT AAA AAT GGT GAT TTT AAT AAT GGC TTA TCC TGC TGG AAC GTG      2976
Val Ile Lys Asn Gly Asp Phe Asn Asn Gly Leu Ser Cys Trp Asn Val
            980                 985                 990

AAA GGG CAT GTA GAT GTA GAA GAA CAA AAC AAC CAC CGT TCG GTC CTT      3024
Lys Gly His Val Asp Val Glu Glu Gln Asn Asn His Arg Ser Val Leu
        995                 1000                1005

GTT GTT CCG GAA TGG GAA GCA GAA GTG TCA CAA GAA GTT CGT GTC TGT      3072
Val Val Pro Glu Trp Glu Ala Glu Val Ser Gln Glu Val Arg Val Cys
    1010                1015                1020

CCG GGT CGT GGC TAT ATC CTT CGT GTC ACA GCG TAC AAG GAG GGA TAT      3120
Pro Gly Arg Gly Tyr Ile Leu Arg Val Thr Ala Tyr Lys Glu Gly Tyr
1025                1030                1035                1040

GGA GAA GGT TGC GTA ACC ATT CAT GAG ATC GAG AAC AAT ACA GAC GAA      3168
Gly Glu Gly Cys Val Thr Ile His Glu Ile Glu Asn Asn Thr Asp Glu
                1045                1050                1055

CTG AAG TTT AGC AAC TGT GTA GAA GAG GAA GTA TAT CCA AAC AAC ACG      3216
Leu Lys Phe Ser Asn Cys Val Glu Glu Glu Val Tyr Pro Asn Asn Thr
            1060                1065                1070

GTA ACG TGT AAT GAT TAT ACT GCG ACT CAA GAA GAA TAT GAG GGT ACG      3264
Val Thr Cys Asn Asp Tyr Thr Ala Thr Gln Glu Glu Tyr Glu Gly Thr
        1075                1080                1085

TAC ACT TCT CGT AAT CGA GGA TAT GAC GGA GCC TAT GAA AGC AAT TCT      3312
Tyr Thr Ser Arg Asn Arg Gly Tyr Asp Gly Ala Tyr Glu Ser Asn Ser
    1090                1095                1100

TCT GTA CCA GCT GAT TAT GCA TCA GCC TAT GAA GAA AAA GCA TAT ACA      3360
Ser Val Pro Ala Asp Tyr Ala Ser Ala Tyr Glu Glu Lys Ala Tyr Thr
1105                1110                1115                1120

GAT GGA CGA AGA GAC AAT CCT TGT GAA TCT AAC AGA GGA TAT GGG GAT      3408
Asp Gly Arg Arg Asp Asn Pro Cys Glu Ser Asn Arg Gly Tyr Gly Asp
                1125                1130                1135

TAC ACA CCA CTA CCA GCT GGC TAT GTG ACA AAA GAA TTA GAG TAC TTC      3456
Tyr Thr Pro Leu Pro Ala Gly Tyr Val Thr Lys Glu Leu Glu Tyr Phe
            1140                1145                1150

CCA GAA ACC GAT AAG GTA TGG ATT GAG ATC GGA GAA ACG GAA GGA ACA      3504
Pro Glu Thr Asp Lys Val Trp Ile Glu Ile Gly Glu Thr Glu Gly Thr
        1155                1160                1165

TTC ATC GTG GAC AGC GTG GAA TTA CTT CTT ATG GAG GAA TAAG             3547
Phe Ile Val Asp Ser Val Glu Leu Leu Leu Met Glu Glu
    1170                1175                1180
```

(2) INFORMATION FOR SEQ ID NO:12:

(i) SEQUENCE CHARACTERISTICS:
   (A) LENGTH: 1181 amino acids
   (B) TYPE: amino acid -continued (D) TOPOLOGY: linear (ii) MOLECULE TYPE: protein (xi) SEQUENCE DESCRIPTION: SEQ ID NO:12:

```
Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
```

-continued

```
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Pro Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815
```

-continued

```
Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
    850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Arg Leu Gln Ala Asp Thr Asn Ile Ala Met
        915                 920                 925

Ile His Ala Ala Asp Lys Arg Val His Ser Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn His Arg Ser Val Leu
        995                 1000                1005

Val Val Pro Glu Trp Glu Ala Glu Val Ser Gln Glu Val Arg Val Cys
    1010                1015                1020

Pro Gly Arg Gly Tyr Ile Leu Arg Val Thr Ala Tyr Lys Glu Gly Tyr
1025                1030                1035                1040

Gly Glu Gly Cys Val Thr Ile His Glu Ile Glu Asn Asn Thr Asp Glu
                1045                1050                1055

Leu Lys Phe Ser Asn Cys Val Glu Glu Glu Val Tyr Pro Asn Asn Thr
            1060                1065                1070

Val Thr Cys Asn Asp Tyr Thr Ala Thr Gln Glu Glu Tyr Glu Gly Thr
        1075                1080                1085

Tyr Thr Ser Arg Asn Arg Gly Tyr Asp Gly Ala Tyr Glu Ser Asn Ser
    1090                1095                1100

Ser Val Pro Ala Asp Tyr Ala Ser Ala Tyr Glu Glu Lys Ala Tyr Thr
1105                1110                1115                1120

Asp Gly Arg Arg Asp Asn Pro Cys Glu Ser Asn Arg Gly Tyr Gly Asp
                1125                1130                1135

Tyr Thr Pro Leu Pro Ala Gly Tyr Val Thr Lys Glu Leu Glu Tyr Phe
            1140                1145                1150

Pro Glu Thr Asp Lys Val Trp Ile Glu Ile Gly Glu Thr Glu Gly Thr
        1155                1160                1165

Phe Ile Val Asp Ser Val Glu Leu Leu Leu Met Glu Glu
    1170                1175                1180
```